United States Patent
Sidduri

(10) Patent No.: US 6,441,180 B1
(45) Date of Patent: Aug. 27, 2002

(54) TETRAZOLYL-PHENYL ACTAMIDE GLUCOKINASE ACTIVATORS

(75) Inventor: Achyutharao Sidduri, Livingston, NJ (US)

(73) Assignee: Hoffmann-La Roche Inc., Nutley, NJ (US)

(*) Notice: Subject to any disclaimer, the term of this patent is extended or adjusted under 35 U.S.C. 154(b) by 0 days.

(21) Appl. No.: 10/050,508

(22) Filed: Jan. 16, 2002

Related U.S. Application Data

(62) Division of application No. 09/975,713, filed on Oct. 11, 2001, which is a division of application No. 09/924,247, filed on Aug. 8, 2001.
(60) Provisional application No. 60/225,494, filed on Aug. 15, 2000.

(51) Int. Cl.[7] ................. C07D 401/02; C07D 401/10
(52) U.S. Cl. ................. 546/268.1; 546/268.4
(58) Field of Search ............. 546/268.1, 268.4

(56) References Cited

U.S. PATENT DOCUMENTS

| | | |
|---|---|---|
| 5,113,013 A | 5/1992 | Powell et al. |
| 5,461,049 A | 10/1995 | O'Brien et al. |
| 5,468,867 A | 11/1995 | Fisher et al. |
| 5,929,110 A | 7/1999 | Nugent et al. |

OTHER PUBLICATIONS

Colowick, S.P., *The Enzymes*, vol. 9, pp. 1–48, (1973).
Chipkin, S. R., Kelly,K.L., and Ruderman, N.B., *Joslin's Diabetes*.
Printz, R.G., Magnuson, M.A., and Granner, D.K., *Ann. Rev. Nutrition*, vol. 13 Annual Review, Inc., Palo Alto, CA, pp. 463–496, (1993).
Meglasson, M.D. and Matschinsky, F.M., *Amer. J. Physiol.* 246, E1–E13, (1984).
Grupe, A., Hultgren, B., Ryan, A. Et Al., *Cell*, vol. 83, pp. 69–78 (1995).
Liang, Y., Kesavan, P., Wang, L. Et Al. *Biochem. J.* vol. 309, pp. 167–173, (1995).
Glaser, B., Kesavan, P., Heyman, M. Et Al., *New England J. Med.* vol. 338, pp. 226–230, (1998).
Katayama, T.; Umeno, M., *Chem. Lett.* (1991), p. 2073.
Reddy, G.S.; Tam, *Organometallics*, (1984), vol. 3, p. 630.
Novak, J.; Salemink, C.A., *Synthesis*, (1983), vol. 7, p. 597.
Eapen, K.C.; Dua, S.S.; Tamboroski, C., *J. Org. Chem.* 1984, vol. 49, p. 478.
Clark, J.H.; McClinton, M.A.; Jone, C.W.; Landon, P.; Bishop; D. Blade, R.J. *Tetrahedron Lett.* (1989), p. 2133.
Lucas, H.J. and Kennedy, E.R., *Org. Synth. Coll.,.* vol. II, (1943), p. 351.
Knochel and Rao, *Tetrahedron* vol. 49, p. 29, (1993).
Ahmar, M.; Girard, C.; Bloch, R. *Tetrahedron Lett*, (1989), p. 7053.
Chen, Q. Et Al, *J. Chem. Soc. Comm* . (1993) p. 1389.

*Primary Examiner*—Joseph K. McKane
*Assistant Examiner*—Golam M. M. Shameem
(74) *Attorney, Agent, or Firm*—George W. Johnston; Dennis P. Tramaloni

(57) ABSTRACT

Tetrazolyl-phenyl acetamides are active as glucokinase activators, and are able to increase insulin secretion, which makes them useful for treating type II diabetes.

17 Claims, No Drawings

TETRAZOLYL-PHENYL ACTAMIDE GLUCOKINASE ACTIVATORS

This application is a divisional of Ser. No. 09/975,713, filed Oct. 11, 2001, which is a divisional of Ser. No. 09/924,247, filed Aug. 8, 2001, which is a non-provisional of provisional Ser. No. 60/225,494, filed Aug. 15, 2000.

BACKGROUND OF THE INVENTION

Glucokinase (GK) is one of four hexokinases found in mammals [Colowick, S. P., in *The Enzymes*, Vol. 9 (P. Boyer, ed.) Academic Press, New York, N.Y., pages 1–48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in *Joslin's Diabetes* (C. R. Khan and G. C. Wier, eds.), Lea and Febiger, Philadelphia, Pa., pages 97–115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (~10–15 mM) levels following a carbohydrate-containing meal [Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463–496, 1993]. These findings contributed over a decade ago to the hypothesis that GK functions as a glucose sensor in β-cells and hepatocytes (Meglasson, M. D. and Matschinsky, F. M. *Amer. J. Physiol.* 246, E1–E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69–78, 1995; Ferrie, T., Riu, E., Bosch, F. et al., *FASEB J.*, 10, 1213–1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167–173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226–230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents are useful for treating type II diabetes.

SUMMARY OF THE INVENTION

This invention provides a tetrazole selected from the group consisting of a compound of the formula:

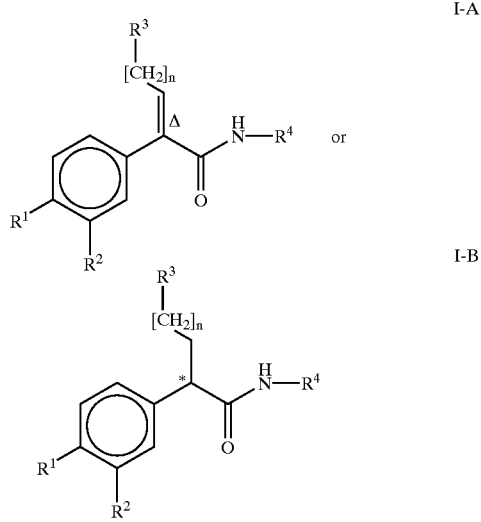

where one of $R^1$ or $R^2$ is

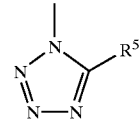

(this tetrazole is linked to the remainder of the molecule by the N, as represented here) and the other is hydrogen, halogen, lower alkyl sulfonyl, perfluoro-lower alkyl, cyano, or nitro; $R^3$ is cycloalkyl; $R^4$ is (O)NHR$^6$ or a five- or six-membered heteroaromatic ring connected by a ring carbon atom to the amide group shown, which heteroaromatic ring contains from 1 to 3 heteroatoms selected from the group consisting of oxygen, sulfur and nitrogen with a first heteroatom being nitrogen adjacent to the connecting ring carbon atom, said heteroaromatic ring being unsubstituted or monosubstituted with halogen at a position on a ring carbon atom other than that adjacent to said connecting carbon atom; n is 0 or 1; $R^5$ is lower alkyl, or perfluoro lower alkyl; $R^6$ is hydrogen or lower alkyl; and pharmaceutically acceptable salts of the tetrazole.

Formula I-A depicts the isomeric bond when it is not hydrogenated. Formula I-B depicts the bond when it is hydrogenated. Accordingly the Δ denotes a trans configuration across the double bond in formula I-A, and the * represents the asymmetric carbon atom in formula I-B. Tetrazoles which are compounds of formula I-B are preferably in the R configuration.

The compounds of formula IA or IB are glucokinase activators useful for increasing insulin secretion in the treatment of type II diabetes.

DETAILED DESCRIPTION OF THE INVENTION

One embodiment of formula I-A or of formula I-B is a tetrazole where $R^4$ is a five- or six-membered heteroaromatic ring connected by a ring carbon atom to the amide group shown, which heteroaromatic ring contains from 1 to 3 heteroatoms selected from the group consisting of oxygen, sulfur and nitrogen with a first heteroatom being nitrogen adjacent to the connecting ring carbon atom, said heteroaromatic ring being unsubstituted or monosubstituted with halogen at a position on a ring carbon atom other than that adjacent to said connecting carbon atom. Formula I-A1 represents this embodiment as a compound of formula I-A, and Formula I-B1 represents this embodiment as a compound of formula I-B.

Another embodiment of formula I-A or formula I-B is a tetrazole where $R^4$ is —C(O)—$NHR^6$ where $R^6$ is hydrogen or lower alkyl. Formula I-A2 represents this embodiment as a compound of formula I-A. Formula I-B2 represents this embodiment as a compound of formula I-B.

In most tetrazoles of this invention, it is preferred that $R^1$ be

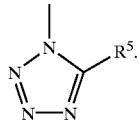

It is also preferred that $R^5$ be lower alkyl (such as methyl). It is further preferred that $R^3$ be cyclopentyl, although cyclohexyl and cycloheptyl are also possible. When $R^4$ is a six-membered heteroaromatic ring, it is preferably substituted or unsubstituted pyridine. When $R^4$ is a 5-membered heteroaromatic ring, it is preferably substituted or unsubstituted thiazole. When substituted, either ring is preferably monosubstituted, and the preferred substituent is halogen such as bromo. $R^2$ is preferably halogen (such as fluoro or chloro) or perfluoro lower alkyl (such as trifluoromethyl) and $R^6$ is preferably methyl. Thus, a tetrazole of formula IA or IB may include any one or more of these conditions in any selected combination. In addition, any one or more of these conditions may be applied to any tetrazole of this invention as described herein. For example, in any tetrazole of this invention with substituted pyridine, the preferred substituent is bromo.

In particular, in tetrazoles of formula I-A1, $R^1$ is

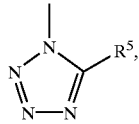

$R^5$ is lower alkyl, and $R^3$ is cyclopentyl (formula I-A1a). In one embodiment of formula I-A1a, $R^4$ is a six-membered heteroaromatic ring, in particular substituted or unsubstituted pyridine. In such a tetrazole, $R^2$ may be halogen. An example is:

(E)-N-(5-bromo-pyridin-2-yl)-3-cyclopentyl-2-[3-fluoro-4-(5-methyl-tetrazol-1-yl)-phenyl]-acrylamide In another embodiment of formula I-A1a, $R^4$ is a 5-membered heteroaromatic ring, in particular substituted or unsubstituted thiazole. In such a tetrazole, $R^2$ may be halogen or perfluoro lower alkyl, or $R^2$ may be lower alkyl sulfonyl. Examples of the former tetrazoles are (E)-3-cyclopentyl-2-[4-(5-methyl-tetrazol-1-yl)-3-trifluoromethyl-phenyl-]-N-thiazol-2-yl-acrylamide
(E)-4-cyclopentyl-2-[4-(5-methyl-tetrazol-1-yl)-3-trifluoromethyl-phenyl-]-but-2-enoic acid-thiazol-2-ylamnide
(E)-2-[3-chloro-4-(5-methyl-tetrazol-1-yl)-phenyl]-3-cyclopentyl-N-thiazol-2-yl-acrylamide
(E)-3-cyclopentyl-2-[3-fluoro-4-(5-methyl-tetrazol-1-yl)-phenyl]-N-thiazol-2-yl-acrylamide
An example of the latter tetrazole is
(E)-3-cyclopentyl-2-[3-methanesulfonyl-4-(5-methyl-tetrazol-1-yl)-phenyl-]-N-thiazol-2-yl-acrylamide In another tetrazole of formula I-A1, $R^1$ is

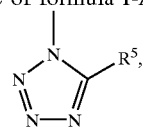

is halogen and $R^4$ is substituted or unsubstituted thiazole. In these tetrazoles, $R^5$ is lower alkyl or perfluoro lower alkyl. $R^3$ may be cyclohexyl, as in
(E)-2-[3-chloro-4-(5-methyl-tetrazol-1-yl)-phenyl]-3-cyclohexyl-N-thiazol-2-yl-acrylamide
(E)-2-[3-chloro-4-(5-trifluoromethyl-tetrazol-1-yl)-phenyl]-3-cyclohexyl-N-thiazol-2-yl-acrylamide
Or $R^3$ may be cycloheptyl, as in
(E)-2-[3-chloro-4-(5-methyl-tetrazol-1-yl)-phenyl]-3-cycloheptyl-N-thiazol-2-yl-acrylamide
(E)-N-(5-bromo-thiazol-2-yl)-2-[3-chloro-4-(5-methyl-tetrazol-1-yl)-phenyl]-3-cycloheptyl-acrylamide This invention is also directed to tetrazoles of formula I-A2 (i.e. tetrazoles of formula I-A) where $R^4$ is —C(O)—$NHR^6$ where $R^6$ is hydrogen or lower alkyl. In preferred such tetrazoles, $R^1$ is

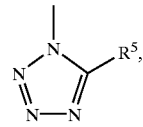

$R^5$ is lower alkyl, $R^3$ is cyclopentyl, and $R^6$ is methyl, especially where $R^2$ is halogen. An example of such a tetrazole is
(E)-1-{3-cyclopentyl-2-[3-fluoro-4-(5-methyl-tetrazol-1-yl)-phenyl-acryloyl}3-methyl-urea This invention is also directed to tetrazoles of formula I-B, for example tetrazoles of formula I-B1 (where $R^4$ is a five- or six-membered heteroaromatic ring as described in detail above). In such tetrazoles, $R^1$ is preferably

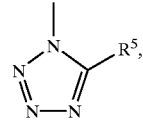

$R^5$ is lower alkyl, and $R^3$ is cyclopentyl (formula I-B1a). In one embodiment of formula I-B1a, $R^4$ is a six-membered heteroaromatic ring, in particular substituted or unsubstituted pyridine. In such a tetrazole, $R^2$ may be halogen. Examples of such tetrazoles are
N-(5-bromo-pyridin-2-yl)-3-cyclopentyl-2-[3-fluoro-4-(5-methyl-tetrazol-1-yl)-phenyl]-propionamide
N-(5-bromo-pyridin-2-yl)-3-cyclopentyl-2-[3-chloro-4-(5-methyl-tetrazol-1-yl)-phenyl]-propionamide
Alternatively, $R^2$ may be perfluoro lower alkyl, for example in
N-(5-bromo-pyridin-2-yl)-3-cyclopentyl-2-[4-(5-methyl-tetrazol-1-yl)-3-trifluoromethyl-phenyl]-propionamide In another embodiment of formula I-B1a, $R^4$ is a 5-membered heteroaromatic ring, in particular substituted or unsubstituted thiazole. In such a tetrazole, $R^2$ may be halogen or perfluoro lower alkyl, or $R^2$ may be lower alkyl sulfonyl. Examples of these tetrazoles are
3-cyclopentyl-2-[3-fluoro-4-(5-methyl-tetrazol-1-yl)-phenyl]-N-thiazol-2-yl-propionamide
2-[3-chloro-4-(5-methyl-tetrazol-1-yl)-phenyl]-3-cyclopentyl-N-thiazol-2-yl-propionamide
3-cyclopentyl-2-[4-(5-methyl-tetrazol-1-yl)-3-trifluoromethyl-phenyl]-N-thiazol-2-yl-propionamide In another tetrazole of formula I-B1, $R^1$ is

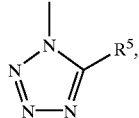

$R^3$ is cyclohexyl and $R^4$ is substituted or unsubstituted thiazole. In these tetrazoles, $R^2$ is halogen. $R^5$ may be lower alkyl as in 2-[3-chloro-4-(5-methyl-tetrazol-1-yl)-phenyl]-3-cyclohexyl-N-thiazol-2-yl-propionamide or perfluoro lower alkyl as in 2-[3-chloro-4-(5-trifluoromethyl-tetrazol-1-yl)-phenyl]-3-cyclohexyl-N-thiazol-2-yl-propionamide.

In any tetrazoles of this invention, $R^2$ and $R^1$ can be exchanged so that $R^2$ is

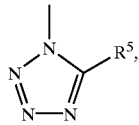

in particular certain tetrazoles of formula I-B1. In these tetrazoles, it is preferred that $R^1$ is lower alkyl sulfonyl, $R^4$ is substituted or unsubstituted thiazole, and $R^3$ is cyclopentyl. An example of such a tetrazole is
3-cyclopentyl-2-[4-methanesulfonyl-3-(5-methyl-tetrazol-1-yl)-phenyl]-N-thiazol-2-yl-propionamide This invention is also directed to tetrazoles of formula I-B2 (i.e. tetrazoles of formula I-B) where $R^4$ is —C(O)—NHR$^6$ where $R^6$ is hydrogen or lower alkyl. In such tetrazoles, it is preferred that $R^1$ is

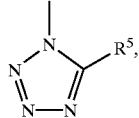

$R^3$ is cyclopentyl, $R^6$ is methyl, and $R^2$ is perfluoro lower alkyl or halogen. Examples of such tetrazoles are
1-{3-cyclopentyl-2-[4-(5-methyl-tetrazol-1-yl)-3-trifluoromethyl-phenyl}-propionyl-3-methyl-urea
1-{2-[3-chloro-4-(5-methyl-tetrazol-1-yl)-phenyl]-3-cyclopentyl-propionyl-3-methyl-urea As used herein, the term "lower alkyl" means straight chain or branched chain alkyl groups having from 1 to 4 carbon atoms, such as methyl, ethyl, propyl, isopropyl, preferably methyl and ethyl. As used herein, "cycloalkyl" means a saturated hydrocarbon ring having from 3 to 8 carbon atoms, preferably from 5 to 7 carbon atoms. As used herein, "perfluoro-lower alkyl" means any lower alkyl group wherein all of the hydrogens of the lower alkyl group are substituted or replaced by fluoro, such as trifluoromethyl, pentafluoroethyl, heptafluoropropyl, etc.

As used herein, "lower alkyl sulfonyl" means a lower alkyl group as defined above bound to the rest of the molecule through the sulfur atom in the sulfonyl group.

As used herein, the term "halogen" or "halo" unless otherwise stated designates all four halogens, i.e. fluorine, chlorine, bromine and iodine (fluoro, chloro, bromo, and iodo).

The heteroaromatic ring defined by $R^4$ is five- or six-membered heteroaromatic ring (e.g. an aromatic ring having at least one heteroatom) which is connected by a ring carbon to the amide group shown in formula IA or formula IB. This ring has from 1 to 3 heteroatoms selected from the group consisting of oxygen, nitrogen, and sulfur. The nitrogen is found adjacent to the connecting ring carbon atom. Preferred heteroaromatic rings include pyridinyl and thiazolyl. The rings may be unsubstituted, or mono-substituted with a halogen at a position on a ring carbon which is not adjacent to the connecting ring carbon atom.

The term "trans" as used herein designates that the largest substituents attached across the double bond are on opposite sides of the double bond and have the "E" configuration. The term "cis" designates that the two largest substituents attached across the double bond are on the same side as the double bond.

In the compounds of formula I-B, the "*" designates the asymmetric carbon atom in the compounds with the R optical configuration being preferred. The compounds of formula I-B may be present in the R form or as a racemic or other mixture of compounds having the R and S optical configuration at the asymmetric carbon shown. The pure R enantiomers are preferred. As stated above, the compounds of this invention are useful as glucokinase activators for increasing insulin secretion for treatment of type II diabetes. Compounds of formula I-A having the trans configuration across the double bond (represented by the Δ) have this glucokinase activity.

The term "pharmaceutically acceptable salts" as used herein include any salt with both inorganic or organic pharmaceutically acceptable acids such as hydrochloric acid, hydrobromic acid, nitric acid, sulfuric acid, phosphoric acid, citric acid, formic acid, maleic acid, acetic acid, succinic acid, tartaric acid, methanesulfonic acid, para-toluene sulfonic acid and the like. The term "pharmaceutically acceptable salts" also includes any pharmaceutically acceptable base salt such as amine salts, trialkyl amine salts and the like. Such salts can be formed quite readily by those skilled in the art using standard techniques.

The three Schemes that follow demonstrate how to make tetrazoles of formulae IA or IB from known starting materials.

Scheme 1
Tetrazole Starting Materials

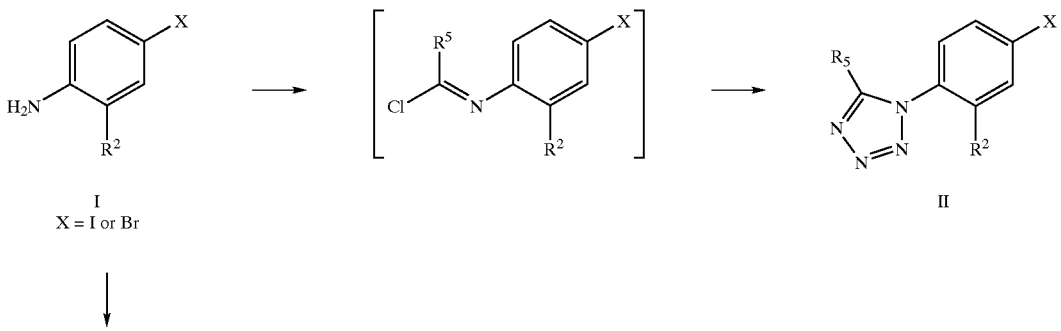

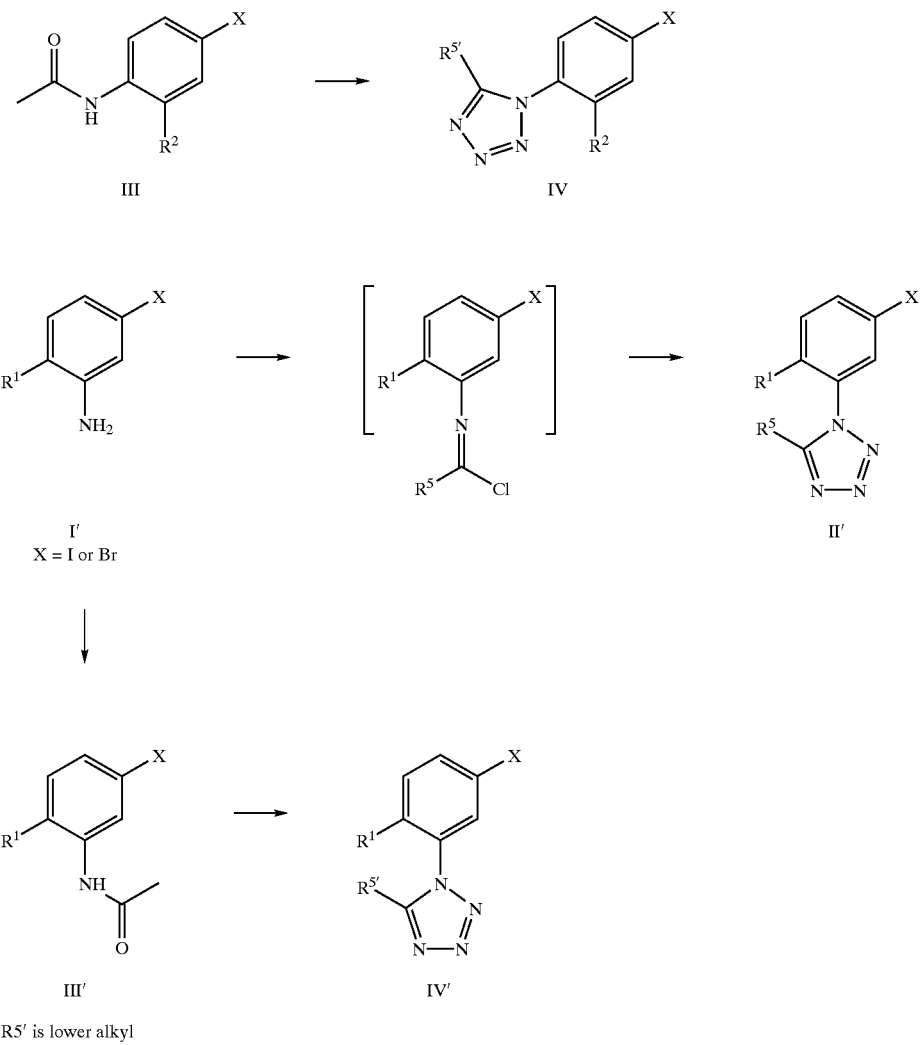
R5' is lower alkyl
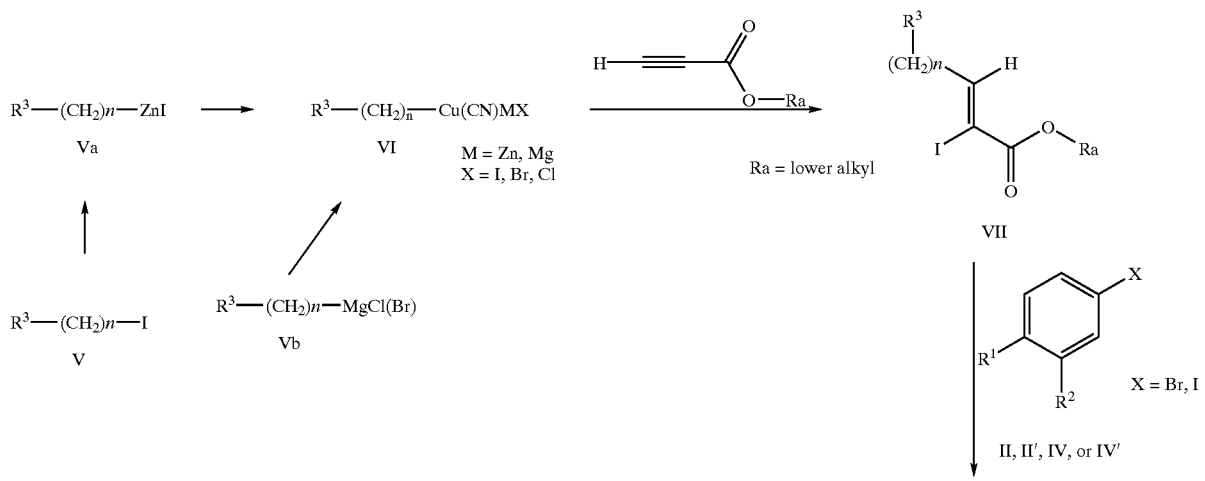
Scheme 2
Synthesis of Tetrazole-Olefins

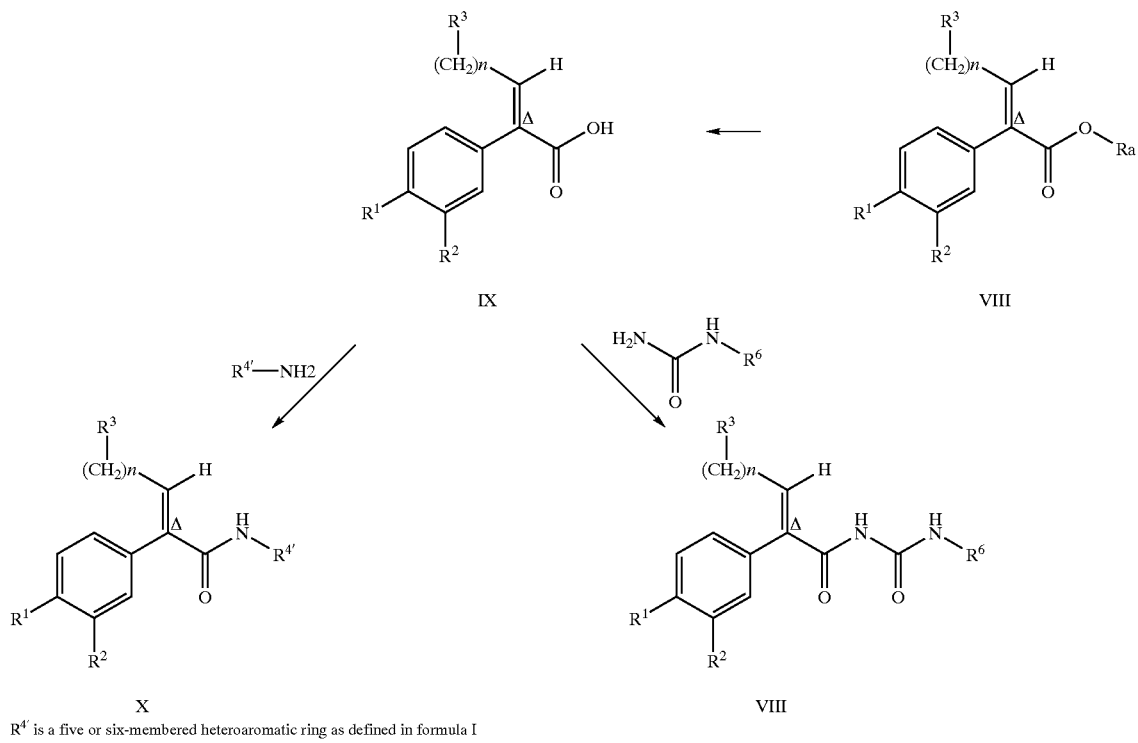
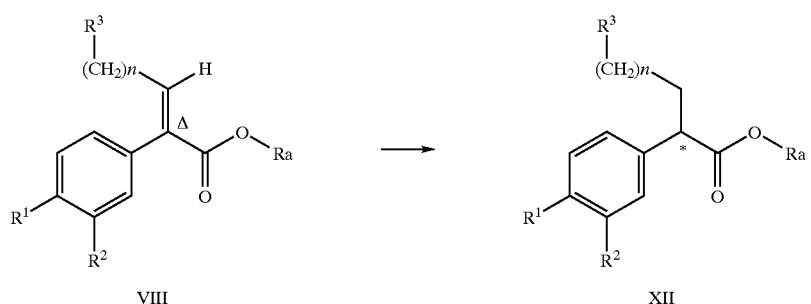
Scheme 3
Synthesis of Racemic Tetrazoles
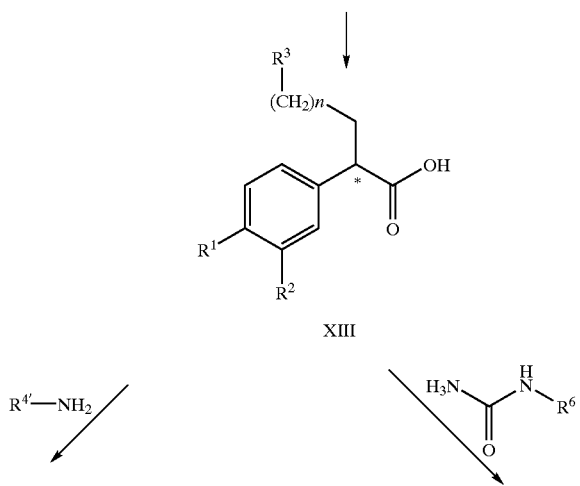

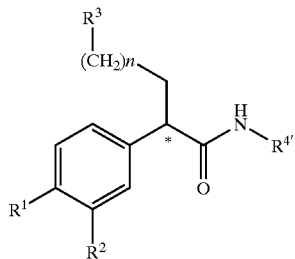

XIV $R^{4'}$ is a five or six-membered heteroaromatic ring as defined in formula I

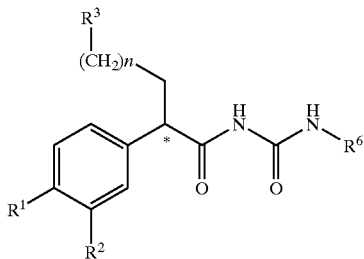

XV $R^1$, $R^2$, $R^3$, $R^4$, $R^5$, and n are as in formulae I-A and I-B. As shown in the Schemes, the $R^1$ and $R^2$ positions are interchangeable. Therefore the Schemes include and demonstrate the same reactions, intermediates, and compounds with the tetrazole or its precursors in the $R^2$ position and the other $R^1/R^2$ variables (hydrogen, halogen, lower alkyl sulfonyl, perfluoro lower alkyl, cyano, or nitro) in the $R^1$ position and vice versa.

The compounds of this invention are produced by reacting phenyl-substituted tetrazoles (II, II', IV, or IV') with cycloalkyl-substituted acrylic acid lower alkyl esters (VII) to obtain tetrazolyl-phenyl cycloalkyl propenoic ester (VIII), which is hydrolyzed or reduced and hydrolyzed to give the corresponding propenoic or acrylic acid (IX or XIII), to which is added the desired heteroaromatic ring or urea/substituted urea to obtain a compound of formula I-A or formula I-B. The phenyl-substituted tetrazoles (II, II', IV, or IV') may be produced from the appropriate substituted anilines which are known and available materials or can be produced by a skilled person from known materials. The cycloalkyl-substituted acrylic acid lower alkyl esters may be produced from cycloalkyl halides, which are similarly known and available materials or can be produced by a skilled person from known materials. These reactions are discussed in more detail below.

Scheme 1 shows how to obtain starting materials for compounds of this invention. For compounds where $R^5$ is lower alkyl or perfluoro lower alkyl, substituted aniline I is reacted with lower alkyl or perfluoro lower alkyl carboxylic acid (corresponding to $R^5$) using conventional methods for converting an amine to an imine, for example in a suspension of triphenylphosphine in carbon tetrachloride treated with an organic base such as triethylamine. Accordingly the reaction proceeds by way of an imidoyl halide (e.g. chloride) intermediate, which is reacted with an azide such as sodium azide as to obtain tetrazole II by conventional methods for tetrazole formation from an imidoyl chloride.

For compounds of this invention where $R^5$ is lower alkyl, an alternate route is acylation of aniline I as described above to acetamide III under standard conditions (such as acetic anhydride in tetrahydrofuran), followed by reaction with an azide to obtain tetrazole IV by conventional methods for tetrazole formation from a lower alkyl amide.

Aniline I where X is either iodo or bromo and either of $R^1$ or $R^2$ is hydrogen, nitro, fluorine, chlorine, bromine, thiol, and trifluoromethyl or where $R^1$ is thiomethyl or where $R^2$ is cyano, is known and commercially available, and may also be made by a skilled chemist from known materials. Other aniline I compounds may be made by a skilled chemist from known materials.

For example aniline 1 where $R^1$ or $R^2$ is $C_{1-C_4}$ lower alkyl sulfonyl can be made from aniline I where $R^1$ or $R^2$ is thiol.

The thiol is alkylated under standard conditions to provide the lower alkyl thio, which can then be oxidized to the corresponding lower alkyl sulfonyl. Any conventional method of oxidizing alkyl thio substituents to sulfones can be used to effect this conversion.

Aniline I where $R^1$ is cyano (and X is bromo) can be made from aniline I where $R^1$ is nitro and X is bromo by reducing the nitro to an amine by any conventional method, then diazotizing the amine to the corresponding diazonium salt, and reacting with a standard cyano group transferring agent to obtain aniline I where $R^1$ is cyano.

Aniline I where $R^1$ or $R^2$ are perfluoro lower alkyl can be made from the corresponding halo compounds of formula VIII. Any conventional method for converting an aromatic halo group to a desired perfluoro lower alkyl group may be used (see for example, Katayama, T.; Umeno, M., *Chem. Lett.* 1991, 2073; Reddy, G. S.; Tam., *Organometallics*, 1984, 3, 630; Novak, J.; Salemink, C. A., *Synthesis*, 1983, 7, 597; Eapen, K. C.; Dua, S. S.; Tamboroski, C., *J. Org. Chem.* 1984, 49, 478; Chen, Q.-Y.; Duan, J.-X. *J. Chem. Soc. Chem. Comm.* 1993, 1389; Clark, J. H.; McClinton, M. A.; Jone, C. W.; Landon, P.; Bisohp, D.; Blade, R. J., *Tetrahedron Lett.* 1989, 2133; Powell, R. L.; Heaton, C. A, U. S. Pat. No. 5,113,013).

Aniline I where $R^1$ or $R^2$ is iodo may be made from the corresponding nitro compounds of formula VIII. The nitro is reduced to an amine and the amine is diazotized to the diazonium salt, which is then converted to the iodo compound by conventional methods (see for example Lucas, H. J. and Kennedy, E. R., *Org. Synth. Coll.* Vol. II 1943, 351).

For compounds of formula I-A, the above tetrazoles are coupled with acrylic acid lower alkyl ester (VIII) to ultimately provide tetrazolyl-phenyl cycloalkyl propenoic acid IX to which may be coupled a heteroaromatic amine or a urea or lower alkyl urea to obtain a compound of formula I-A.

Scheme 2 shows how to obtain compounds of formula I-A in more detail. $R^3$ is cycloalkyl. To obtain cycloalkyl-2-iodo-acrylic acid methyl ester VII, organozinc reagent Va (obtained by conventional methods from commercially available iodide V) or commercially available Grignard reagent Vb and soluble copper reagent is reacted with lower alkyl propiolate in a regio- and stereo-selective 1,4-conjugate addition to obtain a vinylcopper intermediate which upon iodonolysis under standard conditions produces VII where $R^3$ and the iodo substituent are in syn relationship to each other. The addition operates by way of a cycloalkyl copper cyano zinc or magnesium halide intermediate obtained by treating Va or Vb with copper cyanide and lithium chloride in an aprotic solvent such as tetrahydrofuran. Compound VII is then reacted with activated zinc metal (Knochel and Rao, Tetrahedron 49:29, 1993) to give a vinylzinc intermediate which may be coupled with either compound II or compound IV in the presence of a source of Pd(0) to give tetrazole-phenyl-cycloalkyl-acrylic acid methyl ester VIII with the phenyl-substituted tetrazole replacing the iodide to yield the trans orientation across the double bond.

Compound VIII is then hydrolyzed under standard alkaline conditions to the corresponding acid IX. Heterocyclic compound X may then be formed by coupling the desired heteroaromatic amine to compound IX under conventional conditions for adding an amine to an acid. Urea compound XI may be obtained by coupling urea or lower alkyl urea to compound IX under conventional conditions for converting an acid to a urea.

Compound VIII is the starting material for compounds of formula I-B. As shown in Scheme 3, these compounds may be obtained by reducing compound VIII to tetrazole-phenyl-cycloalkyl propanoic acid lower alkyl ester XII. This can be accomplished using conventional metal catalysts such as nickel in the presence of a reducing agent under standard conditions. Compound XII is then hydrolyzed under standard conditions to provide the corresponding acid XIII. Heterocyclic compound XIV may then be formed by coupling the desired heteroaromatic amine to compound XIII under conventional conditions for adding an amine to an acid. Urea compound XV may be obtained by coupling urea or lower alkyl urea to compound XIII under conventional conditions for converting an acid to a urea.

If it is desired to produce the R enantiomer of the compound of formula I-B free of the other enantiomers, the compound of formula XIII can be separated into this isomer from its racemate by any conventional chemical means. Among the preferred chemical means is to react the compound of formula XIII with an optically active base. Any conventional optically active base can be utilized to carry out this resolution. Among the preferred optically active bases are the optically active amine bases such as alpha-methylbenzylamine, quinine, dehydroabietylamine and alpha-methylnaphthylamine. Any of the conventional techniques utilized in resolving organic acids with optically active organic amine bases can be utilized in carrying out this reaction.

In the resolution step, the compound of formula XIII is reacted with the optically active base in an inert organic solvent medium to produce salts of the optically active amine with both the R and S isomers of the compound of formula XIII. In the formation of these salts, temperatures and pressure are not critical and the salt formation can take place at room temperature and atmospheric pressure. The R and S salts can be separated by any conventional method such as fractional crystallization. After crystallization, each of the salts can be converted to the respective compounds of formula XIII in the R and S configuration by hydrolysis with an acid. Among the preferred acids are dilute aqueous acids, i.e., from about 0.001N to 2N aqueous acids, such as aqueous sulfuric or aqueous hydrochloric acid. By means of measuring the optical rotation of the optically pure crystallized acid of formula XIII, one can obtain the configuration of this crystalline material. If this crystallized acid has a negative rotation, then this crystallized acid has the R configuration. The configuration of formula XIII which is produced by this method of resolution is carried out throughout the entire reaction scheme to produce the desired R of formula IB. The separation of R and S isomers can also be achieved using an enzymatic ester hydrolysis of any lower alkyl esters corresponding to the compound of the formula XII (see, for example, Ahmar, M.; Girard, C.; Bloch, R., *Tetrahedron Lett,* 1989, 7053), which results in the formation of corresponding chiral acid and chiral ester. The ester and the acid can be separated by any conventional method of separating an acid from an ester. The preferred method of resolution of racemates of the compounds of the formula XIII is via the formation of corresponding diastereomeric esters or amides. These diastereomeric esters or amides can be prepared by coupling the carboxylic acids of the formula XIII with a chiral alcohol or a chiral amine. This reaction can be carried out using any conventional method of coupling a carboxylic acid with an alcohol or an amine. The corresponding diastereomers of compounds of the formula XIII can then be separated using any conventional separation methods. The resulting pure diastereomeric esters or amides can then be hydrolyzed to yield the corresponding pure R and S isomers. The hydrolysis reaction can be carried out using any conventional method to hydrolyze an ester or an amide without racemization.

All of the compounds of formula IA or formula IB described in the Examples activated glucokinase in vitro in accordance with the procedure described in Example A.

The following compounds were tested and found to have excellent glucokinase activating activity in vivo when administered orally in accordance with the procedure described in Example B.

N-(5-bromo-pyridin-2-yl)-3-cyclopentyl-2-[3-chloro-4-(5-methyl-tetrazol-1-yl)-phenyl]-propionamide N-(5-bromo-pyridin-2-yl)-3-cyclopentyl-2-[4-(5-methyl-tetrazol-1-yl)-3-trifluoromethyl-phenyl]-propionamide 3-Cyclopentyl-2-[4-(5-methyl-tetrazol-1-yl)-3-trifluoromethyl-phenyl]-N-thiazol-2-yl-propionamide (E)-2-[3-chloro-4-(5-methyl-tetrazol-1-yl)-phenyl]-3-cyclohexyl-N-thiazol-2-yl-acrylamide (E)-2-[3-chloro-4-(5-trifluoromethyl-tetrazol-1-yl)-phenyl]-3-cyclohexyl-N-thiazol-2-yl-acrylamide (E)-2-[3-chloro-4-(5-methyl-tetrazol-1-yl)-phenyl]-3-cycloheptyl-N-thiazol-2-yl-acrylamide (E)-N-(5-bromo-thiazol-2-yl)-2-[3-chloro-4-(5-methyl-tetrazol-1-yl)-phenyl]-3-cycloheptyl-acrylamide (E)-2-[3-chloro-4-(5-methyl-tetrazol-1-yl)-phenyl]-3-cyclopentyl-N-thiazol-2-yl-acrylamide (E)-3-cyclopentyl-2-[3-fluoro-4-(5-methyl-tetrazol-1-yl)-phenyl]-N-thiazol-2-yl-acrylamide This invention will be better understood from the following examples, which are for purposes of illustration and are not intended to limit the invention defined in the claims that follow thereafter.

EXAMPLE 1

2-[4-[(5-methyl)-1-tetrazolyl]-3-fluoro phenyl]-3-cyclopentyl N-thiazol-2-yl propionamide

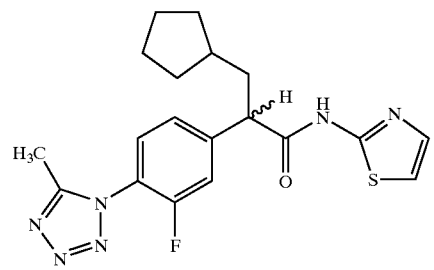

A solution of 2-fluoro-4-iodoaniline (4.74 g, 20 mmol) in dry tetrahydrofuran (20 mL) was cooled to 0° C. and then treated with acetic anhydride (8.2 g, 80 mmol). The reaction mixture was stirred for 10 min at 0° C. and then was allowed to warm to 25° C. where it was stirred for 2 h. After this time, thin layer chromatography analysis of the reaction mixture indicated the absence of starting material. The reaction mixture was then concentrated in vacuo to afford a crude residue. The residue precipitated from diethyl ether (50 mL) and hexanes (50 mL). The solid was collected by filtration and washed with hexanes to afford N-(2-fluoro-4-iodo-phenyl)-acetamide (5.12 g, 92%) as a white crystalline solid: mp 152–154° C.; EI-HRMS m/e calcd for $C_8H_7FINO$ ($M^+$) 278.9556, found 278.9559.

A suspension of N-(2-fluoro-4-iodo-phenyl)-acetamide (5 g, 18.24 mmol) in acetonitrile (100 mL) was cooled to 0° C. and then treated with sodium azide (3.56 g, 54.7 mmol). The reaction mixture was then treated with trifluoromethane-sulfonic anhydride (13.6 g, 48 mmol). The resulting reaction mixture was allowed to warm to 25° C. where it was stirred overnight, at which time, thin layer chromatography analysis of the reaction mixture indicated the absence of starting material. The reaction mixture was then concentrated in vacuo. The resulting residue was diluted with ethyl acetate (100 mL) and water (100 mL). The two layers were separated, and the aqueous layer was extracted with ethyl acetate (1×50 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 4/1 hexanes/ethyl acetate) afforded 1-(2-fluoro-4-iodo-phenyl)-5-methyl-1H-tetrazole (3.45 g, 62%) as a white solid: mp 122–124° C.; EI-HRMS m/e calcd for $C_8H_6FIN_4$ ($M^+$) 303.9621, found 303.9615.

A mixture of zinc dust (650 mg, 10 mmol, Aldrich, −325 mesh) and dry tetrahydrofuran (1 mL) under argon was treated with 1,2-dibromoethane (187 mg, 1 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (108 mg, 1 mmol), and the suspension was stirred for 15 min at 25° C. The reaction mixture was then treated dropwise with a solution of (E)-3-cyclopentyl-2-iodo-acrylic acid methyl ester (prepared in Example 7, 2.21 g, 7.5 mmol) in dry tetrahydrofuran (3 mL) over 3 min. The resulting reaction mixture was then stirred at 40–45° C. for 1 h and then stirred overnight at 25° C. The reaction mixture was then diluted with dry tetrahydrofuran (5 mL), and the stirring was stopped to allow the excess zinc dust to settle down (~2 h). In a separate reaction flask, bis(dibenzylideneacetone)palladium(0) (90 mg, 0.16 mmol) and triphenylphosphine (160 mg, 0.6 mmol) in dry tetrahydrofuran (10 mL) was stirred at 25° C. under argon for 10 min and then treated with 1-(2-fluoro-4-iodo-phenyl)-5-methyl-1H-tetrazole (1.52 g, 5 mmol) and the freshly prepared zinc compound in tetrahydrofuran. The resulting brick red solution was stirred at 25° C. over the weekend and then heated at 40–45° C. for 4 h. The reaction mixture was cooled to 25° C. and then poured into a saturated aqueous ammonium chloride solution (50 mL), and the organic compound was extracted into ethyl acetate (3×50 mL). The combined organic extracts were washed with a saturated aqueous sodium chloride solution (1×100 mL), dried over anhydrous magnesium sulfate, filtered, and concentrated in vacuo. Flash chromatography (Merck Silica gel 60, 230–400 mesh, 4/1 to 1/1 hexanes/ethyl acetate) afforded (E)-3-cyclopentyl-2-[3-fluoro-4-(5-methyl-tetrazol-1-yl)-phenyl]-acrylic acid methyl ester (1.14 g, 68%) as a light yellow solid: mp 111–114° C.; EI-HRMS m/e calcd for $C_{17}H_{19}FN_4O_2$ ($M^+$) 330.1492, found 330.1493.

A solution of nickel (II) chloride hexahydrate (115 mg, 0.24 mmol) and (E)-3-cyclopentyl-2-[3-fluoro-4-(5-methyl-tetrazol-1-yl)-phenyl]-acrylic acid methyl ester (400 mg, 1.21 mmol) in methanol (10 mL) was cooled to 0° C. and then treated with sodium borohydride (275 mg, 3.63 mmol) in two portions. After the addition, the black reaction mixture was stirred for 15 min at 0° C. and then allowed to warm to 25° C. where it was stirred for 15 h. The reaction mixture was concentrated in vacuo, and the residue was diluted with a 3N aqueous hydrochloric acid solution (30 mL) and ethyl acetate (50 mL). The two layers were separated. The organic layer was washed with a saturated aqueous sodium chloride solution (1×50 mL), dried over anhydrous magnesium sulfate, filtered, and concentrated in vacuo to afford racemic 3-cyclopentyl-2-[3-fluoro-4-(5-methyl-tetrazol-1-yl)-phenyl]-propionic acid methyl ester (400 mg, 99%) as a viscous oil: EI-HRMS m/e calcd for $C_{17}H_{21}FN_4O_2$ ($M^+$) 332.1648, found 332.1645.

A solution of 3-cyclopentyl-2-[3-fluoro-4-(5-methyl-tetrazol-1-yl)-phenyl]-propionic acid methyl ester (400 mg, 1.2 mmol) in ethanol (8 mL) was treated with a 1N aqueous sodium hydroxide solution (2.5 mL). The solution was heated at 45–50° C. for 5 h, at which time, thin layer chromatography analysis of the reaction mixture indicated the absence of starting material. The reaction mixture was concentrated in vacuo to remove ethanol. The residue was diluted with water (40 mL) and extracted with diethyl ether (1×50 mL) to remove any neutral impurities. The aqueous layer was then acidified with a 1N aqueous hydrochloric acid solution, and the resulting acid was extracted into ethyl acetate (2×50 mL). The combined organic layers were washed with a saturated aqueous sodium chloride solution (1×50 mL), dried over anhydrous magnesium sulfate, filtered, and concentrated in vacuo to afford 3-cyclopentyl-2-[3-fluoro-4-(5-methyl-tetrazol-1-yl)-phenyl]-propionic acid (360 mg, 94%) as a yellow solid: EI-HRMS m/e calcd for $C_{16}H_{19}FN_4O_2$ ($M^+$) 318.1487, found 318.1492.

A solution of triphenylphosphine (288 mg, 1.1 mmol) in methylene chloride (6 mL) was cooled to 0° C. and then treated with N-bromosuccinimide (196 mg, 1.1 mmol). The reaction mixture was stirred at 0° C. for 30 min and then treated with 3-cyclopentyl-2-[3-fluoro-4-(5-methyl-tetrazol-1-yl)-phenyl]-propionic acid (175 mg, 0.55 mmol). The clear solution was stirred for 15 min at 0° C. and then allowed to warm to 25° C. where it was stirred for 1.5 h. The reaction mixture was then treated with 2-aminothiazole (275 mg, 2.75 mmol), and the resulting suspension was stirred for 2 d at 25° C. The reaction mixture was then concentrated in vacuo to remove methylene chloride, and the residue was diluted with ethyl acetate (50 mL) and a 1N aqueous hydrochloric acid solution (25 mL). The two layers were separated, and the aqueous layer was extracted with ethyl acetate (1×25 mL). The combined organic extracts were successively washed with a 1N aqueous hydrochloric acid solution (1×50 mL), a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40S, Silica, 2/1 hexanes/ethyl acetate) afforded 3-cyclopentyl-2-[3-fluoro-4-(5-methyl-tetrazol-1-yl)-phenyl]-N-thiazol-2-yl-propionamide (80 mg, 36%) as an amorphous white solid: EI-HRMS m/e calcd for $C_{19}H_{21}FN_6OS$ ($M^+$) 400.1482, found 400.1476.

EXAMPLE 2

N-(5-Bromo-pyridin-2-yl)-3-cyclopentyl-2-[3-fluoro-4-(5-methyl-tetrazol-1-yl)-phenyl]-propionamide

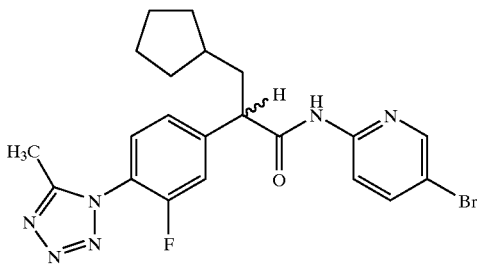

A solution of triphenylphosphine (288 mg, 1.1 mmol) in methylene chloride (6 mL) was cooled to 0° C. and then treated with N-bromosuccinimide (196 mg, 1.1 mmol). The reaction mixture was stirred at 0° C. for 30 min and then treated with 3-cyclopentyl-2-[3-fluoro-4-(5-methyl-tetrazol-1-yl)-phenyl]-propionic acid (prepared in Example 1, 175 mg, 0.55 mmol). The clear solution was stirred for 15 min at 0° C. and then allowed to warm to 25° C. where it was stirred for 1.5 h. The reaction mixture was then treated with 2-amino-5-bromopyridine (476 mg, 2.75 mmol), and the resulting suspension was stirred for 2 d at 25° C. The reaction mixture was then concentrated in vacuo to remove methylene chloride, and the residue was diluted with ethyl acetate (50 mL) and water (50 mL). The two layers were separated, and the aqueous layer was extracted with ethyl acetate (1×25 mL). The combined organic extracts were successively washed with a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40S, Silica, 2/1 hexanes/ethyl acetate) afforded N-(5-bromo-pyridin-2-yl)-3-cyclopentyl-2-[3-fluoro-4-(5-methyl-tetrazol-1-yl)-phenyl]-propionamide (190 mg, 73%) as a white solid: mp 73–78° C.; EI-HRMS m/e calcd for $C_{21}H_{22}BrFN_6O$ (M$^+$) 472.1022, found 472.1022.

EXAMPLE 3

2-[3-Chloro-4-(5-methyl-tetrazol-1-yl)-phenyl]-3-cyclopentyl-N-thiazol-2-yl-propionamide

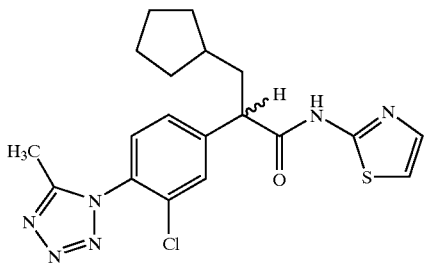

A mixture of zinc dust (650 mg, 10 mmol, Aldrich, −325 mesh) and dry tetrahydrofuran (1 mL) under argon was treated with 1,2-dibromoethane (187 mg, 1 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (108 mg, 1 mmol), and the suspension was stirred for 15 min at 25° C. The reaction mixture was then treated dropwise with a solution of (E)-3-cyclopentyl-2-iodo-acrylic acid methyl ester (prepared in Example 7, 1.26 g, 4.5 mmol) in dry tetrahydrofuran (2 mL) over 3 min. The reaction mixture was then stirred at 40–45° C. for 1 h and then stirred overnight at 25° C. The reaction mixture was then diluted with dry tetrahydrofuran (3 mL), and the stirring was stopped to allow the excess zinc dust to settle down (~2 h). In a separate reaction flask, bis (dibenzylideneacetone)palladium(0) (54 mg, 0.1 mmol) and triphenylphosphine (104 mg, 0.4 mmol) in dry tetrahydrofuran (4 mL) was stirred at 25° C. under argon for 10 min and then treated with 1-(2-chloro-4-iodo-phenyl)-5-methyl-1H-tetrazole (prepared in Example 4, 875 mg, 2.73 mmol) and the freshly prepared zinc compound in tetrahydrofuran. The resulting brick red solution was stirred at 25° C. over the weekend and then heated at 40–45° C. for 4 h. The reaction mixture was cooled to 25° C. and then poured into a saturated aqueous ammonium chloride solution (50 mL), and the organic compound was extracted into ethyl acetate (3×35 mL). The combined organic extracts were washed with a saturated aqueous sodium chloride solution (1×100 mL), dried over anhydrous magnesium sulfate, filtered, and concentrated in vacuo. Flash chromatography (Merck Silica gel 60, 230–400 mesh, 4/1 to 1/1 hexanes/ethyl acetate) afforded (E)-2-[3-chloro-4-(5-methyl-tetrazol-1-yl)-phenyl]-3-cyclopentyl-acrylic acid methyl ester (859 mg, 91%) as a light yellow semi-solid: EI-HRMS m/e calcd for $C_{17}H_{19}ClN_4O_2$ (M$^+$) 346.1196, found 346.1190.

A solution of nickel (II) chloride hexahydrate (180 mg, 0.8 mmol) and (E)-2-[3-chloro-4-(5-methyl-tetrazol-1-yl)-phenyl]-3-cyclopentyl-acrylic acid methyl ester (695 mg, 2.0 mmol) in methanol (15 mL) was cooled to 0° C. and then treated with sodium borohydride (454 mg, 12 mmol) in five portions. After the addition, the black reaction mixture was stirred for 15 min at 0° C. and then allowed to warm to 25° C. where it was stirred for 2 d. The reaction mixture was concentrated in vacuo, and the residue was diluted with a 3N aqueous hydrochloric acid solution (50 mL) and ethyl acetate (75 mL). The two layers were separated. The organic layer was washed with a saturated aqueous sodium chloride solution (1×50 mL), dried over anhydrous magnesium sulfate, filtered, and concentrated in vacuo to afford racemic 2-[3-chloro-4-(5-methyl-tetrazol-1-yl)-phenyl]-3-cyclopentyl-propionic acid methyl ester (815 mg, 99%) as a viscous oil: EI-HRMS m/e calcd for $C_{17}H_{21}ClN_4O_2$ (M$^+$) 348.1353, found 348.1359.

A solution of 2-[3-chloro-4-(5-methyl-tetrazol-1-yl)-phenyl]-3-cyclopentyl-propionic acid methyl ester ester (690 mg, 2.0 mmol) in ethanol (20 mL) was treated with a 1N aqueous sodium hydroxide solution (4 mL). The solution was heated at 45–50° C. for 3 h, at which time, thin layer chromatography analysis of the reaction mixture indicated the absence of starting material. The reaction mixture was concentrated in vacuo to remove ethanol. The residue was diluted with water (50 mL) and extracted with diethyl ether (1×60 mL) to remove any neutral impurities. The aqueous layer was then acidified with a 1N aqueous hydrochloric acid solution, and the resulting acid was extracted into ethyl acetate (2×50 mL). The combined organic layers were washed with a saturated aqueous sodium chloride solution (1×100 mL), dried over anhydrous magnesium sulfate, filtered, and concentrated in vacuo to afford 2-[3-chloro-4-(5-methyl-tetrazol-1-yl)-phenyl]-3-cyclopentyl-propionic acid (604 mg, 90%) as an amorphous white solid: EI-HRMS m/e calcd for $C_{16}H_{19}ClN_4O_2$ (M$^+$) 334.1196, found 334.1193.

A solution of triphenylphosphine (236 mg, 0.9 mmol) in methylene chloride (6 mL) was cooled to 0° C. and then treated with N-bromosuccinimide (160 mg, 0.9 mmol). The reaction mixture was stirred at 0° C. for 30 min and then treated with the 2-[3-chloro-4-(5-methyl-tetrazol-1-yl)-phenyl]-3-cyclopentyl-propionic acid (151 mg, 0.45 mmol). The clear solution was stirred for 15 min at 0° C. and then allowed to warm to 25° C. where it was stirred for 2 h. The reaction mixture was then treated with 2-aminothiazole (135 mg, 1.35 mmol), and the resulting suspension was stirred for 20 h at 25° C. The reaction mixture was then concentrated in vacuo to remove methylene chloride, and the residue was diluted with ethyl acetate (30 mL) and a 1N aqueous hydrochloric acid solution (30 mL). The two layers were separated, and the aqueous layer was extracted with ethyl acetate (1×20 mL). The combined organic extracts were successively washed with a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40S, Silica, 1/1 hexanes/ethyl acetate) afforded 2-[3-chloro-4-(5-methyl-tetrazol-1-yl)-phenyl]-3-cyclopentyl-N-thiazol-2-yl-propionamide (80 mg, 42%) as a white solid: mp 190–193° C.; EI-HRMS m/e calcd for $C_{19}H_{21}ClN_6OS$ (M$^+$) 416.1186, found 416.1183.

EXAMPLE 4

2-[3-Chloro-4-(5-methyl-tetrazol-1-yl)-phenyl]-3-cyclohexyl-N-thiazol-2-yl-propionamide

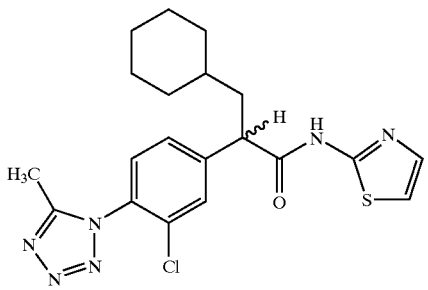

A mixture of zinc dust (16.34 g, 250 mmol, Aldrich, –325 mesh) and dry tetrahydrofuran (6 mL) under argon was treated with 1,2-dibromoethane (0.94 g, 5 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (0.54 g, 5 mmol), and the suspension was stirred for 15 min at 25° C. The reaction mixture was then treated dropwise with a solution of cyclohexyl iodide (21 g, 100 mmol) in dry tetrahydrofuran (30 mL) over 15 min. During the addition, the temperature rose to 60° C. The reaction mixture was then stirred for 3 h at 40–45° C. The reaction mixture was then cooled to 25° C. and diluted with dry tetrahydrofuran (60 mL). The stirring was stopped to allow the excess zinc dust to settle down (~3 h). In a separate reaction flask, a mixture of lithium chloride (8.48 g, 200 mmol, predried at 130° C. under high vacuum for 3 h) and copper cyanide (8.95 g, 100 mmol) in dry tetrahydrofuran (110 mL) was stirred for 10 min at 25° C. to obtain a clear solution. The reaction mixture was cooled to –70° C. and then slowly treated with the freshly prepared zinc solution using a syringe. After the addition, the reaction mixture was allowed to warm to 0° C. where it was stirred for 5 min. The reaction mixture was again cooled back to –70° C. and then slowly treated with methyl propiolate (7.56 g, 90 mmol). The resulting reaction mixture was stirred for 15 h at –70° C. to –50° C. and then slowly treated with a solution of iodine (34.26 g, 135 mmol) in dry tetrahydrofuran (30 mL), with the temperature kept at –70° C. to –60° C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (400 mL) and ammonium hydroxide (100 mL), and the organic compound was extracted into ethyl acetate (3×250 mL). The combined organic extracts were successively washed with a saturated aqueous sodium thiosulfate solution (1×500 mL) and a saturated aqueous sodium chloride solution (1×500 mL), dried over anhydrous magnesium sulfate, filtered, and concentrated in vacuo. Flash chromatography (Merck Silica gel 60, 230–400 mesh, 9/1 hexanes/diethyl ether) afforded (E)-3-cyclohexyl-2-iodo-acrylic acid methyl ester (26.3 g, 99%) as a light pink oil: EI-HRMS m/e calcd for $C_{10}H_{15}IO_2$ (M$^+$) 294.0117, found 294.0114.

A suspension of triphenylphospine (11.7 g, 44.8 mmol) in carbon tetrachloride (8 mL, 83 mmol) was cooled to 0° C. and then treated with triethylamine (2.5 mL, 18 mmol) and acetic acid (1.15 mL, 20 mmol). The reaction mixture was stirred at 0° C. for 10 min and then treated with a solution of 2-chloro-4-iodoaniline (5.07 g, 20 mmol) in carbon tetrachloride (12 mL, heated to obtain a solution). The resulting light brown suspension was allowed to warm to 25° C. and then it was refluxed overnight. The reaction mixture was cooled to 25° C. and then concentrated in vacuo. The resulting solid residue was then diluted with hexanes (50 mL) and methylene chloride (50 mL). The precipitated solid was collected by filtration and washed with hexanes. The filtrate was concentrated in vacuo, and the resulting residue was diluted with diethyl ether (100 mL). The precipitated solid was collected by filtration and washed with hexanes, and the filtrate was concentrated in vacuo. The resulting residue was again diluted with hexanes (100 mL), and the precipitated solid was collected by filtration. The filtrate was finally concentrated in vacuo to afford the imidoyl chloride intermediate (4.08 g) as a liquid. This crude imidoyl chloride intermediate (4.08 g, ~13 mmol) was treated with sodium azide (1.04 g, 16 mmol) and acetic acid (10 mL). The reaction was exothermic, and the resulting reaction mixture was stirred for 1 h at 25° C. The reaction mixture was then heated at 70° C. for 2 h, at which time, thin layer chromatography analysis of the reaction mixture indicated the absence of the imidoyl chloride intermediate. The cloudy yellow suspension was cooled to 25° C. and then diluted with water (100 mL) and extracted with ethyl acetate (2×75 mL). The combined organic extracts were washed successively with a saturated aqueous sodium bicarbonate solution (1×100 mL) and a saturated aqueous sodium chloride solution (1×100 mL), dried over anhydrous magnesium sulfate, filtered, and concentrated in vacuo. Biotage chromatography (FLASH 40M, Silica, 6/1 hexanes/diethyl ether) afforded 1-(2-chloro-4-iodo-phenyl)-5-methyl-1H-tetrazole (350 mg, 6%) as a white solid: mp 128–130.5° C.; EI-HRMS m/e calcd for $C_8H_6ClIN_4$ (M$^+$) 319.9327, found 319.9325.

A mixture of zinc dust (320 mg, 5 mmol, Aldrich, –325 mesh) and dry tetrahydrofuran (1 mL) under argon was treated with 1,2-dibromoethane (94 mg, 0.5 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (55 mg, 0.5 mmol), and the suspension was stirred for 15 min at 25° C. The reaction mixture was then treated dropwise with a solution of (E)-3-cyclohexyl-2-iodo-acrylic acid methyl ester (588 mg, 2 mmol) in dry tetrahydrofuran (2 mL). After the addition, the reaction mixture was stirred for 1 h at 40–45° C. and then stirred overnight at 25° C. The reaction mixture was then diluted with dry tetrahydrofuran (2 mL), and the stirring was stopped to allow the excess zinc dust to settle down (~2 h). In a separate reaction flask, bis(dibenzylideneacetone)-palladium(0) (27 mg, 0.05 mmol) and triphenylphosphine (57 mg, 0.2 mmol) in dry tetrahydrofuran (4 mL) was stirred at 25° C. under argon for 10 min and then treated with 1-(2-chloro-4-iodo-phenyl)-5-methyl-1H-tetrazole (320.5 mg, 1 mmol) and the freshly prepared zinc compound in tetrahydrofuran. The resulting brick red solution was heated at 50° C. for 15 h. The reaction mixture was cooled to 25° C. and then poured into a saturated aqueous ammonium chloride solution (30 mL), and the organic compound was extracted into ethyl acetate (3×20 mL). The combined organic extracts were washed with a saturated aqueous sodium chloride solution (1×50 mL), dried over anhydrous magnesium sulfate, filtered, and concentrated in vacuo. Biotage chromatography (FLASH 40S, Silica, 4/1/1 hexanes/ethyl acetate/methylene chloride) afforded (E)-2-[3-chloro-4-(5-methyl-tetrazol-1-yl)-phenyl]-3-cyclohexyl-acrylic acid methyl ester (233 mg, 64%) as an amorphous white solid: EI-HRMS m/e calcd for $C_{18}H_{21}ClN_4O_2$ (M$^+$) 360.1353, found 360.1354.

A solution of nickel (II) chloride hexahydrate (78 mg, 0.328 mmol) and (E)-2-[3-chloro-4-(5-methyl-tetrazol-1-yl)-phenyl]-3-cyclohexyl-acrylic acid methyl ester (295 mg, 0.82 mmol) in methanol (8 mL) was cooled to 0° C. and then treated with sodium borohydride (186 mg, 4.92 mmol) in four portions. After the addition, the black reaction mixture was stirred for 15 min at 0° C. and then allowed to warm to 25° C. where it was stirred for 24 h. The reaction mixture was then concentrated in vacuo, and the residue was diluted with water (30 mL) and ethyl acetate (50 mL). The two layers were separated. The organic layer was washed successively with a 3N aqueous hydrochloric acid solution (1×50 mL), a saturated aqueous sodium bicarbonate solution (1×50 mL) and a saturated aqueous sodium chloride solution (1×50 mL), dried over anhydrous magnesium sulfate, filtered, and concentrated in vacuo to afford racemic 2-[3-chloro-4-(5-methyl-tetrazol-1-yl)-phenyl]-3-cyclohexyl-propionic acid methyl ester (285 mg, 96%) as a viscous oil: EI-HRMS m/e calcd for $C_{18}H_{23}ClN_4O_2$ (M$^+$) 362.1509, found 362.1516.

A solution of 2-[3-chloro-4-(5-methyl-tetrazol-1-yl)-phenyl]-3-cyclohexyl-propionic acid methyl ester (278 mg, 0.76 mmol) in ethanol (6 mL) was treated with a 1N aqueous sodium hydroxide solution (1.5 mL). The solution was heated at 45–50° C. for 5 h, at which time, thin layer chromatography analysis of the mixture indicated the absence of starting material. The reaction mixture was then concentrated in vacuo to remove ethanol, and the residue was diluted with water (20 mL) and extracted with diethyl ether (1×40 mL) to remove any neutral impurities. The aqueous layer was acidified with a 1N aqueous hydrochloric acid solution. The resulting acid was extracted into ethyl acetate (2×50 mL). The combined organic layers were washed with a saturated aqueous sodium chloride solution (1×50 mL), dried over anhydrous magnesium sulfate, filtered, and concentrated in vacuo to afford 2-[3-chloro-4-(5-methyl-tetrazol-1-yl)-phenyl]-3-cyclohexyl-propionic acid (226 mg, 85%) as an amorphous solid: EI-HRMS m/e calcd for $C_{17}H_{21}ClN_4O_2$ (M$^+$) 348.1353, found 348.1354.

A solution of triphenylphosphine (281 mg, 1.07 mmol) in methylene chloride (5 mL) was cooled to 0° C. and then treated with N-bromosuccinimide (190.4 mg, 1.07 mmol). The reaction mixture was stirred at 0° C. for 30 min and then treated with a solution of 2-[3-chloro-4-(5-methyl-tetrazol-1-yl)-phenyl]-3-cyclohexyl-propionic acid (220 mg, 0.63 mmol) in methylene chloride (4 mL). The clear solution was stirred for 15 min at 0° C. and then allowed to warm to 25° C. where it was stirred for 2 h. The reaction mixture was then treated with 2-aminothiazole (189 mg, 1.89 mmol), and the resulting suspension was stirred for 15 h at 25° C. The reaction mixture was concentrated in vacuo to remove methylene chloride, and the residue was diluted with ethyl acetate (50 mL) and a 1N aqueous hydrochloric acid solution (50 mL). The two layers were separated, and the aqueous layer was extracted with ethyl acetate (1×30 mL). The combined organic extracts were successively washed with a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40S, Silica, 4/1 hexanes/ethyl acetate) afforded 2-[3-chloro-4-(5-methyl-tetrazol-1-yl)-phenyl]-3-cyclohexyl-N-thiazol-2-yl-propionamide (79 mg, 29%) as an amorphous solid: EI-HRMS m/e calcd for $C_{20}H_{23}ClN_6OS$ (M$^+$) 430.1343, found 430.1343.

EXAMPLE 5

N-(5-Bromo-pyridin-2-yl)-3-cyclopentyl-2-[3-chloro-4-(5-methyl-tetrazol-1-yl)-phenyl]-propionamide

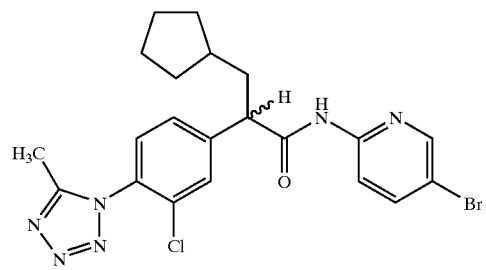

A solution of triphenylphosphine (236 mg, 0.9 mmol) in methylene chloride (6 mL) was cooled to 0° C. and then treated with N-bromosuccinimide (160 mg, 0.9 mmol). The reaction mixture was stirred at 0° C. for 30 min and then treated with the 2-[3-chloro-4-(5-methyl-tetrazol-1-yl)-phenyl]-3-cyclopentyl-propionic acid (prepared in Example 3, 151 mg, 0.45 mmol). The clear solution was stirred for 15 min at 0° C. and then allowed to warm to 25° C. where it was stirred for 2 h. The reaction mixture was then treated with 2-amino–5-bromopyridine (234 mg, 1.35 mmol), and the resulting suspension was stirred for 2 d at 25° C. The reaction mixture was then concentrated in vacuo to remove methylene chloride, and the residue was diluted with ethyl acetate (30 mL) and water (30 mL). The two layers were separated, and the aqueous layer was extracted with ethyl acetate (1×20 mL). The combined organic extracts were successively washed with a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40S, Silica, 2/1 hexanes/ethyl acetate) afforded N-(5-bromo-pyridin-2-yl)-2-[3-chloro-4-(5-methyl-tetrazol-1-yl)-phenyl]-3-cyclopentyl-propionamide (90 mg, 42%) as an amorphous white solid: EI-HRMS m/e calcd for $C_{21}H_{22}BrClN_6O$ (M$^+$) 489.0727, found 489.0727.

EXAMPLE 6

2-[3-Chloro-4-(5-trifluoromethyl-tetrazol-1-yl)-phenyl]-3-cyclohexyl-N-thiazol-2-yl-propionamide

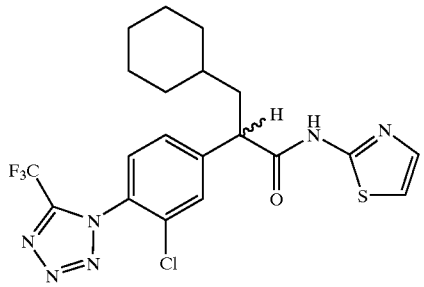

A suspension of triphenylphospine (13.11 g, 50 mmol) in carbon tetrachloride (8 mL, 83 mmol) was cooled to 0° C. and then treated with triethylamine (2.78 mL, 20 mmol) and trifluoroacetic acid (1.3 mL, 16.6 mmol). The reaction mixture was stirred at 0° C. for 10 min and then treated with a solution of 2-chloro-4-iodoaniline (5.07 g, 20 mmol) in carbon tetrachloride (10 mL). The resulting light brown suspension was allowed to warm to 25° C. and then it was refluxed overnight. The reaction mixture was cooled to 25° C. and then concentrated in vacuo. The resulting solid residue was then diluted with hexanes (50 mL) and methylene chloride (50 mL). The precipitated solid was collected by filtration and washed with hexanes. The filtrate was concentrated in vacuo, and the resulting residue was diluted with diethyl ether (100 mL). The precipitated solid was collected by filtration and washed with hexanes, and the filtrate was concentrated in vacuo. The resulting residue was again diluted with hexanes (100 mL), and the precipitated solid was collected by filtration. The filtrate was finally concentrated in vacuo to afford the imidoyl chloride intermediate (5.88 g) as a brown liquid. This crude imidoyl chloride intermediate (5.88 g, ~16 mmol) was treated with sodium azide (1.04 g, 16 mmol) and acetic acid (10 mL). The resulting reaction mixture was then heated at 70° C. for 2 h, at which time, thin layer chromatography analysis of the reaction mixture indicated the absence of the imidoyl chloride intermediate. The cloudy yellow suspension was cooled to 25° C. and then diluted with water (100 mL) and extracted with ethyl acetate (2×75 mL). The combined organic extracts were washed successively with a saturated aqueous sodium bicarbonate solution (1×100 mL) and a saturated aqueous sodium chloride solution (1×100 mL), dried over anhydrous magnesium sulfate, filtered, and concentrated in vacuo. Biotage chromatography (FLASH 40M, Silica, 8/1 hexanes/diethyl ether) afforded 1-(2-chloro-4-iodo-phenyl)-5-trifluoromethyl-1H-tetrazole (5.2 g, 69%) as a light yellow solid: mp 71–73° C.; EI-HRMS m/e calcd for $C_8H_3ClF_3IN_4$ (M$^+$) 373.9043, found 373.9044.

A mixture of zinc dust (650 mg, 10 mmol, Aldrich, –325 mesh) and dry tetrahydrofuran (2 mL) under argon was treated with 1,2-dibromoethane (187 mg, 1 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (110 mg, 1 mmol), and the suspension was stirred for 15 min at 25° C. The reaction mixture was then treated dropwise with a solution of (E)-3-cyclohexyl-2-iodo-acrylic acid methyl ester (prepared in Example 4, 1.32 g, 4.5 mmol) in dry tetrahydrofuran (2 mL) over 5 min. After the addition, the reaction mixture was stirred for 1 h at 40–45° C. and then stirred overnight at 25° C. The reaction mixture was then diluted with dry tetrahydrofuran (4 mL), and the stirring was stopped to allow the excess zinc dust to settle down (~2 h). In a separate reaction flask, bis(dibenzylideneacetone)palladium(0) (54 mg, 0.1 mmol) and triphenylphosphine (104 mg, 0.4 mmol) in dry tetrahydrofuran (8 mL) was stirred at 25° C. under argon for 10 min and then treated with 1-(2-chloro-4-iodo-phenyl)-5-trifluoromethyl-1H-tetrazole (1.12 g, 3 mmol) and the freshly prepared zinc compound in tetrahydrofuran. The resulting brick red solution was heated at 50° C. for 15 h. The reaction mixture was cooled to 25° C. and then poured into a saturated aqueous ammonium chloride solution (70 mL), and the organic compound was extracted into ethyl acetate (3×50 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 6/1 hexanes/ethyl acetate) afforded (E)-2-[3-chloro-4-(5-trifluoromethyl-tetrazol-1-yl)-phenyl]-3-cyclohexyl-acrylic acid methyl ester (908 mg, 73%) as an amorphous white solid: EI-HRMS m/e calcd for $C_{18}H_{18}ClF_3N_4O_2$ (M$^+$) 414.1070, found 414.1075.

A solution of nickel (II) chloride hexahydrate (77 mg, 0.324 mmol) and (E)-2-[3-chloro-4-(5-trifluoromethyl-tetrazol-1-yl)-phenyl]-3-cyclohexyl-acrylic acid methyl ester (674 mg, 1.62 mmol) in methanol (15 mL) was cooled to 0° C. and then treated with sodium borohydride (184 mg, 4.86 mmol) in four portions. After the addition, the black reaction mixture was stirred for 15 min at 0° C. and then allowed to warm to 25° C. where it was stirred for 20 h. The reaction mixture was then concentrated in vacuo, and the residue was diluted with water (50 mL) and ethyl acetate (100 mL). The two layers were separated. The organic layer was washed successively with a 3N aqueous hydrochloric acid solution (1×50 mL), a saturated aqueous sodium bicarbonate solution (1×50 mL) and a saturated aqueous sodium chloride solution (1×50 mL), dried over anhydrous magnesium sulfate, filtered, and concentrated in vacuo to afford racemic 2-[3-chloro-4-(5-trifluoromethyl-tetrazol-1-yl)-phenyl]-3-cyclohexyl-propionic acid methyl ester (640 mg, 95%) as a viscous oil: EI-HRMS m/e calcd for $C_{18}H_{20}ClF_3N_4O_2$ (M$^+$) 416.1527, found 416.1529.

A solution of 2-[3-chloro-4-(5-trifluoromethyl-tetrazol-1-yl)-phenyl]-3-cyclohexyl-propionic acid methyl ester (634 mg, 1.52 mmol) in ethanol (10 mL) was treated with a 1N aqueous sodium hydroxide solution (3 mL). The solution was heated at 45–50° C. for 5 h, at which time, thin layer chromatography analysis of the mixture indicated the absence of starting material. The reaction mixture was then concentrated in vacuo to remove ethanol, and the residue was diluted with water (50 mL) and extracted with diethyl ether (1×60 mL) to remove any neutral impurities. The aqueous layer was acidified with a 1N aqueous hydrochloric acid solution. The resulting acid was extracted into ethyl acetate (2×50 mL). The combined organic layers were washed with a saturated aqueous sodium chloride solution (1×100 mL), dried over anhydrous magnesium sulfate, filtered, and concentrated in vacuo to afford 2-[3-chloro-4-(5-trifluoromethyl-tetrazol-1-yl)-phenyl]-3-cyclohexyl-propionic acid (375 mg, 61%) as a viscous oil: EI-HRMS m/e calcd for $C_{17}H_{18}ClF_3N_4O_2$ (M+) 402.1070, found 402.1067.

A solution of triphenylphosphine (409 mg, 1.56 mmol) in methylene chloride (8 mL) was cooled to 0° C. and then treated with N-bromosuccinimide (277 mg, 1.56 mmol). The reaction mixture was stirred at 0° C. for 30 min and then treated with a solution of 2-[3-chloro-4-(5-trifluoromethyl-tetrazol-1-yl)-phenyl]-3-cyclohexyl-propionic acid (370 mg, 0.92 mmol) in methylene chloride (5 mL). The clear solution was stirred for 15 min at 0° C. and then allowed to warm to 25° C. where it was stirred for 2 h. The reaction mixture was then treated with 2-aminothiazole (276 mg, 2.76 mmol), and the resulting suspension was stirred for 15 h at 25° C. The reaction mixture was concentrated in vacuo to remove methylene chloride, and the residue was diluted with ethyl acetate (100 mL) and a 1N aqueous hydrochloric acid solution (50 mL). The two layers were separated, and the aqueous layer was extracted with ethyl acetate (1×50 mL). The combined organic extracts were successively washed with a saturated aqueous sodium bicarbonate solution (1×100 mL) and a saturated aqueous sodium chloride solution (1×100 mL), dried over anhydrous magnesium sulfate, filtered, and concentrated in vacuo. Biotage chromatography (FLASH 40S, Silica, 3/2 hexanes/ethyl acetate) afforded 2-[3-chloro-4-(5-trifluoromethyl-tetrazol-1-yl)-phenyl]-3-cyclohexyl-N-thiazol-2-yl-propionamide (83 mg, 18%) as an amorphous solid: EI-HRMS m/e calcd for $C_{20}H_{20}ClF_3N_6OS$ (M+) 484.1060, found 484.1068.

EXAMPLE 7

3-Cyclopentyl-2-[4-(5-methyl-tetrazol-1-yl)-3-trifluoromethyl-phenyl]-N-thiazol-2-yl-propionamide

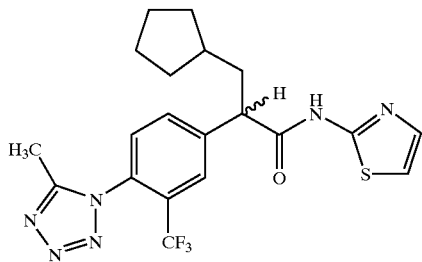

A solution of 2-(trifluoromethyl)-4-bromoaniline (4.8 g, 20 mmol) in dry tetrahydrofuran (20 mL) was cooled to 0° C. and then treated with acetic anhydride (8.2 g, 80 mmol). The reaction mixture was stirred at 0° C. for 10 min and then allowed to warm to 25° C. The reaction mixture was stirred at 25° C. for 2 h, at which time, thin layer chromatography analysis of the reaction mixture indicated the absence of starting material. The reaction mixture was then concentrated in vacuo. The crude residue precipitated from diethyl ether (50 mL) and hexanes (50 mL). The solid was collected by filtration and washed with hexanes to afford N-(4-bromo-2-trifluoromethyl-phenyl)-acetamide (5.07 g, 90%) as an amorphous white solid: EI-HRMS m/e calcd for $C_9H_7BrF_3NO$ (M+) 281.8352, found 281.8348.

A suspension of N-(4-bromo-2-trifluoromethyl-phenyl)-acetamide (2.41 g, 8.54 mmol) in acetonitrile (40 mL) was treated with methylene chloride (5 mL) to obtain a clear solution at 25° C. The resulting solution was treated with sodium azide (1.24 g, 19.1 mmol), and the reaction mixture was then cooled to 0° C. The reaction mixture was then treated with trifluoromethanesulfonic anhydride (3.59 g, 12.7 mmol). The resulting reaction mixture was allowed to warm to 25° C. where it was stirred overnight, at which time, thin layer chromatography analysis of the reaction mixture indicated the absence of starting material. The reaction mixture was then concentrated in vacuo. The resulting residue was diluted with ethyl acetate (50 mL) and water (50 mL). The two layers were separated, and the aqueous layer was extracted with ethyl acetate (1×30 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 2/1 hexanes/ethyl acetate) afforded 1-(4-bromo-2-trifluoromethyl-phenyl)-5-methyl-1H-tetrazole (1.85 g, 70%) as a white solid: EI-HRMS m/e calcd for $C_9H_6BrF_3N_4$ (M+) 305.9728, found 305.9733.

A mixture of lithium chloride (8.48 g, 200 mmol, predried at 130° C. under high vacuum for 3 h) and copper cyanide (8.96 g, 100 mmol) in dry tetrahydrofuran (100 mL) was stirred at 25° C. under argon for 10 min to obtain a clear solution. The reaction mixture was then cooled to −70° C. and then slowly treated with a 2.0M solution of cyclopentylmagnesium chloride in diethyl ether (55 mL, 110 mmol). After the addition, the reaction mixture was allowed to warm to −30° C. where it was stirred for 5 min. The resulting reaction mixture was again cooled back to −70° C. and then slowly treated with methyl propiolate (7.99 g, 95 mmol). The reaction mixture was stirred overnight at −60° C. to −50° C. The reaction mixture was then slowly treated with a solution of iodine (34.3 g, 135 mmol) in dry tetrahydrofuran (30 mL), with the temperature kept at −70° C. to −60° C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (200 mL) and ammonium hydroxide (50 mL), and the organic compound was extracted into diethyl ether (3×100 mL). The combined organic extracts were successively washed with a saturated aqueous sodium thiosulfate solution (1×300 mL) and a saturated aqueous sodium chloride solution (1×300 mL). The organic layer was then dried over anhydrous magnesium sulfate, filtered, and concentrated in vacuo. Flash chromatography (Merck Silica gel 60, 230–400 mesh, 20/1 hexanes/diethyl ether) afforded (E)-3-cyclopentyl-2-iodo-acrylic acid methyl ester (25.8 g, 97%) as a yellow oil: EI-HRMS m/e calcd for $C_9H_{13}IO_2$ (M+) 279.9960, found 279.9961.

A mixture of zinc dust (710 mg, 11 mmol, Aldrich, −325 mesh) and dry tetrahydrofuran (1 mL) under argon was treated with 1,2-dibromoethane (187 mg, 1 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (108 mg, 1 mmol), and the suspension was stirred for 15 min at 25° C. The reaction mixture was then treated dropwise with a solution of (E)-3-cyclopentyl-2-iodo-acrylic acid methyl ester (1.54 g, 5.5 mmol) in dry tetrahydrofuran (2 mL) over 3 min. The reaction mixture was then stirred at 40–45° C. for 1 h and then stirred overnight at 25° C. The reaction mixture was then diluted with dry tetrahydrofuran (4 mL), and the stirring was stopped to allow the excess zinc dust to settle down (~2 h). In a separate reaction flask, bis(dibenzylideneacetone) palladium(0) (81 mg, 0.15 mmol) and triphenylphosphine (156 mg, 0.6 mmol) in dry tetrahydrofuran (6 mL) was stirred at 25° C. under argon for 10 min and then treated with 1-(4-bromo-2-trifluoromethyl-phenyl)-5-methyl-1H-tetrazole (1.05 g, 3.5 mmol) and the freshly prepared zinc compound in tetrahydrofuran. The resulting brick red solution was heated at 40–45° C. over the weekend. The reaction mixture was cooled to 25° C. and then poured into a saturated aqueous ammonium chloride solution (50 mL), and the organic compound was extracted into ethyl acetate (3×35 mL). The combined organic extracts were washed with a saturated aqueous sodium chloride solution (1×100 mL), dried over anhydrous magnesium sulfate, filtered, and concentrated in vacuo. Flash chromatography (Merck Silica gel 60, 230–400 mesh, 4/1 to 1/1 hexanes/ethyl acetate) afforded (E)-3-cyclopentyl-2-[4-(5-methyl-tetrazol-1-yl)-3-trifluoromethyl-phenyl]-acrylic acid methyl ester (1.03 g, 77.6%) as a light yellow solid: EI-HRMS m/e calcd for $C_{18}H_{19}F_3N_4O_2$ (M+) 380.1460, found 380.1453.

A solution of nickel (II) chloride hexahydrate (102 mg, 0.428 mmol) and (E)-3-cyclopentyl-2-[4-(5-methyl-tetrazol-1-yl)-3-trifluoromethyl-phenyl]-acrylic acid methyl ester (814 mg, 2.14 mmol) in methanol (20 mL) was cooled to 0° C. and then treated with sodium borohydride (265 mg, 7 mmol) in five portions. After the addition, the black reaction mixture was stirred for 15 min at 0° C. and then allowed to warm to 25° C. where it was stirred for 15 h. The reaction mixture was concentrated in vacuo, and the residue was diluted with a 3N aqueous hydrochloric acid solution (50 mL) and ethyl acetate (75 mL). The two layers were separated. The organic layer was washed with a saturated aqueous sodium chloride solution (1×50 mL), dried over anhydrous magnesium sulfate, filtered, and concentrated in vacuo to afford racemic 3-cyclopentyl-2-[4-(5-methyl-tetrazol-1-yl)-3-trifluoromethyl-phenyl]-propionic acid methyl ester (815 mg, 99%) as a viscous oil: EI-HRMS m/e calcd for $C_{18}H_{21}F_3N_4O_2$ (M+) 382.1617, found 382.1617.

A solution of 3-cyclopentyl-2-[4-(5-methyl-tetrazol-1-yl)-3-trifluoromethyl-phenyl]-propionic acid methyl ester (870 mg, 2.27 mmol) in ethanol (12 mL) was treated with a 1N aqueous sodium hydroxide solution (8 mL). The solution was heated at 45–50° C. for 3 h, at which time, thin layer chromatography analysis of the reaction mixture indicated the absence of starting material. The reaction mixture was concentrated in vacuo to remove ethanol. The residue was diluted with water (50 mL) and extracted with diethyl ether (1×60 mL) to remove any neutral impurities. The aqueous layer was then acidified with a 1N aqueous hydrochloric acid solution, and the resulting acid was extracted into ethyl acetate (2×50 mL). The combined organic layers were washed with a saturated aqueous sodium chloride solution (1×100 mL), dried over anhydrous magnesium sulfate, filtered, and concentrated in vacuo to afford 3-cyclopentyl-2-[4-(5-methyl-tetrazol-1-yl)-3-trifluoromethyl-phenyl]-propionic acid (781 mg, 93%) as a white solid: EI-HRMS m/e calcd for $C_{17}H_{19}F_3N_4O_2$ (M+) 368.1460, found 368.1460.

A solution of triphenylphosphine (213 mg, 0.84 mmol) in methylene chloride (12 mL) was cooled to 0° C. and then treated with N-bromosuccinimide (144 mg, 0.84 mmol). The reaction mixture was stirred at 0° C. for 30 min and then treated with the 3-cyclopentyl-2-[4-(5-methyl-tetrazol-1-yl)-3-trifluoromethyl-phenyl]-propionic acid (150 mg, 0.4 mmol). The clear solution was stirred for 15 min at 0° C. and then allowed to warm to 25° C. where it was stirred for 2 h. The reaction mixture was then treated with 2-aminothiazole (122 mg, 1.22 mmol), and the resulting suspension was stirred for 15 h at 25° C. The reaction mixture was then concentrated in vacuo to remove methylene chloride, and the residue was diluted with ethyl acetate (30 mL) and a 1N aqueous hydrochloric acid solution (30 mL). The two layers were separated, and the aqueous layer was extracted with ethyl acetate (1×20 mL). The combined organic extracts were successively washed with a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40S, Silica, 1/2 hexanes/ethyl acetate) afforded 3-cyclopentyl-2-[4-(5-methyl-tetrazol-1-yl)-3-trifluoromethyl-phenyl]-N-thiazol-2-yl-propionamide (128 mg, 70%) as an amorphous solid: EI-HRMS m/e calcd for $C_{20}H_{21}F_3N_6OS$ (M+) 450.1449, found 450.1454.

EXAMPLE 8

N-(5-Bromo-pyridin-2-yl)-3-cyclopentyl-2-[4-(5-methyl-tetrazol-1-yl)-3-trifluoromethyl-phenyl]-propionamide

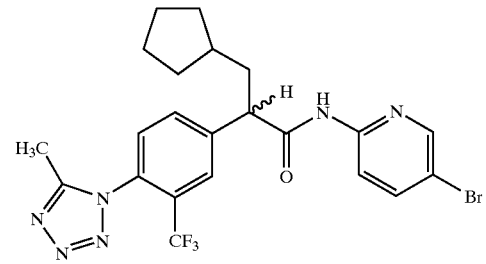

A solution of triphenylphosphine (213 mg, 0.84 mmol) in methylene chloride (12 mL) was cooled to 0° C. and then treated with N-bromosuccinimide (144 mg, 0.84 mmol). The reaction mixture was stirred at 0° C. for 30 min and then treated with the 3-cyclopentyl-2-[4-(5-methyl-tetrazol-1-yl)-3-trifluoromethyl-phenyl]-propionic acid (prepared in Example 7, 150 mg, 0.4 mmol). The clear solution was stirred for 15 min at 0° C. and then allowed to warm to 25° C. where it was stirred for 2 h. The reaction mixture was then treated with 2-amino-5-bromopyridine (122 mg, 1.22 mmol), and the resulting suspension was stirred for 15 h at 25° C. The reaction mixture was then concentrated in vacuo to remove methylene chloride, and the residue was diluted with ethyl acetate (30 mL) and water (30 mL). The two layers were separated, and the aqueous layer was extracted with ethyl acetate (1×20 mL). The combined organic extracts were successively washed with a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40S, Silica, 1/1 hexanes/ethyl acetate) afforded N-(5-bromo-pyridin-2-yl)-3-cyclopentyl-2-[4-(5-methyl-tetrazol-1-yl)-3-trifluoromethyl-phenyl]-propionamide (90 mg, 42%) as an amorphous white solid: EI-HRMS m/e calcd for $C_{22}H_{22}BrF_3N_6O$ (M+) 522.0991, found 522.0989.

EXAMPLE 9

3-Cyclopentyl-2-[4-methanesulfonyl-3-(5-methyl-tetrazol-1-yl)-phenyl]-N-thiazol-2-yl-propionamide

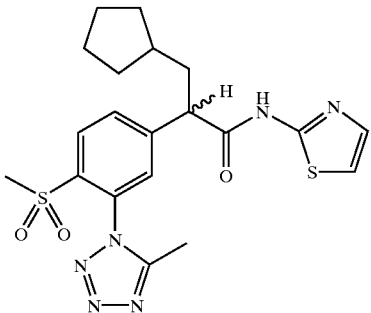

A solution of isoamyl nitrite (10.05 mL, 75 mmol) in dimethyl disulfide (49.5 mL, 550 mmol) at 25° C. was slowly treated with 4-bromo-2-nitroaniline (10.85 g, 50 mmol). The reaction was exothermic with gas evolution. The resulting brown reaction mixture was heated to 80–90° C. for 2 h, at which time, thin layer chromatography analysis of the reaction mixture indicated the absence of starting material. The reaction mixture was cooled to 25° C. and then concentrated in vacuo. The resulting residue was dissolved in ethyl acetate (300 mL). The organic layer was washed successively with a 1N aqueous hydrochloric acid solution (1×300 mL) and a saturated aqueous sodium chloride solution (1×300 mL), dried over anhydrous magnesium sulfate, filtered, and concentrated in vacuo. Biotage chromatography (FLASH 40M, Silica, 6/1 to 5/1 hexanes/ethyl acetate) afforded 4-bromo-1-methylsulfanyl-2-nitro-benzene (12.05 g, 97%) as a brown solid: EI-IRMS m/e calcd for $C_7H_6BrNO_2S$ ($M^+$) 246.9372, found 246.9368.

A solution of 4-bromo-1-methylsulfanyl-2-nitro-benzene (12.05 g, 48.6 mmol) in methylene chloride (300 mL) was cooled to −10° C. and then treated with 3-chloroperoxybenzoic acid (86% grade, 25.2 g, 145.8 mmol). The reaction mixture was stirred at −10° C. for 10 min and then allowed to warm to 25° C. where it was stirred for 2 h. At this time, thin layer chromatography analysis of the reaction mixture indicated the absence of starting material. The reaction mixture was then concentrated in vacuo. The resulting residue was dissolved in ethyl acetate (300 mL). The organic layer was washed successively with a saturated aqueous sodium bicarbonate solution (4×200 mL) and a saturated aqueous sodium chloride solution (1×300 mL), dried over anhydrous magnesium sulfate, filtered, and concentrated in vacuo to afford a yellow solid. Recrystallization from hot ethanol (50 mL) and acetonitrile (10 mL) followed by dilution with hexanes (300 mL) to obtain a precipitate. The solid was collected by filtration and washed with hexanes (100 mL) to afford 4-bromo-1-methanesulfonyl-2-nitro-benzene (8.68 g, 62%) as a white solid: mp 175.5–177° C.; EI-HRMS m/e calcd for $C_7H_6BrNO_4S$ ($M^+$) 278.9201, found 278.9210.

A light brown suspension of 4-bromo-1-methanesulfonyl-2-nitro-benzene (8.65 g, 30.9 mmol) in methanol (300 mL, not completely dissolved in methanol even at hot condition) was treated sequentially with ammonium chloride (24.8 g, 463.5 mmol), zinc dust (20.2 g, 309 mmol), and water (100 mL). Initially, the reaction was exothermic, and the brown color disappeared. The reaction mixture was stirred for 1 h at 25° C. The reaction mixture was then filtered, and the residue was washed with methanol (50 mL) and ethyl acetate (100 mL). The filtrate was concentrated in vacuo, and the organic compound was extracted into ethyl acetate (3×100 mL). The combined organic extracts were washed with a saturated aqueous sodium chloride solution (1×200 mL), dried over anhydrous sodium sulfate, filtered, and concentrated in vacuo. Biotage chromatography (FLASH 40M, Silica, 8/1 to 6/1 to 4/1 hexanes/ethyl acetate) afforded 5-bromo-2-methanesulfonyl-phenylamine (5.7 g, 74%) as a white solid: mp 107–109° C.; EI-HRMS m/e calcd for $C_7H_8BrNO_2S$ ($M^+$) 248.9459, found 248.9451.

A solution of 5-bromo-2-methanesulfonyl-phenylamine (5.7 g, 19.5 mmol) in dry tetrahydrofuran (30 mL) at 25° C. was treated with acetyl chloride (6.28 g, 80 mmol). The resulting solution was stirred overnight at 25° C., at which time, thin layer chromatography analysis of the reaction mixture indicated the absence of starting material. The reaction mixture was then diluted with water (100 mL) and ethyl acetate (100 mL). The two layers were separated, and the aqueous layer was extracted with ethyl acetate (1×100 mL). The combined organic extracts were washed with a saturated aqueous sodium chloride solution (1×200 mL), dried over anhydrous sodium sulfate, filtered, and concentrated in vacuo to afford a brown solid. The brown solid was treated with diethyl ether (50 mL) and hexanes (50 mL). The white solid was collected by filtration and washed with hexanes (50 mL) to afford N-(5-bromo-2-methanesulfonyl-phenyl)-acetamide (4.55 g, 80%) as a white solid: mp 157–160° C.; EI-HRMS m/e calcd for $C_9H_{10}BrNO_3S$ ($M^+$) 290.9565, found 290.9560.

A solution of N-(5bromo-2-methanesulfonyl-phenyl)-acetamide (350 mg, 1.2 mmol) in acetonitrile (6 mL) at 25° C. was treated with sodium azide (78 mg, 1.2 mmol). The reaction mixture was cooled to 0° C. and then treated with trifluoromethanesulfonic anhydride (0.24 mL, 1.2 mmol). The resulting reaction mixture was allowed to warm to 25° C. where it was stirred overnight, at which time, thin layer chromatography analysis of the reaction mixture indicated the absence of starting material. The reaction mixture was then concentrated in vacuo. The resulting residue was diluted with ethyl acetate (50 mL) and water (50 mL). The two layers were separated, and the aqueous layer was extracted with ethyl acetate (1×30 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 8/1 hexanes/ethyl acetate) afforded 1-(5-bromo-2-methanesulfonyl-phenyl)-5-methyl-1H-tetrazole (254 mg, 67%) as a white solid: mp 174–184° C.; EI-HRMS m/e calcd for $C_9H_9BrN_4O_2S$ ($M^+$) 315.9630, found 315.9634.

A mixture of zinc dust (330 mg, 5 mmol, Aldrich, −325 mesh) and dry tetrahydrofuran (1 mL) under argon was treated with 1,2-dibromoethane (93 mg, 0.5 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (54 mg, 0.5 mmol), and the suspension was stirred for 15 min at 25° C. The reaction mixture was then treated dropwise with a solution of (E)-3-cyclopentyl-2-iodo-acrylic acid methyl ester (prepared in Example 7, 420 mg, 1.5 mmol) in dry tetrahydrofuran (1 mL). The resulting reaction mixture was then stirred at 40–45° C. for 1 h and then stirred overnight at 25° C. The reaction mixture was then diluted with dry tetrahydrofuran (3 mL), and the stirring was stopped to allow the excess zinc dust to settle down (~2 h). In a separate reaction flask, bis(dibenzylideneacetone) palladium(0) (27 mg, 0.05 mmol) and triphenylphosphine (52 mg, 0.2 mmol) in dry tetrahydrofuran (3 mL) was stirred at 25° C. under argon for 10 min and then treated with 1-(5-bromo-2-methanesulfonyl-phenyl)-5-methyl-1H-tetrazole (237 mg, 0.75 mmol) and the freshly prepared zinc compound in tetrahydrofuran. The resulting brick red solution was heated at 40–45° C. over the weekend. The reaction mixture was cooled to 25° C. and then poured into a saturated aqueous ammonium chloride solution (30 mL), and the organic compound was extracted into ethyl acetate (3×30 mL). The combined organic extracts were washed with a saturated aqueous sodium chloride solution (1×100 mL), dried over anhydrous magnesium sulfate, filtered, and concentrated in vacuo. Biotage chromatography (FLASH 40S, Silica, 3/1 to 1/1 hexanes/ethyl acetate) afforded (E)-3-cyclopentyl-2-[4-methanesulfonyl-3-(5-methyl-tetrazol-1-yl)-phenyl]-acrylic acid methyl ester (266 mg, 91%) as a white solid: mp 164–166° C.; EI-HRMS m/e calcd for $C_{18}H_{22}N_4O_4S$ ($M^+$) 390.1362, found 390.1368.

A solution of nickel (II) chloride hexahydrate (12.2 mg, 0.05 mmol) and (E)-3-cyclopentyl-2-[4-methanesulfonyl-3-(5-methyl-tetrazol-1-yl)-phenyl]-acrylic acid methyl ester (100 mg, 0.26 mmol) in methanol (5 mL) was cooled to 0° C. and then treated with sodium borohydride (29 mg, 0.77 mmol). After the addition, the black reaction mixture was stirred for 15 min at 0° C. and then allowed to warm to 25° C. where it was stirred for 15 h. The reaction mixture was concentrated in vacuo, and the residue was diluted with a 3N aqueous hydrochloric acid solution (10 mL) and ethyl acetate (25 mL). The two layers were separated. The organic layer was washed with a saturated aqueous sodium chloride solution (1×25 mL), dried over anhydrous magnesium sulfate, filtered, and concentrated in vacuo to afford racemic 3-cyclopentyl-2-[4-methanesulfonyl-3-(5-methyl-tetrazol-1-yl)-phenyl]-propionic acid methyl ester (105 mg, 99%) as a viscous oil: EI-HRMS m/e calcd for $C_{18}H_{24}N_4O_4S$ ($M^+$) 392.1518, found 392.1526.

A solution of 3-cyclopentyl-2-[4-methanesulfonyl-3-(5-methyl-tetrazol-1-yl)-phenyl]-propionic acid methyl ester (102 mg, 0.26 mmol) in ethanol (3 mL) was treated with a 1N aqueous sodium hydroxide solution (0.6 mL). The solution was ³heated at 45–50° C. for 5 h, at which time, thin layer chromatography analysis of the reaction mixture indicated the absence of starting material. The reaction mixture was concentrated in vacuo to remove ethanol. The residue was diluted with water (20 mL) and extracted with diethyl ether (1×30 mL) to remove any neutral impurities. The aqueous layer was then acidified with a 1N aqueous hydrochloric acid solution, and the resulting acid was extracted into ethyl acetate (2×25 mL). The combined organic layers were washed with a saturated aqueous sodium chloride solution (1×50 mL), dried over anhydrous magnesium sulfate, filtered, and concentrated in vacuo to afford 3-cyclopentyl-2-[4-methanesulfonyl-3-(5-methyl-tetrazol-1-yl)-phenyl]-propionic acid (88 mg, 89%) as an amorphous white solid: EI-HRMS m/e calcd for $C_{17}H_{22}N_4O_4S$ ($M^+$) 378.1362, found 378.1364.

A solution of triphenylphosphine (100 mg, 0.38 mmol) in methylene chloride (3 mL) was cooled to 0° C. and then treated with N-bromosuccinimide (68 mg, 0.38 mmol). The reaction mixture was stirred at 0° C. for 30 min and then treated with a solution of 3-cyclopentyl-2-[4-methanesulfonyl-3-(5-methyl-tetrazol-1-yl)-phenyl]-propionic acid (85 mg, 0.22 mmol) in methylene chloride (3 mL). The clear solution was stirred for 15 min at 0° C. and then allowed to warm to 25° C. where it was stirred for 1.5 h. The reaction mixture was then treated with 2-aminothiazole (55 mg, 0.55 mmol), and the resulting suspension was stirred for 2 d at 25° C. The reaction mixture was then concentrated in vacuo to remove methylene chloride, and the residue was diluted with ethyl acetate (30 mL) and a 1N aqueous hydrochloric acid solution (25 mL). The two layers were separated, and the aqueous layer was extracted with ethyl acetate (1×25 mL). The combined organic extracts were successively washed with a 1N aqueous hydrochloric acid solution (1×50 mL), a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40S, Silica, 2/1 to 1/1 hexanes/ethyl acetate) afforded 3-cyclopentyl-2-[4-methanesulfonyl-3-(5-methyl-tetrazol-1-yl)-phenyl]-N-thiazol-2-yl-propionamide (42 mg, 41 %) as a white solid: mp 148–154° C.; EI-HRMS m/e calcd for $C_{20}H_{24}N_6O_3S_2$ ($M^+$) 460.1351, found 460.1356.

EXAMPLE 10

1-{3-Cyclopentyl-2-[4-(5-methyl-tetrazol-1-yl)-3-trifluoromethyl-phenyl]-propionyl}-3-methyl-urea

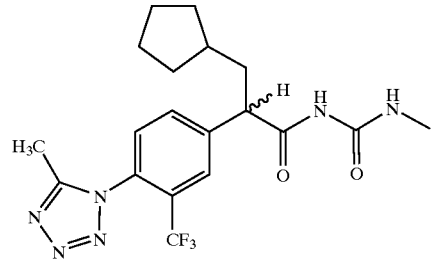

A solution of 2-(trifluoromethyl)-4-bromoaniline (4.8 g, 20 mmol) in dry tetrahydrofuran (20 mL) was cooled to 0° C. and then treated with acetic anhydride (8.2 g, 80 mmol). The reaction mixture was stirred at 0° C. for 10 min and then allowed to warm to 25° C. The reaction mixture was stirred at 25° C. for 2 h, at which time, thin layer chromatography analysis of the reaction mixture indicated the absence of starting material. The reaction mixture was then concentrated in vacuo. The crude residue precipitated from diethyl ether (50 mL) and hexanes (50 mL). The solid was collected by filtrated and washed with hexanes to afford N-(4-bromo-2-trifluoromethyl-phenyl)-acetamide (5.07 g, 90%) as an amorphous white solid: EI-HRMS m/e calcd for $C_9H_7BrF_3NO$ ($M^+$) 281.8352, found 281.8348.

A suspension of N-(4-bromo-2-trifluoromethyl-phenyl)-acetamide (2.41 g, 8.54 mmol) in acetonitrile (40 mL) was treated with methylene chloride (5 mL) to obtain a clear solution at 25° C. The resulting solution was treated with sodium azide (1.24 g, 19.1 mmol), and the reaction mixture was then cooled to 0° C. The reaction mixture was then treated with trifluoromethanesulfonic anhydride (3.59 g, 12.7 mmol). The resulting reaction mixture was allowed to warm to 25° C. where it was stirred overnight, at which time, thin layer chromatography analysis of the reaction mixture indicated the absence of starting material. The reaction mixture was then concentrated in vacuo. The resulting residue was diluted with ethyl acetate (50 mL) and water (50 mL). The two layers were separated, and the aqueous layer was extracted with ethyl acetate (1×30 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 2/1 hexanes/ethyl acetate) afforded 1-(4-bromo-2-trifluoromethyl-phenyl)-5-methyl-1H-tetrazole (1.85 g, 70%) as a white solid: EI-HRMS m/e calcd for $C_9H_6BrF_3N_4$ ($M^+$) 305.9728, found 305.9733.

A mixture of lithium chloride (8.48 g, 200 mmol, predried at 130° C. under high vacuum for 3 h) and copper cyanide (8.96 g, 100 mmol) in dry tetrahydrofuran (100 mL) was stirred at 25° C. under argon for 10 min to obtain a clear solution. The reaction mixture was then cooled to −70° C. and then slowly treated with a 2.0M solution of cyclopentylmagnesium chloride in diethyl ether (55 mL, 110 mmol). After the addition, the reaction mixture was allowed to warm to −30° C. where it was stirred for 5 min. The resulting reaction mixture was again cooled back to −70° C. and then slowly treated with methyl propiolate (7.99 g, 95 mmol). The reaction mixture was stirred overnight at −60° C. to −50° C. The reaction mixture was then slowly treated with a solution of iodine (34.3 g, 135 mmol) in dry tetrahydrofuran (30 mL), with the temperature kept at −70° C. to −60° C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (200 mL) and ammonium hydroxide (50 mL), and the organic compound was extracted into diethyl ether (3×100 mL). The combined organic extracts were successively washed with a saturated aqueous sodium thiosulfate solution (1×300 mL) and a saturated aqueous sodium chloride solution (1×300 mL). The organic layer was then dried over anhydrous magnesium sulfate, filtered, and concentrated in vacuo. Flash chromatography (Merck Silica gel 60, 230–400 mesh, 20/1 hexanes/diethyl ether) afforded (E)-3-cyclopentyl-2-iodo-acrylic acid methyl ester (25.8 g, 97%) as a yellow oil: EI-HRMS m/e calcd for $C_9H_{13}IO_2$ ($M^+$) 279.9960, found 279.9961.

A mixture of zinc dust (710 mg, 11 mmol, Aldrich, −325 mesh) and dry tetrahydrofuran (1 mL) under argon was treated with 1,2-dibromoethane (187 mg, 1 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (108 mg, 1 mmol), and the suspension was stirred for 15 min at 25° C. The reaction mixture was then treated dropwise with a solution of (E)-3-cyclopentyl-2-iodo-acrylic acid methyl ester (1.54 g, 5.5 mmol) in dry tetrahydrofuran (2 mL) over 3 min. The reaction mixture was then stirred at 40–45° C. for 1 h and then stirred overnight at 25° C. The reaction mixture was then diluted with dry tetrahydrofuran (4 mL), and the stirring was stopped to allow the excess zinc dust to settle down (~2 h). In a separate reaction flask, bis(dibenzylideneacetone) palladium(0) (81 mg, 0.15 mmol) and triphenylphosphine (156 mg, 0.6 mmol) in dry tetrahydrofuran (6 mL) was stirred at 25° C. under argon for 10 min and then treated with 1-(4-bromo-2-trifluoromethyl-phenyl)-5-methyl-1H-tetrazole (1.05 g, 3.5 mmol) and the freshly prepared zinc compound in tetrahydrofuran. The resulting brick red solution was heated at 40–45° C. over the weekend. The reaction mixture was cooled to 25° C. and then poured into a saturated aqueous ammonium chloride solution (50 mL), and the organic compound was extracted into ethyl acetate (3×35 mL). The combined organic extracts were washed with a saturated aqueous sodium chloride solution (1×100 mL), dried over anhydrous magnesium sulfate, filtered, and concentrated in vacuo. Flash chromatography (Merck Silica gel 60, 230–400 mesh, 4/1 to 1/1 hexanes/ethyl acetate) afforded (E)-3-cyclopentyl-2-[4-(5-methyl-tetrazol-1-yl)-3-trifluoromethyl-phenyl]-acrylic acid methyl ester (1.03 g, 77.6%) as a light yellow solid: EI-HRMS m/e calcd for $C_{18}H_{19}F_3N_4O_2$ ($M^+$) 380.1460, found 380.1453.

A solution of nickel (II) chloride hexahydrate (102 mg, 0.428 mmol) and (E)-3-cyclopentyl-2-[4-(5-methyl-tetrazol-1-yl)-3-trifluoromethyl-phenyl]-acrylic acid methyl ester (814 mg, 2.14 mmol) in methanol (20 mL) was cooled to 0° C. and then treated with sodium borohydride (265 mg, 7 mmol) in five portions. After the addition, the black reaction mixture was stirred for 15 min at 0° C. and then allowed to warm to 25° C. where it was stirred for 15 h. The reaction mixture was concentrated in vacuo, and the residue was diluted with a 3N aqueous hydrochloric acid solution (50 mL) and ethyl acetate (75 mL). The two layers were separated. The organic layer was washed with a saturated aqueous sodium chloride solution (1×50 mL), dried over anhydrous magnesium sulfate, filtered, and concentrated in vacuo to afford racemic 3-cyclopentyl-2-[4-(5-methyl-tetrazol-1-yl)-3-trifluoromethyl-phenyl]-propionic acid methyl ester (815 mg, 99%) as a viscous oil: EI-HRMS m/e calcd for $C_{18}H_{21}F_3N_4O_2$ ($M^+$) 382.1617, found 382.1617.

A solution of 3-cyclopentyl-2-[4-(5-methyl-tetrazol-1-yl)-3-trifluoromethyl-phenyl]-propionic acid methyl ester (870 mg, 2.27 mmol) in ethanol (12 mL) was treated with a 1N aqueous sodium hydroxide solution (8 mL). The solution was heated at 45–50° C. for 3 h, at which time, thin layer chromatography analysis of the reaction mixture indicated the absence of starting material. The reaction mixture was concentrated in vacuo to remove ethanol. The residue was diluted with water (50 mL) and extracted with diethyl ether (1×60 mL) to remove any neutral impurities. The aqueous layer was then acidified with a 1N aqueous hydrochloric acid solution, and the resulting acid was extracted into ethyl acetate (2×50 mL). The combined organic layers were washed with a saturated aqueous sodium chloride solution (1×100 mL), dried over anhydrous magnesium sulfate, filtered, and concentrated in vacuo to afford 3-cyclopentyl-2-[4-(5-methyl-tetrazol-1-yl)-3-trifluoromethyl-phenyl]-propionic acid (781 mg, 93%) as a white solid: EI-HRMS m/e calcd for $C_{17}H_{19}F_3N_4O_2$ ($M^+$) 368.1460, found 368.1460.

A solution of 3-cyclopentyl-2-[4-(5-methyl-tetrazol-1-yl)-3-trifluoromethyl-phenyl]-propionic acid (368 mg, 1.0 mmol) in fluorobenzene (1.5 mL) and N,N-dimethylformamide (6 µL) at 25° C. was treated dropwise with oxalyl chloride (107.7 µL, 1.21 mmol) over 2–3 min. The clear solution was stirred for 1 h at 25° C. and then treated with methyl urea (322 mg, 2.0 mmol). The resulting suspension was heated at 70° C. (bath temperature) for 10 min and then treated with pyridine (162 µL, 2.0 mmol). The reaction mixture was then stirred at 70° C. for 20 h. The reaction mixture was then cooled to 25° C. and diluted with ethyl acetate (30 mL) and a 3N aqueous hydrochloric acid solution (30 mL). The two layers were separated, and the aqueous layer was extracted with ethyl acetate (1×20 mL). The combined organic extracts were successively washed with a saturated aqueous sodium bicarbonate solution (1×50 mL) and a saturated aqueous sodium chloride solution (1×50 mL), dried over anhydrous magnesium sulfate, filtered, and concentrated, in vacuo. Biotage chromatography (FLASH 40S, Silica, 1/1 to 1/2 hexanes/ethyl acetate) afforded 1-{3-cyclopentyl-2-[4-(5-methyl-tetrazol-1-yl)-3-trifluoromethyl-phenyl]-propionyl}-3-methyl-urea (338 mg,

EXAMPLE 11

1-{2-[3-Chloro-4-(5-methyl-tetrazol-1-yl)-phenyl]-3-cyclopentyl-propionyl}-3-methyl-urea

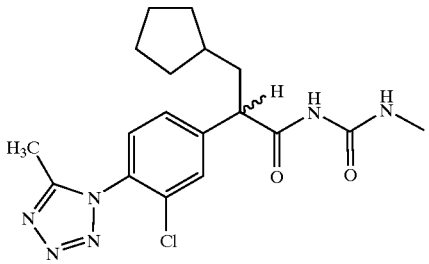

80%) as an amorphous white solid: EI-HRMS m/e calcd for $C_{19}H_{23}F_3N_6O_2$ (M+) 424.1834, found 424.1833.

A suspension of triphenylphospine (11.7 g, 44.8 mmol) in carbon tetrachloride (8 mL, 83 mmol) was cooled to 0° C. and then treated with triethylamine (2.5 mL, 18 mmol) and acetic acid (1.15 mL, 20 mmol). The reaction mixture was stirred at 0° C. for 10 min and then treated with a solution of 2-chloro-4-iodoaniline (5.07 g, 20 mmol) in carbon tetrachloride (12 mL, heated to obtain a solution). The resulting light brown suspension was allowed to warm to 25° C. and then it was refluxed overnight. The reaction mixture was cooled to 25° C. and then concentrated in vacuo. The resulting solid residue was then diluted with hexanes (50 mL) and methylene chloride (50 mL). The precipitated solid was collected by filtration and washed with hexanes. The filtrate was concentrated in vacuo, and the resulting residue was diluted with diethyl ether (100 mL). The precipitated solid was collected by filtration and washed with hexanes, and the filtrate was concentrated in vacuo. The resulting residue was again diluted with hexanes (100 mL), and the precipitated solid was collected by filtration. The filtrate was finally concentrated in vacuo to afford the imidoyl chloride intermediate (4.08 g) as a liquid. This crude imidoyl chloride intermediate (4.08 g, ~13 mmol) was treated with sodium azide (1.04 g, 16 mmol) and acetic acid (10 mL). The reaction was exothermic, and the resulting reaction mixture was stirred for 1 h at 25° C. The reaction mixture was then heated at 70° C. for 2 h, at which time, thin layer chromatography analysis of the reaction mixture indicated the absence of the imidoyl chloride intermediate. The cloudy yellow suspension was cooled to 25° C. and then diluted with water (100 mL) and extracted with ethyl acetate (2×75 mL). The combined organic extracts were washed successively with a saturated aqueous sodium bicarbonate solution (1×100 mL) and a saturated aqueous sodium chloride solution (1×100 mL), dried over anhydrous magnesium sulfate, filtered, and concentrated in vacuo. Biotage chromatography (FLASH 40M, Silica, 6/1 hexanes/diethyl ether) afforded 1-(2-chloro-4-iodo-phenyl)-5-methyl-1H-tetrazole (350 mg, 6%) as a white solid: mp 128–130.5° C.; EI-HRMS m/e calcd for $C_8H_6ClIN_4$ (M+) 319.9327, found 319.9325.

A mixture of zinc dust (650 mg, 10 mmol, Aldrich, −325 mesh) and dry tetrahydrofuran (1 mL) under argon was treated with 1,2-dibromoethane (187 mg, 1 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (108 mg, 1 mmol), and the suspension was stirred for 15 min at 25° C. The reaction mixture was then treated dropwise with a solution of (E)-3-cyclopentyl-2-iodo-acrylic acid methyl ester (prepared in Example 10, 1.26 g, 4.5 mmol) in dry tetrahydrofuran (2 mL) over 3 min. The reaction mixture was then stirred at 40–45° C. for 1 h and then stirred overnight at 25° C. The reaction mixture was then diluted with dry tetrahydrofuran (3 mL), and the stirring was stopped to allow the excess zinc dust to settle down (~2 h). In a separate reaction flask, bis (dibenzylideneacetone)palladium(0) (54 mg, 0.1 mmol) and triphenylphosphine (104 mg, 0.4 mmol) in dry tetrahydrofuran (4 mL) was stirred at 25° C. under argon for 10 min and then treated with 1-(2-chloro-4-iodo-phenyl)-5-methyl-1H-tetrazole (875 mg, 2.73 mmol) and the freshly prepared zinc compound in tetrahydrofuran. The resulting brick red solution was stirred at 25° C. over the weekend and then heated at 40–45° C. for 4 h. The reaction mixture was cooled to 25° C. and then poured into a saturated aqueous ammonium chloride solution (50 mL), and the organic compound was extracted into ethyl acetate (3×35 mL). The combined organic extracts were washed with a saturated aqueous sodium chloride solution (1×100 mL), dried over anhydrous magnesium sulfate, filtered, and concentrated in vacuo. Flash chromatography (Merck Silica gel 60, 230–400 mesh, 4/1 to 1/1 hexanes/ethyl acetate) afforded (E)-2-[3-chloro-4-(5-methyl-tetrazol-1-yl)-phenyl]-3-cyclopentyl-acrylic acid methyl ester (859 mg, 91%) as a light yellow semi-solid: EI-HRMS m/e calcd for $C_{17}H_{19}ClN_4O_2$ (M+) 346.1196, found 346.1190.

A solution of nickel (II) chloride hexahydrate (180 mg, 0.8 mmol) and (E)-2-[3-chloro-4-(5-methyl-tetrazol-1-yl)-phenyl]-3-cyclopentyl-acrylic acid methyl ester (695 mg, 2.0 mmol) in methanol (15 mL) was cooled to 0° C. and then treated with sodium borohydride (454 mg, 12 mmol) in five portions. After the addition, the black reaction mixture was stirred for 15 min at 0° C. and then allowed to warm to 25° C. where it was stirred for 2 d. The reaction mixture was concentrated in vacuo, and the residue was diluted with a 3N aqueous hydrochloric acid solution (50 mL) and ethyl acetate (75 mL). The two layers were separated. The organic layer was washed with a saturated aqueous sodium chloride solution (1×50 mL), dried over anhydrous magnesium sulfate, filtered, and concentrated in vacuo to afford racemic 2-[3-chloro-4-(5-methyl-tetrazol-1-yl)-phenyl]-3-cyclopentyl-propionic acid methyl ester (815 mg, 99%) as a viscous oil: EI-HRMS m/e calcd for $C_{17}H_{21}ClN_4O_2$ (M+) 348.1353, found 348.1359.

A solution of 2-[3-chloro-4-(5-methyl-tetrazol-1-yl)-phenyl]-3-cyclopentyl-propionic acid methyl ester ester (690 mg, 2.0 mmol) in ethanol (20 mL) was treated with a 1N aqueous sodium hydroxide solution (4 mL). The solution was heated at 45–50° C. for 3 h, at which time, thin layer chromatography analysis of the reaction mixture indicated the absence of starting material. The reaction mixture was concentrated in vacuo to remove ethanol. The residue was diluted with water (50 mL) and extracted with diethyl ether (1×60 mL) to remove any neutral impurities. The aqueous layer was then acidified with a 1N aqueous hydrochloric acid solution, and the resulting acid was extracted into ethyl acetate (2×50 mL). The combined organic layers were washed with a saturated aqueous sodium chloride solution (1×100 mL), dried over anhydrous magnesium sulfate, filtered, and concentrated in vacuo to afford 2-[3-chloro-4-(5-methyl-tetrazol-1-yl)-phenyl]-3-cyclopentyl-propionic acid (604 mg, 90%) as an amorphous white solid: EI-HRMS m/e calcd for $C_{16}H_{19}ClN_4O_2$ (M+) 334.1196, found 334.1193.

A solution of 2-[3-chloro-4-(5-methyl-tetrazol-1-yl)-phenyl]-3-cyclopentyl-propionic acid (303 mg, 0.9 mmol) in fluorobenzene (1 mL) and N,N-dimethylformamide (3 µL) at 25° C. was treated dropwise with oxalyl chloride (97 µL, 1.09 mmol) over 2–3 min. The clear solution was stirred at 25° C. for 1 h and then treated with methyl urea (201 mg, 2.72 mmol). The resulting suspension was heated at 70° C. (bath temperature) for 10 min and then treated with pyridine (146.6 µL, 1.81 mmol). The reaction mixture was then stirred at 70° C. for 20 h. The reaction mixture was then cooled to 25° C. and diluted with ethyl acetate (30 mL) and a 3N aqueous hydrochloric acid solution (30 mL). The two layers were separated, and the aqueous layer was extracted with ethyl acetate (1×20 mL). The combined organic extracts were successively washed with a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40M, Silica, 1/1 hexanes/ethyl acetate) afforded 1-{2-[3-chloro-4-(5-methyl-tetrazol-1-yl)-phenyl]-3-cyclopentyl-propionyl}-3-methyl-urea (110 mg, 31%) as a white solid: mp 185–186° C. EI-HRMS m/e calcd for $C_{18}H_{23}ClN_6O_2$ (M+H)$^+$391.1649, found 391.1659.

EXAMPLE 12

(E)-3-Cyclopentyl-2-[3-fluoro-4-(5-methyl-tetrazol-1-yl)-phenyl]-N-thiazol-2-yl-acrlamide

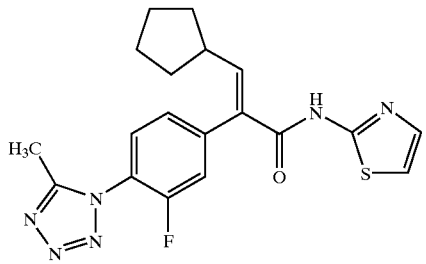

A solution of 2-fluoro-4-iodoaniline (4.74 g, 20 mmol) in dry tetrahydrofuran (20 mL) was cooled to 0° C. and then treated with acetic anhydride (8.2 g, 80 mmol). The reaction mixture was stirred for 10 min at 0° C. and then was allowed to warm to 25° C. where it was stirred for 2 h. After this time, thin layer chromatography analysis of the reaction mixture indicated the absence of starting material. The reaction mixture was then concentrated in vacuo to afford a crude residue. The residue precipitated from diethyl ether (50 mL) and hexanes (50 mL). The solid was collected by filtration and washed with hexanes to afford N-(2-fluoro-4-iodo-phenyl)-acetamide (5.12 g, 92%) as a white crystalline solid: mp 152–154° C.; EI-HRMS m/e calcd for $C_8H_7FINO$ (M$^+$) 278.9556, found 278.9559.

A suspension of N-(2-fluoro-4-iodo-phenyl)-acetamide (5.00 g, 18.24 mmol) in acetonitrile (100 mL) was cooled to 0° C. and then treated with sodium azide (3.56 g, 54.7 mmol). The reaction mixture was then treated with trifluoromethanesulfonic anhydride (13.6 g, 48 mmol). The resulting reaction mixture was allowed to warm to 25° C. where it was stirred overnight, at which time, thin layer chromatography analysis of the reaction mixture indicated the absence of starting material. The reaction mixture was then concentrated in vacuo. The resulting residue was diluted with ethyl acetate (100 mL) and water (100 mL). The two layers were separated, and the aqueous layer was extracted with ethyl acetate (1×50 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 4/1 hexanes/ethyl acetate) afforded 1-(2-fluoro-4-iodo-phenyl)-5-methyl-1H-tetrazole (3.45 g, 62%) as a white solid: mp 122-124° C.; EI-HRMS m/e calcd for $C_8H_6FIN_4$ (M$^+$) 303.9621, found 303.9615.

A mixture of lithium chloride (8.48 g, 200 mmol, predried at 130° C. under high vacuum for 3 h) and copper cyanide (8.96 g, 100 mmol) in dry tetrahydrofuran (100 mL) was stirred at 25° C. under argon for 10 min to obtain a clear solution. The reaction mixture was then cooled to −70° C. and then slowly treated with a 2.0M solution of cyclopentylmagnesium chloride in diethyl ether (55 mL, 110 mmol). After the addition, the reaction mixture was allowed to warm to −30° C. where it was stirred for 5 min. The resulting reaction mixture was again cooled back to −70° C. and then slowly treated with methyl propiolate (7.99 g, 95 mmol). The reaction mixture was stirred overnight at −60° C. to −50° C. The reaction mixture was then slowly treated with a solution of iodine (34.3 g, 135 mmol) in dry tetrahydrofuran (30 mL), with the temperature kept at −70° C. to −60° C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (200 mL) and ammonium hydroxide (50 mL), and the organic compound was extracted into diethyl ether (3×100 mL). The combined organic extracts were successively washed with a saturated aqueous sodium thiosulfate solution (1×300 mL) and a saturated aqueous sodium chloride solution (1×300 mL). The organic layer was then dried over anhydrous magnesium sulfate, filtered, and concentrated in vacuo. Flash chromatography (Merck Silica gel 60, 230–400 mesh, 20/1 hexanes/diethyl ether) afforded (E)-3-cyclopentyl-2-iodo-acrylic acid methyl ester (25.8 g, 97%) as a yellow oil: EI-HRMS m/e calcd for $C_9H_{13}IO_2$ (M$^+$) 279.9960, found 279.9961.

A mixture of zinc dust (650 mg, 10 mmol, Aldrich, −325 mesh) and dry tetrahydrofuran (1 mL) under argon was treated with 1,2-dibromoethane (187 mg, 1 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (108 mg, 1 mmol), and the suspension was stirred for 15 min at 25° C. The reaction mixture was then treated dropwise with a solution of (E)-3-cyclopentyl-2-iodo-acrylic acid methyl ester (2.21 g, 7.5 mmol) in dry tetrahydrofuran (3 mL) over 3 min. The resulting reaction mixture was then stirred at 40–45° C. for 1 h and then stirred overnight at 25° C. The reaction mixture was then diluted with dry tetrahydrofuran (5 mL), and the stirring was stopped to allow the excess zinc dust to settle down (~2 h). In a separate reaction flask, bis(dibenzylideneacetone) palladium(0) (90 mg, 0.16 mmol) and triphenylphosphine (160 mg, 0.6 mmol) in dry tetrahydrofuran (10 mL) was stirred at 25° C. under argon for 10 min and then treated with 1-(2-fluoro-4-iodo-phenyl)-5-methyl-1H-tetrazole (1.52 g, 5 mmol) and the freshly prepared zinc compound in tetrahydrofuran. The resulting brick red solution was stirred at 25° C. over the weekend and then heated at 40–45° C. for 4 h. The reaction mixture was cooled to 25° C. and then poured into a saturated aqueous ammonium chloride solution (50 mL), and the organic compound was extracted into ethyl acetate (3×50 mL). The combined organic extracts were washed with a saturated aqueous sodium chloride solution 1×100 mL), dried over anhydrous magnesium sulfate, filtered, and concentrated in vacuo. Flash chromatography (Merck Silica gel 60, 230–400 mesh, 4/1 to 1/1 hexanes/ethyl acetate) afforded (E)-3-cyclopentyl-2-[3-fluoro-4-(5-methyl-tetrazol-1-yl)-phenyl]-acrylic acid methyl ester (1.14 g, 68%) as a light yellow solid: mp 111–114° C.; EI-HRMS m/e calcd for $C_{17}H_{19}FN_4O_2$ (M+) 330.1492, found 330.1493.

A solution of (E)-3-cyclopentyl-2-[3-fluoro-4-(5-methyl-tetrazol-1-yl)-phenyl]-acrylic acid methyl ester (720 mg, 2.18 mmol) in ethanol (15 mL) was treated with a 1N aqueous sodium hydroxide solution (5 mL). The solution was heated at 45–50° C. for 15 h, at which time, thin layer chromatography analysis of the reaction mixture indicated the absence of starting material. The reaction mixture was concentrated in vacuo to remove ethanol. The residue was diluted with water (30 mL) and extracted with diethyl ether (1×50 mL) to remove any neutral impurities. The aqueous layer was then acidified with a 1N aqueous hydrochloric acid solution, and the resulting acid was extracted into ethyl acetate (2×50 mL). The combined organic layers were washed with a saturated aqueous sodium chloride solution (1×100 mL), dried over anhydrous magnesium sulfate, filtered, and concentrated in vacuo to afford (E)-3-cyclopentyl-2-[3-fluoro-4-(5-methyl-tetrazol-1-yl)-phenyl]-acrylic acid (690 mg, 100%) as a white solid: mp 182–185° C.; EI-HRMS m/e calcd for $C_{16}H_{17}FN_4O_2$ (M+) 316.1336, found 316.1334.

A solution of triphenylphosphine (262 mg, 1 mmol) in methylene chloride (6 mL) was cooled to 0° C. and then treated with N-bromosuccinimide (178 mg, 1 mmol). The reaction mixture was stirred at 0° C. for 30 min and then treated with (E)-3-cyclopentyl-2-[3-fluoro-4-(5-methyl-tetrazol-1-yl)-phenyl]-acrylic acid (158 mg, 0.5 mmol). The reaction mixture was stirred for 15 min at 0° C. and then allowed to warm to 25° C. where it was stirred for 1.5 h. The reaction mixture was then treated with 2-aminothiazole (150 mg, 1.5 mmol), and the resulting suspension was stirred for 2 d at 25° C. The reaction mixture was then concentrated in vacuo to remove methylene chloride, and the residue was diluted with ethyl acetate (20 mL) and a 1N aqueous hydrochloric acid solution (30 mL). The two layers were separated, and the aqueous layer was extracted with ethyl acetate (1×15 mL). The combined organic extracts were successively washed with a 1N aqueous hydrochloric acid solution 1×50 mL), a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40S, Silica, 1/1 hexanes/ethyl acetate) afforded (E)-3-cyclopentyl-2-[3-fluoro-4-(5-methyl-tetrazol-1-yl)-phenyl]-N-thiazol-2-yl-acrylamide (39 mg, 20%) as a white solid: mp 158–162° C.; EI-HRMS m/e calcd for $C_{19}H_{19}FN_6OS$ (M+) 398.1325, found 398.1323.

EXAMPLE 13

(E)-N-(5-Bromo-pyridin-2-yl)-3-cyclopentyl-2-[3-fluoro-4-(5-methyl-tetrazol-1-yl)-phenyl]-acrylamide

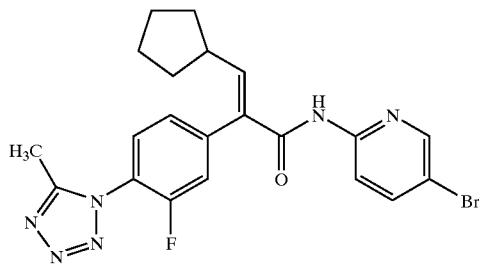

A solution of 2-fluoro-4-iodoaniline (4.74 g, 20 mmol) in dry tetrahydrofuran (20 mL) was cooled to 0° C. and then treated with acetic anhydride (8.2 g, 80 mmol). The reaction mixture was stirred for 10 min at 0° C. and then was allowed to warm to 25° C. where it was stirred for 2 h. After this time, thin layer chromatography analysis of the reaction mixture indicated the absence of starting material. The reaction mixture was then concentrated in vacuo to afford a crude residue. The residue precipitated from diethyl ether (50 mL) and hexanes (50 mL). The solid was collected by filtration and washed with hexanes to afford N-(2-fluoro-4-iodo-phenyl)-acetamide (5.12 g, 92%) as a white crystalline solid: mp 152–154° C.; EI-HRMS m/e calcd for $C_8H_7FINO$ (M+) 278.9556, found 278.9559.

A suspension of N-(2-fluoro-4-iodo-phenyl)-acetamide (5.00 g, 18.24 mmol) in acetonitrile (100 mL) was cooled to 0° C. and then treated with sodium azide (3.56 g, 54.7 mmol). The reaction mixture was then treated with trifluoromethanesulfonic anhydride (13.6 g, 48 mmol). The resulting reaction mixture was allowed to warm to 25° C. where it was stirred overnight, at which time, thin layer chromatography analysis of the reaction mixture indicated the absence of starting material. The reaction mixture was then concentrated in vacuo. The resulting residue was diluted with ethyl acetate (100 mL) and water (100 mL). The two layers were separated, and the aqueous layer was extracted with ethyl acetate (1×50 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 4/1 hexanes/ethyl acetate) afforded 1-(2-fluoro-4-iodo-phenyl)-5-methyl-1H-tetrazole (3.45 g, 62%) as a white solid: mp 122–124° C.; EI-HRMS m/e calcd for $C_8H_6FIN_4$ (M+) 303.9621, found 303.9615.

A mixture of lithium chloride (8.48 g, 200 mmol, predried at 130° C. under high vacuum for 3 h) and copper cyanide (8.96 g, 100 mmol) in dry tetrahydrofuran (100 mL) was stirred at 25° C. under argon for 10 min to obtain a clear solution. The reaction mixture was then cooled to −70° C. and then slowly treated with a 2.0M solution of cyclopentylmagnesium chloride in diethyl ether (55 mL, 110 mmol). After the addition, the reaction mixture was allowed to warm to −30° C. where it was stirred for 5 min. The resulting reaction mixture was again cooled back to −70° C. and then slowly treated with methyl propiolate (7.99 g, 95 mmol). The reaction mixture was stirred overnight at −60° C. to −50° C. The reaction mixture was then slowly treated with a solution of iodine (34.3 g, 135 mmol) in dry tetrahydrofuran (30 mL), with the temperature kept at −70° C. to −60°

C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (200 mL) and ammonium hydroxide (50 mL), and the organic compound was extracted into diethyl ether (3×100 mL). The combined organic extracts were successively washed with a saturated aqueous sodium thiosulfate solution (1×300 mL) and a saturated aqueous sodium chloride solution (1×300 mL). The organic layer was then dried over anhydrous magnesium sulfate, filtered, and concentrated in vacuo. Flash chromatography (Merck Silica gel 60, 230–400 mesh, 20/1 hexanes/diethyl ether) afforded (E)-3-cyclopentyl-2-iodo-acrylic acid methyl ester (25.8 g, 97%) as a yellow oil: EI-HRMS m/e calcd for $C_9H_{13}IO_2$ ($M^+$) 279.9960, found 279.9961.

A mixture of zinc dust (650 mg, 10 mmol, Aldrich, −325 mesh) and dry tetrahydrofuran (1 mL) under argon was treated with 1,2-dibromoethane (187 mg, 1 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (108 mg, 1 mmol), and the suspension was stirred for 15 min at 25° C. The reaction mixture was then treated dropwise with a solution of (E)-3-cyclopentyl-2-iodo-acrylic acid methyl ester (2.21 g, 7.5 mmol) in dry tetrahydrofuran (3 mL) over 3 min. The resulting reaction mixture was then stirred at 40–45° C. for 1 h and then stirred overnight at 25° C. The reaction mixture was then diluted with dry tetrahydrofuran (5 mL), and the stirring was stopped to allow the excess zinc dust to settle down (~2 h). In a separate reaction flask, bis(dibenzylideneacetone)palladium(0) (90 mg, 0.16 mmol) and triphenylphosphine (160 mg, 0.6 mmol) in dry tetrahydrofuran (10 mL) was stirred at 25° C. under argon for 10 min and then treated with 1-(2-fluoro-4-iodo-phenyl)-5-methyl-1H-tetrazole (1.52 g, 5 mmol) and the freshly prepared zinc compound in tetrahydrofuran. The resulting brick red solution was stirred at 25° C. over the weekend and then heated at 40–45° C. for 4 h. The reaction mixture was cooled to 25° C. and then poured into a saturated aqueous ammonium chloride solution (50 mL), and the organic compound was extracted into ethyl acetate (3×50 mL). The combined organic extracts were washed with a saturated aqueous sodium chloride solution (1×100 mL), dried over anhydrous magnesium sulfate, filtered, and concentrated in vacuo. Flash chromatography (Merck Silica gel 60, 230–400 mesh, 4/1 to 1/1 hexanes/ethyl acetate) afforded (E)-3-cyclopentyl-2-[3-fluoro-4-(5-methyl-tetrazol-1-yl)-phenyl]-acrylic acid methyl ester (1.14 g, 68%) as a light yellow solid: mp 111–114° C.; EI-HRMS m/e calcd for $C_{17}H_{19}FN_4O_2$ ($M^+$) 330.1492, found 330.1493.

A solution of (E)-3-cyclopentyl-2-[3-fluoro-4-(5-methyl-tetrazol-1-yl)-phenyl]-acrylic acid methyl ester (720 mg, 2.18 mmol) in ethanol (15 mL) was treated with a 1N aqueous sodium hydroxide solution (5 mL). The solution was heated at 45–50° C. for 15 h, at which time, thin layer chromatography analysis of the reaction mixture indicated the absence of starting material. The reaction mixture was concentrated in vacuo to remove ethanol. The residue was diluted with water (30 mL) and extracted with diethyl ether (1×50 mL) to remove any neutral impurities. The aqueous layer was then acidified with a 1N aqueous hydrochloric acid solution, and the resulting acid was extracted into ethyl acetate (2×50 mL). The combined organic layers were washed with a saturated aqueous sodium chloride solution (1×100 mL), dried over anhydrous magnesium sulfate, filtered, and concentrated in vacuo to afford (E)-3-cyclopentyl-2-[3-fluoro-4-(5-methyl-tetrazol-1-yl)-phenyl]-acrylic acid (690 mg, 100%) as a white solid: mp 182–185° C.; EI-HRMS m/e calcd for $C_{16}H_{17}FN_4O_2$ ($M^+$) 316.1336, found 316.1334.

A solution of triphenylphosphine (262 mg, 1 mmol) in methylene chloride (6 mL) was cooled to 0° C. and then treated with N-bromosuccinimide (178 mg, 1 mmol). The reaction mixture was stirred at 0° C. for 30 min and then treated with (E)-3-cyclopentyl-2-[3-fluoro-4-(5-methyl-tetrazol-1-yl)-phenyl]-acrylic acid (158 mg, 0.5 mmol). The reaction mixture was stirred for 15 min at 0° C. and then allowed to warm to 25° C. where it was stirred for 1.5 h. The reaction mixture was then treated with 2-amino-5-bromopyridine (260 mg, 1.5 mmol), and the resulting suspension was stirred for 2 d at 25° C. The reaction mixture was then concentrated in vacuo to remove methylene chloride, and the residue was diluted with ethyl acetate (20 mL) and water (30 mL). The two layers were separated, and the aqueous layer was extracted with ethyl acetate (1×15 mL). The combined organic extracts were successively washed with a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40S, Silica, 3/1 hexanes/ethyl acetate) afforded (E)-N-(5-bromo-pyridin-2-yl)-3-cyclopentyl-2-[3-fluoro-4-(5-methyl-tetrazol-1-yl)-phenyl]-acrylamide (66 mg, 28%) as an amorphous white solid: EI-HRMS m/e calcd for $C_{21}H_{20}BrFN_6OS$ ($M^+$) 470.0866, found 470.0864.

EXAMPLE 14

(E)-2-[3-Chloro-4-(5-methyl-tetrazol-1-yl)-phenyl]-3-cyclopentyl-N-thiazol-2-yl-acrylamide

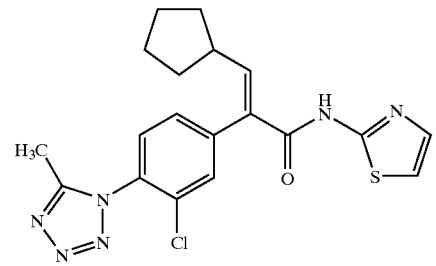

A solution of 2-chloro-4-iodoaniline (25 g, 96.66 mmol) in tetrahydrofuran (100 mL) was cooled to 0° C. and then treated with acetic anhydride (50.6 g, 500 mmol). The reaction mixture was stirred at 0° C. for 10 min and then allowed to warm to 25° C. where it was stirred for 15 h. The reaction mixture was then concentrated in vacuo to remove tetrahydrofuran. The residue was crystallized from ether (50 mL) and hexanes (50 mL). The solids were collected and washed with hexanes to afford N-(2-chloro-4-iodo-phenyl)-acetamide (23.87 g, 84%) as a white crystalline solid: EI-HRMS m/e calcd for $C_8H_7ClINO$ ($M^+$) 295.1526, found 295.1532.

A suspension of N-(2-chloro-4-iodo-phenyl)-acetamide (2.39 g, 8.09 mmol) in acetonitrile (40 mL) at 25° C. was treated with methylene chloride (5 mL) to obtain a clear solution. The resulting solution was then treated with sodium azide (1.05 g, 16.18 mmol), and the reaction mixture was cooled to 0° C. The reaction mixture was then treated with trifluoromethanesulfonic anhydride (3.42 g, 12.13 mmol), and the resulting reaction mixture was allowed to warm to 25° C. where it was stirred overnight. The reaction mixture was then concentrated in vacuo. The residue was diluted with ethyl acetate (50 mL) and water (50 mL), and the two layers were separated. The aqueous layer was further extracted with ethyl acetate (1×30 mL). The combined organic layers were washed with a saturated aqueous sodium chloride solution (1×100 mL), dried over anhydrous magnesium sulfate, filtered, and concentrated in vacuo. Biotage chromatography (FLASH 40M, Silica, 4/1 hexanes/ethyl acetate) afforded 1-(2-chloro-4-iodo-phenyl)-5-methyl-1H-tetrazole (1.53 g, 59%) as a white solid: mp 128–130.5° C.; EI-HRMS m/e calcd for $C_8H_6ClIN_4$ ($M^+$) 319.9327, found 319.9325.

A mixture of lithium chloride (8.48 g, 200 mmol, predried at 130° C. under high vacuum for 3 h) and copper cyanide (8.96 g, 100 mmol) in dry tetrahydrofuran (100 mL) was stirred at 25° C. under argon for 10 min to obtain a clear solution. The reaction mixture was then cooled to -70° C. and then slowly treated with a 2.0M solution of cyclopentylmagnesium chloride in diethyl ether (55 mL, 110 mmol). After the addition, the reaction mixture was allowed to warm to −30° C. where it was stirred for 5 min. The resulting reaction mixture was again cooled back to −70° C. and then slowly treated with methyl propiolate (7.99 g, 95 mmol). The reaction mixture was * stirred overnight at −60° C. to −50° C. The reaction mixture was then slowly treated with a solution of iodine (34.3 g, 135 mmol) in dry tetrahydrofuran (30 mL), with the temperature kept at −70° C. to −60° C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (200 mL) and ammonium hydroxide (50 mL), and the organic compound was extracted into diethyl ether (3×100 mL). The combined organic extracts were successively washed with a saturated aqueous sodium thiosulfate solution (1×300 mL) and a saturated aqueous sodium chloride solution (1×300 mL). The organic layer was then dried over anhydrous magnesium sulfate, filtered, and concentrated in vacuo. Flash chromatography (Merck Silica gel 60, 230–400 mesh, 20/1 hexanes/diethyl ether) afforded (E)-3-cyclopentyl-2-iodo-acrylic acid methyl ester (25.8 g, 97%) as a yellow oil: EI-HRMS m/e calcd for $C_9H_{13}IO_2$ ($M^+$) 279.9960, found 279.9961.

A mixture of zinc dust (650 mg, 10 mmol, Aldrich, −325 mesh) and dry tetrahydrofuran (1 mL) under argon was treated with 1,2-dibromoethane (187 mg, 1 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (108 mg, 1 mmol), and the suspension was stirred for 15 min at 25° C. The reaction mixture was then treated dropwise with a solution of (E)-3-cyclopentyl-2-iodo-acrylic acid methyl ester (1.26 g, 4.5 mmol) in dry tetrahydrofuran (2 mL) over 3 min. The reaction mixture was then stirred at 40–45° C. for 1 h and then stirred overnight at 25° C. The reaction mixture was then diluted with dry tetrahydrofuran (3 mL), and the stirring was stopped to allow the excess zinc dust to settle down (~2 h). In a separate reaction flask, bis(dibenzylideneacetone)-palladium(0) (54 mg, 0.1 mmol) and triphenylphosphine (104 mg, 0.4 mmol) in dry tetrahydrofuran (4 mL) was stirred at 25° C. under argon for 10 min and then treated with 1-(2-chloro-4-iodo-phenyl)-5-methyl-1H-tetrazole (875 mg, 2.73 mmol) and the freshly prepared zinc compound in tetrahydrofuran. The resulting brick red solution was stirred at 25° C. over the weekend and then heated at 40–45° C. for 4 h. The reaction mixture was cooled to 25° C. and then poured into a saturated aqueous ammonium chloride solution (50 mL), and the organic compound was extracted into ethyl acetate (3×35 mL). The combined organic extracts were washed with a saturated aqueous sodium chloride solution (1×100 mL), dried over anhydrous magnesium sulfate, filtered, and concentrated in vacuo. Flash chromatography (Merck Silica gel 60, 230–400 mesh, 4/1 to 1/1 hexanes/ethyl acetate) afforded (E)-2-[3-chloro-4-(5-methyl-tetrazol-1-yl)-phenyl]-3-cyclopentyl-acrylic acid methyl ester (859 mg, 91%) as a light yellow semi-solid: EI-HRMS m/e calcd for $C_{17}H_{19}ClN_4O_2$ ($M^+$) 346.1196, found 346.1190.

A solution of (E)-2-[3-chloro-4-(5-methyl-tetrazol-1-yl)-phenyl]-3-cyclopentyl-acrylic acid methyl ester (160 mg, 0.46 mmol) in ethanol (5 mL) was treated with a 1N aqueous sodium hydroxide solution (1 mL). The solution was heated at 45–50° C. for 15 h, at which time, thin layer chromatography analysis of the reaction mixture indicated the absence of starting material. The reaction mixture was concentrated in vacuo to remove ethanol. The residue was diluted with water (10 mL) and extracted with diethyl ether (1×30 mL) to remove any neutral impurities. The aqueous layer was then acidified with a 1N aqueous hydrochloric acid solution, and the resulting acid was extracted into ethyl acetate (2×20 mL). The combined organic layers were washed with a saturated aqueous sodium chloride solution (1×50 mL), dried over anhydrous magnesium sulfate, filtered, and concentrated in vacuo to afford (E)-2-[3-chloro-4-(5-methyl-tetrazol-1-yl)-phenyl]-3-cyclopentyl-acrylic acid (155 mg, 100%) as a white solid: mp 216–219° C.; EI-HRMS m/e calcd for $C_{16}H_{17}ClN_4O_2$ ($M^+$) 332.1040, found 332.1048.

A solution of triphenylphosphine (165 mg, 0.63 mmol) in methylene chloride (5 mL) was cooled to 0° C. and then treated with N-bromosuccinimide (112 mg, 0.63 mmol). The reaction mixture was stirred at 0° C. for 30 min and then treated with a solution of (E)-2-[3-chloro-4-(5-methyl-tetrazol-1-yl)-phenyl]-3-cyclopentyl-acrylic acid (123 mg, 0.37 mmol) in methylene chloride (3 mL). The reaction mixture was stirred for 15 min at 0° C. and then allowed to warm to 25° C. where it was stirred for 1.5 h. The reaction mixture was then treated with 2-aminothiazole (92.5 mg, 0.93 mmol), and the resulting suspension was stirred for 2 d at 25° C. The reaction mixture was then concentrated in vacuo to remove methylene chloride, and the residue was diluted with ethyl acetate (20 mL) and a 1N aqueous hydrochloric acid solution (30 mL). The two layers were separated, and the aqueous layer was extracted with ethyl acetate (1×15 mL). The combined organic extracts were successively washed with a 1N aqueous hydrochloric acid solution (1×50 mL), a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40S, Silica, 1/1 hexanes/ethyl acetate) afforded (E)-2-[3-chloro-4-(5-methyl-tetrazol-1-yl)-phenyl]-3-cyclopentyl-N-thiazol-2-yl-acrylamide (36 mg, 23%) as an amorphous solid: EI-HRMS m/e calcd for $C_{19}H_{19}ClN_6OS$ ($M^+$) 414.1029, found 414.1029.

EXAMPLE 15

(E)-2-[3-Chloro-4-(5-methyl-tetrazol-1-yl)-phenyl]-3-cyclohexyl-N-thiazol-2-yl-acrylamide

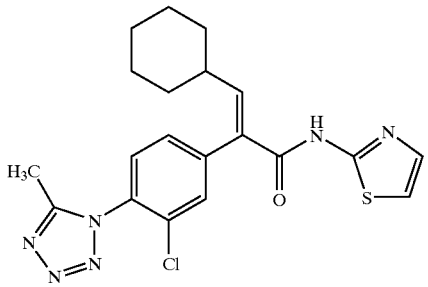

A suspension of triphenylphospine (11.7 g, 44.8 mmol) in carbon tetrachloride (8 mL, 83 mmol) was cooled to 0° C. and then treated with triethylamine (2.5 mL, 18 mmol) and acetic acid (115 mL, 20 mmol). The reaction mixture was stirred at 0° C. for 10 min and then treated with a solution of 2-chloro-4-iodoaniline (5.07 g, 20 mmol) in carbon tetrachloride (12 mL, heated to obtain a solution). The resulting light brown suspension was allowed to warm to 25° C. and then it was refluxed overnight. The reaction mixture was cooled to 25° C. and then concentrated in vacuo. The resulting solid residue was then diluted with hexanes (50 mL) and methylene chloride (50 mL). The precipitated solid was collected by filtration and washed with hexanes. The filtrate was concentrated in vacuo, and the resulting residue was diluted with diethyl ether (100 mL). The precipitated solid was collected by filtration and washed with hexanes, and the filtrate was concentrated in vacuo. The resulting residue was again diluted with hexanes (100 mL), and the precipitated solid was collected by filtration. The filtrate was finally concentrated in vacuo to afford the imidoyl chloride intermediate (4.08 g) as a liquid. This crude imidoyl chloride intermediate (4.08 g, ~13 mmol) was treated with sodium azide (1.04 g, 16 mmol) and acetic acid (10 mL). The reaction was exothermic, and the resulting reaction mixture was stirred for 1h at 25° C. The reaction mixture was then heated at 70° C. for 2 h, at which time, thin layer chromatography analysis of the reaction mixture indicated the absence of the imidoyl chloride intermediate. The cloudy yellow suspension was cooled to 25° C. and then diluted with water (100 mL) and extracted with ethyl acetate (2×75 mL). The combined organic extracts were washed successively with a saturated aqueous sodium bicarbonate solution (1×100 mL) and a saturated aqueous sodium chloride solution (1×100 mL), dried over anhydrous magnesium sulfate, filtered, and concentrated in vacuo. Biotage chromatography (FLASH 40M, Silica, 6/1 hexanes/diethyl ether) afforded 1-(2-chloro-4-iodo-phenyl)-5-methyl-1H-tetrazole (350 mg, 6%) as a white solid: mp 128–130.5° C.; EI-HRMS m/e calcd for $C_8H_6ClIN_4$ (M$^+$) 319.9327, found 319.9325.

A mixture of zinc dust (16.34 g, 250 mmol, Aldrich, -325 mesh) and dry tetrahydrofuran (6 mL) under argon was treated with 1,2-dibromoethane (0.94 g, 5 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (0.54 g, 5 mmol), and the suspension was stirred for 15 min at 25° C. The reaction mixture was then treated dropwise with a solution of cyclohexyl iodide (21 g, 100 mmol) in dry tetrahydrofuran (30 mL) over 15 min. During the addition, the temperature rose to 60° C. The reaction mixture was then stirred for 3 h at 40–45° C. The reaction mixture was then cooled to 25° C. and diluted with dry tetrahydrofuran (60 mL). The stirring was stopped to allow the excess zinc dust to settle down (~3 h). In a separate reaction flask, a mixture of lithium chloride (8.48 g, 200 mmol, predried at 130° C. under high vacuum for 3 h) and copper cyanide (8.95 g, 100 mmol) in dry tetrahydrofuran (110 mL) was stirred for 10 min at 25° C. to obtain a clear solution. The reaction mixture was cooled to −70° C. and then slowly treated with the freshly prepared zinc solution using a syringe. After the addition, the reaction mixture was allowed to warm to 0° C. where it was stirred for 5 min. The reaction mixture was again cooled back to −70° C. and then slowly treated with methyl propiolate (7.56 g, 90 mmol). The resulting reaction mixture was stirred for 15 h at −70° C. to −50° C. and then slowly treated with a solution of iodine (34.26 g, 135 mmol) in dry tetrahydrofuran (30 mL), with the temperature kept at −70° C. to −60° C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (400 mL) and ammonium hydroxide (100 mL), and the organic compound was extracted into ethyl acetate (3×250 mL). The combined organic extracts were successively washed with a saturated aqueous sodium thiosulfate solution (1×500 mL) and a saturated aqueous sodium chloride solution (1×500 mL), dried over anhydrous magnesium sulfate, filtered, and concentrated in vacuo. Flash chromatography (Merck Silica gel 60, 230–400 mesh, 9/1 hexanes/diethyl ether) afforded (E)-3-cyclohexyl-2-iodo-acrylic acid methyl ester (26.3 g, 99%) as a light pink oil: EI-HRMS m/e calcd for $C_{10}H_{15}IO_2$ (M$^+$) 294.0117, found 294.0114.

A mixture of zinc dust (320 mg, 5 mmol, Aldrich, -325 mesh) and dry tetrahydrofuran (1 mL) under argon was treated with 1,2-dibromoethane (94 mg, 0.5 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (55 mg, 0.5 mmol), and the suspension was stirred for 15 min at 25° C. The reaction mixture was then treated dropwise with a solution of (E)-3-cyclohexyl-2-iodo-acrylic acid methyl ester (588 mg, 2 mmol) in dry tetrahydrofuran (2 mL). After the addition, the reaction mixture was stirred for 1 h at 40–45° C. and then stirred overnight at 25° C. The reaction mixture was then diluted with dry tetrahydrofuran (2 mL), and the stirring was stopped to allow the excess zinc dust to settle down (~2 h). In a separate reaction flask, bis(dibenzylideneacetone) palladium(0) (27 mg, 0.05 mmol) and triphenylphosphine (57 mg, 0.2 mmol) in dry tetrahydrofuran (4 mL) was stirred at 25° C. under argon for 10 min and then treated with 1-(2-chloro-4-iodo-phenyl)-5-methyl-1H-tetrazole (320.5 mg, 1 mmol) and the freshly prepared zinc compound in tetrahydrofuran. The resulting brick red solution was heated at 50° C. for 15 h. The reaction mixture was cooled to 25° C. and then poured into a saturated aqueous ammonium chloride solution (30 mL), and the organic compound was extracted into ethyl acetate (3×20 mL). The combined organic extracts were washed with a saturated aqueous sodium chloride solution (1×50 mL), dried over anhydrous magnesium sulfate, filtered, and concentrated in vacuo. Biotage chromatography (FLASH 40S, Silica, 4/1/1 hexanes/ethyl acetate/methylene chloride) afforded (E)-2-[3-chloro-4-(5-methyl-tetrazol-1-yl)-phenyl]-3-cyclohexyl-acrylic acid methyl ester (233 mg, 64%) as an amorphous white solid: EI-HRMS m/e calcd for $C_{18}H_{21}ClN_4O_2$ (M$^+$) 360.1353, found 360.1354.

A solution of (E)-2-[3-chloro-4-(5-methyl-tetrazol-1-yl)-phenyl]-3-cyclohexyl-acrylic acid methyl ester (209 mg, 0.58 mmol) in ethanol (3 mL) was treated with a 1N aqueous sodium hydroxide solution (1.2 mL). The solution was heated at 45–50° C. for 15 h, at which time, thin layer chromatography analysis of the mixture indicated the absence of starting material. The reaction mixture was then concentrated in vacuo to remove ethanol, and the residue was diluted with water (10 mL) and extracted with diethyl ether (1×30 mL) to remove any neutral impurities. The aqueous layer was acidified with a 1N aqueous hydrochloric acid solution. The resulting acid was extracted into ethyl acetate (2×20 mL). The combined organic layers were washed with a saturated aqueous sodium chloride solution (1×50 mL), dried over anhydrous magnesium sulfate, filtered, and concentrated in vacuo to afford (E)-2-[3-chloro-4-(5-methyl-tetrazol-1-yl)-phenyl]-3-cyclohexyl-acrylic acid (203 mg, 99%) as a brown solid: FAB-HRMS m/e calcd for $C_{17}H_{19}ClN_4O_2$ $(M+H)^+$ 347.1275, found 347.1283.

A solution of triphenylphosphine (290 mg, 1.1 mmol) in methylene chloride (5 mL) was cooled to 0° C. and then treated with N-bromosuccinimide (195 mg, 1.1 mmol). The reaction mixture was stirred at 0° C. for 30 min and then treated with a solution of (E)-2-[3-chloro-4-(5-methyl-tetrazol-1-yl)-phenyl]-3-cyclohexyl-acrylic acid (192 mg, 0.55 mmol) in methylene chloride (3 mL). The reaction mixture was stirred for 15 min at 0° C. and then allowed to warm to 25° C. where it was stirred for 1.5 h. The reaction mixture was then treated with 2-aminothiazole (166 mg, 1.66 mmol), and the resulting suspension was stirred for 2 d at 25° C. The reaction mixture was concentrated in vacuo to remove methylene chloride, and the residue was diluted with ethyl acetate (40 mL) and a 1N aqueous hydrochloric acid solution (30 mL). The two layers were separated, and the aqueous layer was extracted with ethyl acetate (1×25 mL). The combined organic extracts were successively washed with a 1N aqueous hydrochloric acid solution (1×50 mL), a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40S, Silica, 7/3 to 2/3 hexanes/ethyl acetate) afforded (E)-2-[3-chloro-4-(5-methyl-tetrazol-1-yl)-phenyl]-3-cyclohexyl-N-thiazol-2-yl-acrylamide (86 mg, 36%) as an amorphous solid: EI-HRMS m/e calcd for $C_{20}H_{21}ClN_6OS$ $(M^+)$ 428.1186, found 428.1189.

EXAMPLE 16

(E)-2-[3-Chloro-4-(5-methyl-tetrazol-1-yl)-phenyl]-3-cycloheptyl-N-thiazol-2-yl-acrylamide

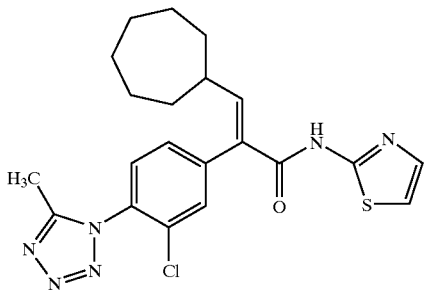

A solution of 2-chloro-4-iodoaniline (25 g, 96.66 mmol) in tetrahydrofuran (100 mL) was cooled to 0° C. and then treated with acetic anhydride (50.6 g, 500 mmol). The reaction mixture was stirred at 0° C. for 10 min and then allowed to warm to 25° C. where it was stirred for 15 h. The reaction mixture was then concentrated in vacuo to remove tetrahydrofuran. The residue was crystallized from ether (50 mL) and hexanes (50 mL). The solids were collected and washed with hexanes to afford N-(2-chloro-4-iodo-phenyl)-acetamide (23.87 g, 84%) as a white crystalline solid: EI-HRMS m/e calcd for $C_8H_7ClINO$ $(M^+)$ 295.1526, found 295.1532.

A suspension of N-(2-chloro-4-iodo-phenyl)-acetamide (2.39 g, 8.09 mmol) in acetonitrile (40 mL) at 25° C. was treated with methylene chloride (5 mL) to obtain a clear solution. The resulting solution was then treated with sodium azide (1.05 g, 16.18 mmol), and the reaction mixture was cooled to 0° C. The reaction mixture was then treated with trifluoromethanesulfonic anhydride (3.42 g, 12.13 mmol), and the resulting reaction mixture was allowed to warm to 25° C. where it was stirred overnight. The reaction mixture was then concentrated in vacuo. The residue was diluted with ethyl acetate (50 mL) and water (50 mL), and the two layers were separated. The aqueous layer was further extracted with ethyl acetate (1×30 mL). The combined organic layers were washed with a saturated aqueous sodium chloride solution (1×100 mL), dried over anhydrous magnesium sulfate, filtered, and concentrated in vacuo. Biotage chromatography (FLASH 40M, Silica, 4/1 hexanes/ethyl acetate) afforded 1-(2-chloro-4-iodo-phenyl)-5-methyl-1H-tetrazole (1.53 g, 59%) as a white solid: mp 128–130.5° C.; EI-HRMS rn/e calcd for $C_8H_6ClIN_4$ $(M^+)$ 319.9327, found 319.9325.

A mixture of magnesium metal (4.81 g, 200 mmol) and dry tetrahydrofuran (10 mL) under argon was treated with a solution of 1,2-dibromoethane (0.94 g, 5 mmol) in dry tetrahydrofuran (5 mL). The resulting reaction mixture was stirred for 10 min to activate the magnesium metal. The reaction mixture was then treated dropwise with a solution of cycloheptyl bromide (17.7 g, 100 mmol) in dry tetrahydrofuran (30 mL), one-fifth portion over a period of 5 min. The resulting reaction mixture was stirred for 5–10 min to initiate the exothermic reaction. The remaining portion of the cycloheptyl bromide solution was then added dropwise while controlling the inside temperature below 50° C. After complete addition, the solution was stirred for 1 h and then diluted with dry tetrahydrofuran (80 mL). In a separate reaction flask, a mixture of lithium chloride (8.48 g, 200 mmol, predried at 130° C. under high vacuum for 3 h) and copper cyanide (8.96 g, 100 mmol) in dry tetrahydrofuran (110 mL) was stirred at 25° C. under argon for 10 min to obtain a clear solution. The reaction mixture was cooled to −70° C. and then slowly treated with the freshly prepared cycloheptylmagnesium bromide. After the addition, the reaction mixture was allowed to warm to −10° C. where it was stirred for 5 min. The resulting reaction mixture was again cooled back to −70° C. and then treated with methyl propiolate (7.57 g, 90 mmol). The reaction mixture was stirred for 15 h at −70° C. to −50° C. and then slowly treated with a solution of iodine (34.3 g, 135 mmol) in dry tetrahydrofuran (30 mL), with the temperature kept at −70° C. to −60° C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (400 mL) and ammonium hydroxide (100 mL), and the organic compound was extracted into ethyl acetate (3×200 mL). The combined organic extracts were successively washed with a saturated aqueous sodium thiosulfate solution (1×400 mL) and a saturated aqueous sodium chloride solution (1×400 mL). The organic layer was then dried over anhydrous magnesium sulfate, filtered, and concentrated in vacuo. Flash chromatography (Merck Silica gel 60, 230–400 mesh, 20/1 to 10/1 hexanes/diethyl ether) afforded (E)-3-cycloheptyl-2-iodo-acrylic acid methyl ester (17.86 g, 64%) as a colorless oil: EI-HRMS m/e calcd for $C_{11}H_{17}IO_2$ ($M^+$) 308.0273, found 308.0273.

A mixture of zinc dust (980 mg, 15 mmol, Aldrich, -325 mesh) and dry tetrahydrofuran (1 mL) under argon was treated with 1,2-dibromoethane (280 mg, 1.5 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (162 mg, 1.5 mmol), and the suspension was stirred for 15 min at 25° C. The reaction mixture was then treated dropwise with a solution of (E)-3-cycloheptyl-2-iodo-acrylic acid methyl ester (1.54 g, 5 mmol) in dry tetrahydrofuran (3 mL). The reaction mixture was then stirred at 40–45° C. for 1 h and then stirred overnight at 25° C. The reaction mixture was then diluted with dry tetrahydrofuran (5 mL), and the stirring was stopped to allow the excess zinc dust to settle down (~2 h). In a separate reaction flask, bis(dibenzylideneacetone) palladium(0) (81 mg, 0.15 mmol) and triphenylphosphine (156 mg, 0.6 mmol) in dry tetrahydrofuran (12 mL) was stirred at 25° C. under argon for 10 min and then treated with 1-(2-chloro-4-iodo-phenyl)-5-methyl-1H-tetrazole (1.28 g, 4 mmol) and the freshly prepared zinc compound in tetrahydrofuran. The resulting brick red solution was heated at 45–50° C. for 20 h. The reaction mixture was cooled to 25° C. and then poured into a saturated aqueous ammonium chloride solution (100 mL), and the organic compound was extracted into ethyl acetate (3×50 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 4/1 to 1/1 hexanes/ethyl acetate) afforded (E)-2-[3-chloro-4-(5-methyl-tetrazol-1-yl)-phenyl]-3-cycloheptyl-acrylic acid methyl ester (1.29 g, 85%) as a yellow oil: EI-HRMS m/e calcd for $C_{19}H_{23}ClN_4O_2$ ($M^+$) 374.1509, found 374.1509.

A solution of (E)-2-[3-chloro-4-(5-methyl-tetrazol-1-yl)-phenyl]-3-cycloheptyl-acrylic acid methyl ester (1.20 g, 3.2 mmol) in ethanol (15 mL) was treated with a 1N aqueous sodium hydroxide solution (6.5 mL). The solution was heated at 45–50° C. for 15 h, at which time, thin layer chromatography analysis of the reaction mixture indicated the absence of starting material. The reaction mixture was concentrated in vacuo to remove ethanol. The residue was diluted with water (50 mL) and extracted with diethyl ether (1×50 mL) to remove any neutral impurities. The aqueous layer was then acidified with a 1N aqueous hydrochloric acid solution, and the resulting acid was extracted into ethyl acetate (2×70 mL). The combined organic layers were washed with a saturated aqueous sodium chloride solution (1×50 mL), dried over anhydrous magnesium sulfate, filtered, and concentrated in vacuo to afford (E)-2-[3-chloro-4-(5-methyl-tetrazol-1-yl)-phenyl]-3-cycloheptyl-acrylic acid (1.01 g, 87%) as a white solid.

A solution of triphenylphosphine (1.45 g, 5.54 mmol) in methylene chloride (15 mL) was cooled to 0° C. and then treated with N-bromosuccinimide (986 mg, 5.54 mmol). The reaction mixture was stirred at 0° C. for 30 min and then treated with a solution of (E)-2-[3-chloro-4-(5-methyl-tetrazol-1-yl)-phenyl]-3-cycloheptyl-acrylic acid (1.00 g, 2.77 mmol) in methylene chloride (5 mL). The reaction mixture was stirred for 15 min at 0° C. and then allowed to warm to 25° C. where it was stirred for 1.5 h. The reaction mixture was then treated with 2-aminothiazole (832 g, 8.32 mmol), and the resulting suspension was stirred for 3 d at 25° C. The reaction mixture was then concentrated in vacuo to remove methylene chloride, and the residue was diluted with ethyl acetate (50 mL) and water (50 mL). The two layers were separated, and the aqueous layer was extracted with ethyl acetate (1×50 mL). The combined organic extracts were successively washed with a saturated aqueous sodium bicarbonate solution (1×100 mL) and a saturated aqueous sodium chloride solution (1×100 mL), dried over anhydrous magnesium sulfate, filtered, and concentrated in vacuo. Biotage chromatography (FLASH 40M, Silica, 1/1 hexanes/ethyl acetate) afforded (E)-2-[3-chloro-4-(5-methyl-tetrazol-1-yl)-phenyl]-3-cycloheptyl-N-thiazol-2-yl-acrylamide (810 mg, 66%) as an amorphous white solid: EI-HRMS m/e calcd for $C_{21}H_{23}ClN_6OS$ ($M^+$) 442.1343, found 442.1343.

EXAMPLE 17

(E)-N-(5-Bromo-thiazol-2-yl)-2-[3-chloro-4-(5-methyl-tetrazol-1-yl)-phenyl]-3-cycloheptyl-acrylamide

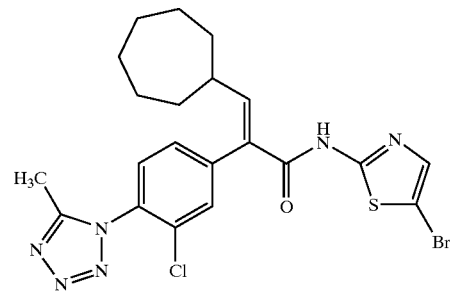

A solution of 2-chloro-4-iodoaniline (25 g, 96.66 mmol) in tetrahydrofuran (100 mL) was cooled to 0° C. and then treated with acetic anhydride (50.6 g, 500 mmol). The reaction mixture was stirred at 0° C. for 10 min and then allowed to warm to 25° C. where it was stirred for 15 h. The reaction mixture was then concentrated in vacuo to remove tetrahydrofuran. The residue was crystallized from ether (50 mL) and hexanes (50 mL). The solids were collected and washed with hexanes to afford N-(2-chloro-4-iodo-phenyl)-acetamide (23.87 g, 84%) as a white crystalline solid: EI-HRMS m/e calcd for $C_8H_7ClINO$ ($M^+$) 295.1526, found 295.1532.

A suspension of N-(2-chloro-4-iodo-phenyl)-acetamide (2.39 g, 8.09 mmol) in acetonitrile (40 mL) at 25° C. was treated with methylene chloride (5 mL) to obtain a clear solution. The resulting solution was then treated with sodium azide (1.05 g, 16.18 mmol), and the reaction mixture was cooled to 0° C. The reaction mixture was then treated with trifluoromethanesulfonic anhydride (3.42 g, 12.13 mmol), and the resulting reaction mixture was allowed to warm to 25° C. where it was stirred overnight. The reaction mixture was then concentrated in vacuo. The residue was diluted with ethyl acetate (50 mL) and water (50 mL), and the two layers were separated. The aqueous layer was further extracted with ethyl acetate (1×30 mL). The combined organic layers were washed with a saturated aqueous sodium chloride solution (1×100 mL), dried over anhydrous magnesium sulfate, filtered, and concentrated in vacuo. Biotage chromatography (FLASH 40M, Silica, 4/1 hexanes/ethyl acetate) afforded 1-(2-chloro-4-iodo-phenyl)-5-methyl-1H-tetrazole (1.53 g, 59%) as a white solid: mp 128–130.5° C.; EI-HRMS m/e calcd for $C_8H_6ClIN_4$ ($M^+$) 319.9327, found 319.9325.

A mixture of magnesium metal (4.81 g, 200 mmol) and dry tetrahydrofuran (10 mL) under argon was treated with a solution of 1,2-dibromoethane (0.94 g, 5 mmol) in dry tetrahydrofuran (5 mL). The resulting reaction mixture was stirred for 10 min to activate the magnesium metal. The reaction mixture was then treated dropwise with a solution of cycloheptyl bromide (17.7 g, 100 mmol) in dry tetrahydrofuran (30 mL), one-fifth portion over a period of 5 min. The resulting reaction mixture was stirred for 5–10 min to initiate the exothermic reaction. The remaining portion of the cycloheptyl bromide solution was then added dropwise while controlling the inside temperature below 50° C. After complete addition, the solution was stirred for 1 h and then diluted with dry tetrahydrofuran (80 mL). In a separate reaction flask, a mixture of lithium chloride (8.48 g, 200 mmol, predried at 130° C. under high vacuum for 3 h) and copper cyanide (8.96 g, 100 mmol) in dry tetrahydrofuran (110 mL) was stirred at 25° C. under argon for 10 min to obtain a clear solution. The reaction mixture was cooled to −70° C. and then slowly treated with the freshly prepared cycloheptylmagnesium bromide. After the addition, the reaction mixture was allowed to warm to −10° C. where it was stirred for 5 min. The resulting reaction mixture was again cooled back to −70° C. and then treated with methyl propiolate (7.57 g, 90 mmol). The reaction mixture was stirred for 15 h at −70° C. to −50° C. and then slowly treated with a solution of iodine (34.3 g, 135 mmol) in dry tetrahydrofuran (30 mL), with the temperature kept at −70° C. to −60° C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (400 mL) and ammonium hydroxide (100 mL), and the organic compound was extracted into ethyl acetate (3×200 mL). The combined organic extracts were successively washed with a saturated aqueous sodium thiosulfate solution (1×400 mL) and a saturated aqueous sodium chloride solution (1×400 mL). The organic layer was then dried over anhydrous magnesium sulfate, filtered, and concentrated in vacuo. Flash chromatography (Merck Silica gel 60, 230–400 mesh, 20/1 to 10/1 hexanes/diethyl ether) afforded (E)-3-cycloheptyl-2-iodo-acrylic acid methyl ester (17.86 g, 64%) as a colorless oil: EI-HRMS m/e calcd for $C_{11}H_{17}IO_2$ ($M^+$) 308.0273, found 308.0273.

A mixture of zinc dust (980 mg, 15 mmol, Aldrich, −325 mesh) and dry tetrahydrofuran (1 mL) under argon was treated with 1,2-dibromoethane (280 mg, 1.5 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (162 mg, 1.5 mmol), and the suspension was stirred for 15 min at 25° C. The reaction mixture was then treated dropwise with a solution of (E)-3-cycloheptyl-2-iodo-acrylic acid methyl ester (1.54 g, 5 mmol) in dry tetrahydrofuran (3 mL). The reaction mixture was then stirred at 40–45° C. for 1 h and then stirred overnight at 25° C. The reaction mixture was then diluted with dry tetrahydrofuran (5 mL), and the stirring was stopped to allow the excess zinc dust to settle down (~2 h). In a separate reaction flask, bis(dibenzylideneacetone) palladium(0) (81 mg, 0.15 mmol) and triphenylphosphine (156 mg, 0.6 mmol) in dry tetrahydrofuran (12 mL) was stirred at 25° C. under argon for 10 min and then treated with 1-(2-chloro-4-iodo-phenyl)-5-methyl-1H-tetrazole (1.28 g, 4 mmol) and the freshly prepared zinc compound in tetrahydrofuran. The resulting brick red solution was heated at 45–50° C. for 20 h. The reaction mixture was cooled to 25° C. and then poured into a saturated aqueous ammonium chloride solution (100 mL), and the organic compound was extracted into ethyl acetate (3×50 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 4/1 to 1/1 hexanes/ethyl acetate) afforded (E)-2-[3-chloro-4-(5-methyl-tetrazol-1-yl)-phenyl]-3-cycloheptyl-acrylic acid methyl ester (1.29 g, 85%) as a yellow oil: EI-HRMS m/e calcd for $C_{19}H_{23}ClN_4O_2$ ($M^+$) 374.1509, found 374.1509.

A solution of (E)-2-[3-chloro-4-(5-methyl-tetrazol-1-yl)-phenyl]-3-cycloheptyl-acrylic acid methyl ester (1.20 g, 3.2 mmol) in ethanol (15 mL) was treated with a 1N aqueous sodium hydroxide solution (6.5 mL). The solution was heated at 45–50° C. for 15 h, at which time, thin layer chromatography analysis of the reaction mixture indicated the absence of starting material. The reaction mixture was concentrated in vacuo to remove ethanol. The residue was diluted with water (50 mL) and extracted with diethyl ether (1×50 mL) to remove any neutral impurities. The aqueous layer was then acidified with a 1N aqueous hydrochloric acid solution, and the resulting acid was extracted into ethyl acetate (2×70 mL). The combined organic layers were washed with a saturated aqueous sodium chloride solution (1×50 mL), dried over anhydrous magnesium sulfate, filtered, and concentrated in vacuo to afford (E)-2-[3-chloro-4-(5-methyl-tetrazol-1-yl)-phenyl]-3-cycloheptyl-acrylic acid (1.01 g, 87%) as a white solid.

A solution of triphenylphosphine (1.45 g, 5.54 mmol) in methylene chloride (15 mL) was cooled to 0° C. and then treated with N-bromosuccinimide (986 mg, 5.54 mmol). The reaction mixture was stirred at 0° C. for 30 min and then treated with a solution of (E)-2-[3-chloro-4-(5-methyl-tetrazol-1-yl)-phenyl]-3-cycloheptyl-acrylic acid (1.00 g, 2.77 mmol) in methylene chloride (5 mL). The reaction mixture was stirred for 15 min at 0° C. and then allowed to warm to 25° C. where it was stirred for 1.5 h. The reaction mixture was then treated with 2-aminothiazole (832 g, 8.32 mmol), and the resulting suspension was stirred for 3 d at 25° C. The reaction mixture was then concentrated in vacuo to remove methylene chloride, and the residue was diluted with ethyl acetate (50 mL) and water (50 mL). The two layers were separated, and the aqueous layer was extracted with ethyl acetate (1×50 mL). The combined organic extracts were successively washed with a saturated aqueous sodium bicarbonate solution (1×100 mL) and a saturated aqueous sodium chloride solution (1×100 mL), dried over anhydrous magnesium sulfate, filtered, and concentrated in vacuo. Biotage chromatography (FLASH 40M, Silica, 1/1 hexanes/ethyl acetate) afforded (E)-2-[3-chloro-4-(5-methyl-tetrazol-1-yl)-phenyl]-3-cycloheptyl-N-thiazol-2-yl-acrylamide (810 mg, 66%) as an amorphous white solid: EI-HRMS m/e calcd for $C_{21}H_{23}ClN_6OS$ ($M^+$) 442.1343, found 442.1343.

A suspension of (E)-2-[3-chloro-4-(5-methyl-tetrazol-1-yl)-phenyl]-3-cycloheptyl-N-thiazol-2-yl-acrylamide (300 mg, 0.69 mmol) and N-bromosuccinimide (123 mg, 0.69 mmol) in carbon tetrachloride (3 mL) at 25° C. was treated with benzoyl peroxide (8.4 mg, 0.035 mmol). The resulting reaction mixture was heated to 90° C. where it was stirred overnight at this temperature. The reaction mixture was allowed to cool to 25° C. and then concentrated in vacuo. The residue was dissolved in ethyl acetate (50 mL). The organic phase was then washed with water (1×50 mL) and a saturated aqueous sodium chloride solution (1×50 mL), dried over anhydrous magnesium sulfate, filtered, and concentrated in vacuo. Biotage chromatography (FLASH 40S, Silica, 4/1 hexanes/ethyl acetate) afforded (E)-N-(5-bromo-thiazol-2-yl)-2-[3-chloro-4-(5-methyl-tetrazol-1-yl)-phenyl]-3 cycloheptyl-acrylamide (118 mg, 33%) as an amorphous solid: EI-HRMS m/e calcd for $C_{21}H_{22}BrClN_6OS$ (M$^+$) 520.0448, found 520.0448.

EXAMPLE 18

(E)-2-[3-Chloro-4-(5-trifluoromethyl-tetrazol-1-yl)-phenyl]-3-cyclohexyl-N-thiazol-2-yl-acrylamide

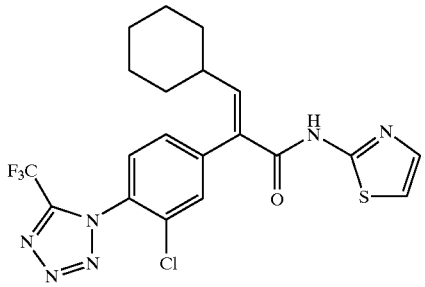

A suspension of triphenylphospine (13.11 g, 50 mmol) in carbon tetrachloride (8 mL, 83 mmol) was cooled to 0° C. and then treated with triethylamine (2.78 mL, 20 mmol) and trifluoroacetic acid (1.3 mL, 16.6 mmol). The reaction mixture was stirred at 0° C. for 10 min and then treated with a solution of 2-chloro-4-iodoaniline (5.07 g, 20 mmol) in carbon tetrachloride (10 mL). The resulting light brown suspension was allowed to warm to 25° C. and then it was refluxed overnight. The reaction mixture was cooled to 25° C. and then concentrated in vacuo. The resulting solid residue was then diluted with hexanes (50 mL) and methylene chloride (50 mL). The precipitated solid was collected by filtration and washed with hexanes. The filtrate was concentrated in vacuo, and the resulting residue was diluted with diethyl ether (100 mL). The precipitated solid was collected by filtration and washed with hexanes, and the filtrate was concentrated in vacuo. The resulting residue was again diluted with hexanes (100 mL), and the precipitated solid was collected by filtration. The filtrate was finally concentrated in vacuo to afford the imidoyl chloride intermediate (5.88 g) as a brown liquid. This crude imidoyl chloride intermediate (5.88 g, ~16 mmol) was treated with sodium azide (1.04 g, 16 mmol) and acetic acid (10 mL). The resulting reaction mixture was then heated at 70° C. for 2 h, at which time, thin layer chromatography analysis of the reaction mixture indicated the absence of the imidoyl chloride intermediate. The cloudy yellow suspension was cooled to 25° C. and then diluted with water (100 mL) and extracted with ethyl acetate (2×75 mL). The combined organic extracts were washed successively with a saturated aqueous sodium bicarbonate solution (1×100 mL) and a saturated aqueous sodium chloride solution (1×100 mL), dried over anhydrous magnesium sulfate, filtered, and concentrated in vacuo. Biotage chromatography (FLASH 40M, Silica, 8/1 hexanes/diethyl ether) afforded 1-(2-chloro-4-iodo-phenyl)-5-trifluoromethyl-1H-tetrazole (5.2 g, 69%) as a light yellow solid: mp 71–73° C.; EI-HRMS m/e calcd for $C_8H_3ClF_3IN_4$ (M$^+$) 373.9043, found 373.9044.

A mixture of zinc dust (16.34 g, 250 mmol, Aldrich, -325 mesh) and dry tetrahydrofuran (6 mL) under argon was treated with 1,2-dibromoethane (0.94 g, 5 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (0.54 g, 5 mmol), and the suspension was stirred for 15 min at 25° C. The reaction mixture was then treated dropwise with a solution of cyclohexyl iodide (21 g, 100 mmol) in dry tetrahydrofuran (30 mL) over 15 min. During the addition, the temperature rose to 60° C. The reaction mixture was then stirred for 3 h at 40–45° C. The reaction mixture was then cooled to 25° C. and diluted with dry tetrahydrofuran (60 mL). The stirring was stopped to allow the excess zinc dust to settle down (~3 h). In a separate reaction flask, a mixture of lithium chloride (8.48 g, 200 mmol, predried at 130° C. under high vacuum for 3 h) and copper cyanide (8.95 g, 100 mmol) in dry tetrahydrofuran (110 mL) was stirred for 10 min at 25° C. to obtain a clear solution. The reaction mixture was cooled to -70° C. and then slowly treated with the freshly prepared zinc solution using a syringe. After the addition, the reaction mixture was allowed to warm to 0° C. where it was stirred for 5 min. The reaction mixture was again cooled back to -70° C. and then slowly treated with methyl propiolate (7.56 g, 90 mmol). The resulting reaction mixture was stirred for 15 h at -70° C. to -50° C. and then slowly treated with a solution of iodine (34.26 g, 135 mmol) in dry tetrahydrofuran (30 mL), with the temperature kept at -70° C. to -60° C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (400 mL) and ammonium hydroxide (100 mL), and the organic compound was extracted into ethyl acetate (3×250 mL). The combined organic extracts were successively washed with a saturated aqueous sodium thiosulfate solution (1×500 mL) and a saturated aqueous sodium chloride solution (1×500 mL), dried over anhydrous magnesium sulfate, filtered, and concentrated in vacuo. Flash chromatography (Merck Silica gel 60, 230–400 mesh, 9/1 hexanes/diethyl ether) afforded (E)-3-cyclohexyl-2-iodo-acrylic acid methyl ester (26.3 g, 99%) as a light pink oil: EI-HRMS m/e calcd for $C_{10}H_{15}IO_2$ (M$^+$) 294.0117, found 294.0114.

A mixture of zinc dust (650 mg, 10 mmol, Aldrich, -325 mesh) and dry tetrahydrofuran (2 mL) under argon was treated with 1,2-dibromoethane (187 mg, 1 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (110 mg, 1 mmol), and the suspension was stirred for 15 min at 25° C. The reaction mixture was then treated dropwise with a solution of (E)-3-cyclohexyl-2-iodo-acrylic acid methyl ester (1.32 g, 4.5 mmol) in dry tetrahydrofuran (2 mL) over 5 min. After the addition, the reaction mixture was stirred for 1 h at 40–45° C. and then stirred overnight at 25° C. The reaction mixture was then diluted with dry tetrahydrofuran (4 mL), and the stirring was stopped to allow the excess zinc dust to settle down (~2 h). In a separate reaction flask, bis(dibenzylideneacetone) palladium(0) (54 mg, 0.1 mmol) and triphenylphosphine (104 mg, 0.4 mmol) in dry tetrahydrofuran (8 mL) was stirred at 25° C. under argon for 10 min and then treated with 1-(2-chloro-4-iodo-phenyl)-5-trifluoromethyl-1H-tetrazole (1.12 g, 3 mmol) and the freshly prepared zinc compound in tetrahydrofuran. The resulting brick red solution was heated at 50° C. for 15 h. The reaction mixture was cooled to 25°

C. and then poured into a saturated aqueous ammonium chloride solution (70 mL), and the organic compound was extracted into ethyl acetate (3×50 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 6/1 hexanes/ethyl acetate) afforded the (E)-2-[3-chloro-4-(5-trifluoromethyl-tetrazol-1-yl)-phenyl]-3-cyclohexyl-acrylic acid methyl ester (908 mg, 73%) as an amorphous white solid: EI-HRMS m/e calcd for $C_{18}H_{18}ClF_3N_4O_2$ (M$^+$) 414.1070, found 414.1075.

A solution of (E)-2-[3-chloro-4-(5-trifluoromethyl-tetrazol-1-yl)-phenyl]-3-cyclohexyl-acrylic acid methyl ester (833 mg, 2 mmol) in ethanol (10 mL) was treated with a 1N aqueous sodium hydroxide solution (4 mL). The solution was heated at 45–50° C. for 15 h, at which time, thin layer chromatography analysis of the mixture indicated the absence of starting material. The reaction mixture was then concentrated in vacuo to remove ethanol, and the residue was diluted with water (20 mL) and extracted with diethyl ether (1×50 mnL) to remove any neutral impurities. The aqueous layer was acidified with a 1N aqueous hydrochloric acid solution. The resulting acid was extracted into ethyl acetate (2×50 mL). The combined organic layers were washed with a saturated aqueous sodium chloride solution (1×100 mL), dried over anhydrous magnesium sulfate, filtered, and concentrated in vacuo to afford (E)-2-[3-chloro-4-(5-trifluoromethyl-tetrazol-1-yl)-phenyl]-3-cyclohexyl-acrylic acid (606 mg, 75%) as a brown solid: FAB-HRMS m/e calcd for $C_{17}H_{16}ClF_3N_4O_2$ (M+H)$^+$ 401.0992, found 401.0987.

A solution of triphenylphosphine (772 mg, 2.96 mmol) in methylene chloride (10 mL) was cooled to 0° C. and then treated with N-bromosuccinimide (526 mg, 2.96 mmol). The reaction mixture was stirred at 0° C. for 30 min and then treated with a solution of (E)-2-[3-chloro-4-(5-trifluoromethyl-tetrazol-1-yl)-phenyl]-3-cyclohexyl-acrylic acid (594 mg, 1.48 mmol) in methylene chloride (5 mL). The reaction mixture was then stirred for 15 min at 0° C. and then allowed to warm to 25° C. where it was stirred for 1.5 h. The reaction mixture was then treated with 2-aminothiazole (444 mg, 4.44 mmol), and the resulting suspension was stirred for 2 d at 25° C. The reaction mixture was concentrated in vacuo to remove methylene chloride, and the residue was diluted with ethyl acetate (70 mL) and a 1N aqueous hydrochloric acid solution (50 mL). The two layers were separated, and the aqueous layer was extracted with ethyl acetate (1×50 mL). The combined organic extracts were successively washed with a 1N aqueous hydrochloric acid solution (1×100 mL), a saturated aqueous sodium bicarbonate solution (1×100 mL) and a saturated aqueous sodium chloride solution (1×100 mL), dried over anhydrous magnesium sulfate, filtered, and concentrated in vacuo. Biotage chromatography (FLASH 40S, Silica, 5/1 to 3/2 hexanes/ethyl acetate) afforded (E)-2-[3-chloro-4-(5-trifluoromethyl-tetrazol-1-yl)-phenyl]-3-cyclohexyl-N-thiazol-2-yl-acrylamide (82 mg, 11 %) as an amorphous solid: EI-HRMS m/e calcd for $C_{20}H_{18}ClF_3N_6OS$ (M$^+$) 482.0903, found 482.0906.

EXAMPLE 19

(E)-3-Cyclopentyl-2-[4-(5-methyl-tetrazol-1-yl)-3-trifluoromethyl-phenyl]-N-thiazol-2-yl-acrylamide

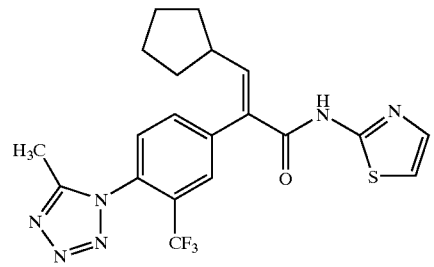

A solution of 2-(trifluoromethyl)-4-bromoaniline (4.8 g, 20 mmol) in dry tetrahydrofaran (20 mL) was cooled to 0° C. and then treated with acetic anhydride (8.2 g, 80 mmol). The reaction mixture was stirred at 0° C. for 10 min and then allowed to warm to 25° C. The reaction mixture was stirred at 25° C. for 2 h, at which time, thin layer chromatography analysis of the reaction mixture indicated the absence of starting material. The reaction mixture was then concentrated in vacuo. The crude residue precipitated from diethyl ether (50 mL) and hexanes (50 mL). The solid was collected by filtrated and washed with hexanes to afford N-(4-bromo-2-trifluoromethyl-phenyl)-acetamide (5.07 g, 90%) as an amorphous white solid: EI-HRMS m/e calcd for $C_9H_7BrF_3NO$ (M$^+$) 281.8352, found 281.8348.

A suspension of N-(4-bromo-2-trifluoromethyl-phenyl)-acetamide (2.41 g, 8.54 mmol) in acetonitrile (40 mL) was treated with methylene chloride (5 mL) to obtain a clear solution at 25° C. The resulting solution was treated with sodium azide (1.24 g, 19.1 mmol), and the reaction mixture was then cooled to 0° C. The reaction mixture was then treated with trifluoromethanesulfonic anhydride (3.59 g, 12.7 mmol). The resulting reaction mixture was allowed to warm to 25° C. where it was stirred overnight, at which time, thin layer chromatography analysis of the reaction mixture indicated the absence of starting material. The reaction mixture was then concentrated in vacuo. The resulting residue was diluted with ethyl acetate (50 mL) and water (50 mL). The two layers were separated, and the aqueous layer was extracted with ethyl acetate (1×30 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 2/1 hexanes/ethyl acetate) afforded 1-(4-bromo-2-trifluoromethyl-phenyl)-5-methyl-1H-tetrazole (1.85 g, 70%) as a white solid: EI-HRMS m/e calcd for $C_9H_6BrF_3N_4$ (M$^+$) 305.9728, found 305.9733.

A mixture of lithium chloride (8.48 g, 200 mmol, predried at 130° C. under high vacuum for 3 h) and copper cyanide (8.96 g, 100 mmol) in dry tetrahydrofuran (100 mL) was stirred at 25° C. under argon for 10 min to obtain a clear solution. The reaction mixture was then cooled to −70° C. and then slowly treated with a 2.0M solution of cyclopentylmagnesium chloride in diethyl ether (55 mL, 110 mmol). After the addition, the reaction mixture was allowed to warm to −30° C. where it was stirred for 5 min. The resulting reaction mixture was again cooled back to −70° C. and then slowly treated with methyl propiolate (7.99 g, 95 mmol). The reaction mixture was stirred overnight at −60° C. to −50° C. The reaction mixture was then slowly treated with a solution of iodine (34.3 g, 135 mmol) in dry tetrahydrofuran (30 mL), with the temperature kept at −70° C. to −60° C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (200 mL) and ammonium hydroxide (50 mL), and the organic compound was extracted into diethyl ether (3×100 mL). The combined organic extracts were successively washed with a saturated aqueous sodium thiosulfate solution (1×300 mL) and a saturated aqueous sodium chloride solution (1×300 mL). The organic layer was then dried over anhydrous magnesium sulfate, filtered, and concentrated in vacuo. Flash chromatography (Merck Silica gel 60, 230–400 mesh, 20/1 hexanes/diethyl ether) afforded (E)-3-cyclopentyl-2-iodo-acrylic acid methyl ester (25.8 g, 97%) as a yellow oil: EI-HRMS m/e calcd for $C_9H_{13}IO_2$ (M$^+$) 279.9960, found 279.9961.

A mixture of zinc dust (710 mg, 11 mmol, Aldrich, −325 mesh) and dry tetrahydrofuran (1 mL) under argon was treated with 1,2-dibromoethane (187 mg, 1 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (108 mg, 1 mmol), and the suspension was stirred for 15 min at 25° C. The reaction mixture was then treated dropwise with a solution of (E)-3-cyclopentyl-2-iodo-acrylic acid methyl ester (1.54 g, 5.5 mmol) in dry tetrahydrofuran (2 mL) over 3 min. The reaction mixture was then stirred at 40–45° C. for 1 h and then stirred overnight at 25° C. The reaction mixture was then diluted with dry tetrahydrofuran (4 mL), and the stirring was stopped to allow the excess zinc dust to settle down (~2 h). In a separate reaction flask, bis(dibenzylideneacetone) palladium(0) (81 mg, 0.15 mmol) and triphenylphosphine (156 mg, 0.6 mmol) in dry tetrahydrofuran (6 mL) was stirred at 25° C. under argon for 10 min and then treated with 1-(4-bromo-2-trifluoromethyl-phenyl)-5-methyl-1H-tetrazole (1.05 g, 3.5 mmol) and the freshly prepared zinc compound in tetrahydrofuran. The resulting brick red solution was heated at 40–45° C. over the weekend. The reaction mixture was cooled to 25° C. and then poured into a saturated aqueous ammonium chloride solution (50 mL), and the organic compound was extracted into ethyl acetate (3×35 mL). The combined organic extracts were washed with a saturated aqueous sodium chloride solution (1×100 mL), dried over anhydrous magnesium sulfate, filtered, and concentrated in vacuo. Flash chromatography (Merck Silica gel 60, 230–400 mesh, 4/1 to 1/1 hexanes/ethyl acetate) afforded (E)-3-cyclopentyl-2-[4-(5-methyl-tetrazol-1-yl)-3-trifluoromethyl-phenyl]-acrylic acid methyl ester (1.03 g, 77.6%) as a light yellow solid: EI-HRMS m/e calcd for $C_{18}H_{19}F_3N_4O_2$ (M$^+$) 380.1460, found 380.1453.

A solution of (E)-3-cyclopentyl-2-[4-(5-methyl-tetrazol-1-yl)-3-trifluoromethyl-phenyl]-acrylic acid methyl ester (199 mg, 0.52 mmol) in ethanol (3 mL) was treated with a 1N aqueous sodium hydroxide solution (2 mL). The solution was heated at 45–50° C. for 15 h, at which time, thin layer chromatography analysis of the reaction mixture indicated the absence of starting material. The reaction mixture was concentrated in vacuo to remove ethanol. The residue was diluted with water (10 mL) and extracted with diethyl ether (1×30 mL) to remove any neutral impurities. The aqueous layer was then acidified with a 1N aqueous hydrochloric acid solution, and the resulting acid was extracted into ethyl acetate (2×20 mL). The combined organic layers were washed with a saturated aqueous sodium chloride solution (1×50 mL), dried over anhydrous magnesium sulfate, filtered, and concentrated in vacuo to afford (E)-3-cyclopentyl-2-[4-(5-methyl-tetrazol-1-yl)-3-trifluoromethyl-phenyl]-acrylic acid (172 mg, 90%) as a yellow paste: EI-HRMS m/e calcd for $C_{17}H_{17}F_3N_4O_2$ (M$^+$) 366.1309, found 366.1309.

A solution of triphenylphosphine (204 mg, 0.78 mmol) in methylene chloride (8 mL) was cooled to 0° C. and then treated with N-bromosuccinimide (138 mg, 0.78 mmol). The reaction mixture was stirred at 0° C. for 30 min and then treated with a solution of (E)-3-cyclopentyl-2-[4-(5-methyl-tetrazol-1-yl)-3-trifluoromethyl-phenyl]-acrylic acid (143 mg, 0.39 mmol) in methylene chloride (5 mL). The reaction mixture was stirred for 15 min at 0° C. and then allowed to warm to 25° C. where it was stirred for 1.5 h. The reaction mixture was then treated with 2-aminothiazole (117 mg, 1.17 mmol), and the resulting suspension was stirred for 2 d at 25° C. The reaction mixture was then concentrated in vacuo to remove methylene chloride, and the residue was diluted with ethyl acetate (20 mL) and a 1N aqueous hydrochloric acid solution (30 mL). The two layers were separated, and the aqueous layer was extracted with ethyl acetate (1×15 mL). The combined organic extracts were successively washed with a 1N aqueous hydrochloric acid solution (1×50 mL), a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40S, Silica, 1/2 hexanes/ethyl acetate) afforded the (E)-3-cyclopentyl-2-[4-(5-methyl-tetrazol-1-yl)-3-trifluoromethyl-phenyl]-N-thiazol-2-yl-acrylamide (27 mg, 15.5%) as an amorphous white solid: EI-HRMS m/e calcd for $C_{20}H_{19}F_3N_6OS$ (M$^+$) 448.1293, found 448.1285.

EXAMPLE 20

(E)-3-Cyclopentyl-2-[3-methanesulfonyl-4-(5-methyl-tetrazol-1-yl)-phenyl]-N-thiazol-2-yl-acrylamide

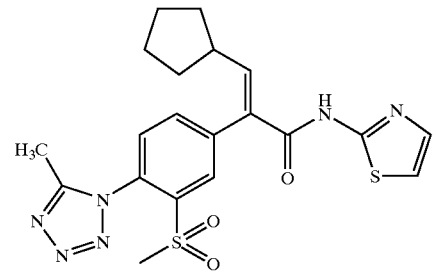

A solution of 2-nitro-4-bromoaniline (7.07 g, 32.6 mmol) in dry tetrahydrofuran (33 mL) was cooled to 0° C. and then treated with acetic anhydride (6.66 g, 65.2 mmol). The reaction mixture was stirred at 0° C. for 10 min and then allowed to warm to 25° C. The reaction mixture was stirred at 25° C. for 15 h, at which time, thin layer chromatography analysis of the reaction mixture indicated the presence of only starting material. The reaction mixture was then slowly treated with acetyl chloride (5 mL) and pyridine (5 mL) at 25° C. The resulting orange suspension was stirred at 25° C. for 2 h and then treated with water (50 mL). The organic compound was extracted into ethyl acetate (2×70 mL). The combined extracts were washed with a 3N aqueous hydrochloric acid solution (1×100 mL) and a saturated aqueous sodium chloride solution (1×100 mL), dried over anhydrous magnesium sulfate, filtered, and concentrated in vacuo to afford a yellow solid. The yellow solid was treated with diethyl ether (50 mL) and hexanes (50 mL). The solid was collected by filtration and washed with hexanes to afford N-(4-bromo-2-nitro-phenyl)-acetamide (6.82 g, 81%) as a yellow solid: mp 100–102° C.; EI-HRMS m/e calcd for $C_8H_7BrN_2O_3$ ($M^+$) 257.9640, found 257.9641.

A suspension of N-(4-bromo-2-nitro-phenyl)-acetamide (1.18 g, 4.55 mmol) in acetonitrile (25 mL) was cooled to 0° C. and then treated with sodium azide (838 mg, 13.65 mmol). The reaction mixture was then treated with trifluoromethanesulfonic anhydride (2.88 g, 10.25 mmol). The resulting reaction mixture was allowed to warm to 25° C. where it was stirred overnight, at which time, thin layer chromatography analysis of the reaction mixture indicated the absence of starting material. The reaction mixture was then concentrated in vacuo. The resulting residue was diluted with ethyl acetate (70 mL) and water (50 mL). The two layers were separated, and the aqueous layer was extracted with ethyl acetate (1×50 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 4/1 hexanes/ethyl acetate) afforded 1-(4-bromo-2-nitro-phenyl)-5-methyl-1H-tetrazole (1.16 g, 90%) as a white solid: mp 124–126° C.; EI-HRMS m/e calcd for $C_8H_6BrN_5O_2$ ($M^+$) 282.9705, found 282.9700.

A suspension of 1-(4-bromo-2-nitro-phenyl)-5-methyl-1H-tetrazole (1.13 g, 3.98 mmol) in methanol (40 mL, not completely dissolved in methanol even at hot conditions) was treated sequentially with ammonium chloride (3.19 g, 59.7 mmol), zinc dust (2.60 g, 39.8 mmol), and water (20 mL). Initially after the addition, the reaction was exothermic. The reaction mixture was then stirred for 1 h at 25° C. The reaction mixture was then filtered, and the residue was washed with methanol (50 mL) and ethyl acetate (100 mL). The filtrate was concentrated in vacuo, and the organic compound was extracted into ethyl acetate (3×50 mL). The combined organic extracts were washed with a saturated aqueous sodium chloride solution (1×200 mL), dried over anhydrous sodium sulfate, filtered, and concentrated in vacuo to afford 5-bromo-2-(5-methyl-tetrazol-1-yl)-phenylamine (0.90 g, 97%) as a white solid: EI-HRMS m/e calcd for $C_8H_8BrN_5$ ($M^+$) 252.9963, found 252.9962.

A solution of isoamyl nitrite (402 µL, 3 mmol) in dimethyl disulfide (2 mL, 22 mmol) at 25° C. was slowly treated with 5-bromo-2-(5-methyl-tetrazol-1-yl)-phenylamine (0.51 g, 2 mmol). The reaction was exothermic with gas evolution. The resulting brown reaction mixture was heated to 80–90° C. for 2 h, at which time, thin layer chromatography analysis of the reaction mixture indicated the absence of starting material. The reaction mixture was cooled to 25° C. and then concentrated in vacuo. The resulting residue was dissolved in ethyl acetate (50 mL). The organic layer was washed successively with a 1N aqueous hydrochloric acid solution (1×50 mL) and a saturated aqueous sodium chloride solution (1×50 mL), dried over anhydrous magnesium sulfate, filtered, and concentrated in vacuo. Biotage chromatography (FLASH 40M, Silica, 6/1 to 5/1 hexanes/ethyl acetate) afforded 1-(4-bromo-2-methylsulfanyl-phenyl)-5-methyl-1H-tetrazole (0.8 g) as a brown solid that was used without further purification and characterization.

A solution of 1-(4-bromo-2-methylsulfanyl-phenyl)-5-methyl-1H-tetrazole (0.8 g, ~2 mmol) in methylene chloride (12 mL) was cooled to −10° C. and then treated with 3-chloroperoxybenzoic acid (86% grade, 2.0 g, 12 mmol). The reaction mixture was stirred at −10° C. for 10 min and then allowed to warm to 25° C. where it was stirred over the weekend. At this time, thin layer chromatography analysis of the reaction mixture indicated the absence of starting material. The reaction mixture was then concentrated in vacuo. The resulting residue was dissolved in ethyl acetate (60 mL). The organic layer was washed successively with a saturated aqueous sodium bicarbonate solution (2×50 mL) and a saturated aqueous sodium chloride solution (1×50 mL), dried over anhydrous magnesium sulfate, filtered, and concentrated in vacuo to afford a yellow solid. Biotage chromatography (FLASH 40M, Silica, 3/1 hexanes/ethyl acetate) afforded 1-(4-bromo-2-methanesulfonyl-phenyl)-5-methyl-1H-tetrazole (313 mg, 49%) as a white solid: mp 175–176° C.; EI-HRMS m/e calcd for $C_9H_9BrN_4O_2S$ ($M^+$) 315.9630, found 315.9630.

A mixture of lithium chloride (8.48 g, 200 mmol, predried at 130° C. under high vacuum for 3 h) and copper cyanide (8.96 g, 100 mmol) in dry tetrahydrofuran (100 mL) was stirred at 25° C. under argon for 10 min to obtain a clear solution. The reaction mixture was then cooled to −70° C. and then slowly treated with a 2.0M solution of cyclopentylmagnesium chloride in diethyl ether (55 mL, 110 mmol). After the addition, the reaction mixture was allowed to warm to −30° C. where it was stirred for 5 min. The resulting reaction mixture was again cooled back to −70° C. and then slowly treated with methyl propiolate (7.99 g, 95 mmol). The reaction mixture was stirred overnight at −60° C. to −50° C. The reaction mixture was then slowly treated with a solution of iodine (34.3 g, 135 mmol) in dry tetrahydrofuran (30 mL), with the temperature kept at −70° C. to −60° C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (200 mL) and ammonium hydroxide (50 mL), and the organic compound was extracted into diethyl ether (3×100 mL). The combined organic extracts were successively washed with a saturated aqueous sodium thiosulfate solution (1×300 mL) and a saturated aqueous sodium chloride solution (1×300 mL). The organic layer was then dried over anhydrous magnesium sulfate, filtered, and concentrated in vacuo. Flash chromatography (Merck Silica gel 60, 230–400 mesh, 20/1 hexanes/diethyl ether) afforded (E)-3-cyclopentyl-2-iodo-acrylic acid methyl ester (25.8 g, 97%) as a yellow oil: EI-HRMS m/e calcd for $C_9H_{13}IO_2$ ($M^+$) 279.9960, found 279.9961.

A mixture of zinc dust (330 mg, 5 mmol, Aldrich, −325 mesh) and dry tetrahydrofuran (1 mL) under argon was treated with 1,2-dibromoethane (187 mg, 1 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (108 mg, 1 mmol), and the suspension was stirred for 15 min at 25° C. The reaction mixture was then treated dropwise with a solution of (E)-3-cyclopentyl-2-iodo-acrylic acid methyl ester (440 mg, 1.5 mmol) in dry tetrahydrofuran (1 mL). The resulting reaction mixture was then stirred at 40–45° C. for 1 h and then stirred overnight at 25° C. The reaction mixture was then diluted with dry tetrahydrofuran (3 mL), and the stirring was stopped to allow the excess zinc dust to settle down (~2 h). In a separate reaction flask, bis(dibenzylideneacetone)palladium(0) (27 mg, 0.05 mmol) and triphenylphosphine (52 mg, 0.2 mmol) in dry tetrahydrofuran (4 mL) was stirred at 25° C. under argon for 10 min and then treated with 1-(4-bromo-2-methanesulfonyl-phenyl)-5-methyl-1H-tetrazole (297 mg, 0.94 mmol) and the freshly prepared zinc compound in tetrahydrofuran. The resulting brick red solution was stirred at 40–45° C. over the weekend. The reaction mixture was cooled to 25° C. and then poured into a saturated aqueous ammonium chloride solution (30 mL), and the organic compound was extracted into ethyl acetate (3×25 mL). The combined organic extracts were washed with a saturated aqueous sodium chloride solution (1×50 mL), dried over anhydrous magnesium sulfate, filtered, and concentrated in vacuo. Biotage chromatography (FLASH 40M, Silica, 4/1 to 1/1 hexanes/ethyl acetate) afforded (E)-3-cyclopentyl-2-[3-methanesulfonyl-4-(5-methyl-tetrazol-1-yl)-phenyl]-acrylic acid methyl ester (289 mg, 78%) as an amorphous yellow solid: EI-HRMS Tile calcd for $C_{18}H_{22}N_4O_4S$ ($M^+$) 390.1362, found 390.1363.

A solution of (E)-3-cyclopentyl-2-[3-methanesulfonyl-4-(5-methyl-tetrazol-1-yl)-phenyl]-acrylic acid methyl ester (273 mg, 0.7 mmol) in ethanol (5 mL) was treated with a 1N aqueous sodium hydroxide solution (1.5 mL). The solution was heated at 45–50° C. for 15 h, at which time, thin layer chromatography analysis of the reaction mixture indicated the absence of starting material. The reaction mixture was concentrated in vacuo to remove ethanol. The residue was diluted with water (20 mL) and extracted with diethyl ether (1×30 mL) to remove any neutral impurities. The aqueous layer was then acidified with a 1N aqueous hydrochloric acid solution, and the resulting acid was extracted into ethyl acetate (2×30 mL). The combined organic layers were washed with a saturated aqueous sodium chloride solution (1×50 mL), dried over anhydrous magnesium sulfate, filtered, and concentrated in vacuo to afford (E)-3-cyclopentyl-2-[3-methanesulfonyl-4-(5-methyl-tetrazol-1-yl)-phenyl]-acrylic acid (262 mg, 100%) as a yellow solid: EI-HRMS m/e calcd for $C_{17}H_{20}N_4O_4S$ ($M^+$) 376.1205, found 376.1204.

A solution of triphenylphosphine (262 mg, 1 mmol) in methylene chloride (6 mL) was cooled to 0° C. and then treated with N-bromosuccinimide (178 mg, 1 mmol). The reaction mixture was stirred at 0° C. for 30 min and then treated with (E)-3-cyclopentyl-2-[3-methanesulfonyl-4-(5-methyl-tetrazol-1-yl)-phenyl]-acrylic acid (190 mg, 0.5 mmol). The reaction mixture was stirred for 15 min at 0° C. and then allowed to warm to 25° C. where it was stirred for 1.5 h. The reaction mixture was then treated with 2-aminothiazole (250 mg, 2.5 mmol), and the resulting suspension was stirred for 2 d at 25° C. The reaction mixture was then concentrated in vacuo to remove methylene chloride, and the residue was diluted with ethyl acetate (20 mL) and water (30 mL). The two layers were separated, and the aqueous layer was extracted with ethyl acetate (1×15 mL). The combined organic extracts were successively washed with a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40S, Silica, 3/1 hexanes/ethyl acetate) afforded (E)-3-cyclopentyl-2-[3-methanesulfonyl-4-(5-methyl-tetrazol-1-yl)-phenyl]-N-thiazol-2-yl-acrylamide (42 mg, 18%) as an amorphous white solid: EI-HRMS m/e calcd for $C_{20}H_{22}N_6O_3S_2$ ($M^+$) 458.1195, found 458.1192.

EXAMPLE 21

(E)-4-Cyclopentyl-2-[4-(5-methyl-tetrazol-1-yl)-3-trifluoromethyl-phenyl]-but-2-enoic acid thiazol-2-ylamide

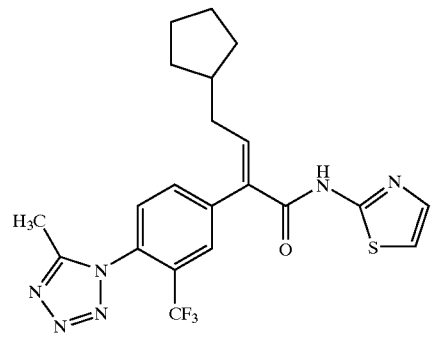

A solution of 2-(trifluoromethyl)-4-bromoaniline (4.8 g, 20 mmol) in dry tetrahydrofuran (20 mL) was cooled to 0° C. and then treated with acetic anhydride (8.2 g, 80 mmol). The reaction mixture was stirred at 0° C. for 10 min and then allowed to warm to 25° C. The reaction mixture was stirred at 25° C. for 2 h, at which time, thin layer chromatography analysis of the reaction mixture indicated the absence of starting material. The reaction mixture was then concentrated in vacuo. The crude residue precipitated from diethyl ether (50 mL) and hexanes (50 mL). The solid was collected by filtrated and washed with hexanes to afford N-(4-bromo-2-trifluoromethyl-phenyl)-acetamide (5.07 g, 90%) as an amorphous white solid: El-HRMS m/e calcd for $C_9H_7BrF_3NO$ (M) 281.8352, found 281.8348.

A suspension of N-(4-bromo-2-trifluoromethyl-phenyl)-acetamide (2.41 g, 8.54 mmol) in acetonitrile (40 mL) was treated with methylene chloride (5 mL) to obtain a clear solution at 25° C. The resulting solution was treated with sodium azide (1.24 g, 19.1 mmol), and the reaction mixture was then cooled to 0° C. The reaction mixture was then treated with trifluoromethanesulfonic anhydride (3.59 g, 12.7 mmol). The resulting reaction mixture was allowed to warm to 25° C. where it was stirred overnight, at which time, thin layer chromatography analysis of the reaction mixture indicated the absence of starting material. The reaction mixture was then concentrated in vacuo. The resulting residue was diluted with ethyl acetate (50 mL) and water (50 mL). The two layers were separated, and the aqueous layer was extracted with ethyl acetate (1×30 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 2/1 hexanes/ethyl acetate) afforded 1-(4-bromo-2-trifluoromethyl-phenyl)-5-methyl-1H-tetrazole (1.85 g, 70%) as a white solid: EI-HRMS m/e calcd for $C_9H_6BrF_3N_4$ ($M^+$) 305.9728, found 305.9733.

A mixture of zinc dust (3.92 g, 60 mmol, Aldrich, −325 mesh) and dry tetrahydrofuran (4 mL) under argon was treated with 1,2-dibromoethane (0.56 g, 3 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (0.32 g, 3 mmol, and the suspension was stirred for 15 min at 25° C. The reaction mixture was then treated dropwise with a solution of cyclopentylmethyl iodide (4.2 g, 20 mmol) in dry tetrahydrofuran (7 mL) over 5 min. During the addition, the temperature rose to 50° C., and the reaction mixture was stirred overnight at 40–45° C. The reaction mixture was then cooled to 25° C. and diluted with dry tetrahydrofuran (5 mL). The stirring was stopped to allow the excess zinc dust to settle down (~2 h). In a separate reaction flask, a mixture of lithium chloride (1.7 g, 40 mmol, predried at 130° C. under high vacuum for 2 h) and copper cyanide (1.79 g, 20 mmol) in dry tetrahydrofuran (20 mL) was stirred for 10 min at 25° C. to obtain a clear solution. The reaction mixture was cooled to −70° C. and then the slowly treated with the freshly prepared zinc solution using a syringe. After the addition, the reaction mixture was allowed to warm to −30° C., where it was stirred for 5 min. The reaction mixture was again cooled back to −70° C. and then slowly treated with methyl propiolate (1.52 g, 18 mmol). The reaction mixture was stirred for 4 h at −40° C. to −30° C. and then slowly treated with a solution of iodine (6.85 g, 27 mmol) in dry tetrahydrofuran (10 mL), with the temperature kept at −70° C. to −60° C. After the addition of the iodine solution, the cooling bath was removed, and the reaction mixture was allowed to warm to 25° C. where it was stirred for 1 h. The reaction mixture was then poured into a solution consisting of a saturated aqueous ammonium chloride solution (90 mL) and ammonium hydroxide (10 mL), and the organic compound was extracted into diethyl ether (3×50 mL). The combined ether extracts were successively washed with a saturated aqueous sodium thiosulfate solution (1×100 mL) and a saturated aqueous sodium chloride solution (1×100 mL), dried over anhydrous magnesium sulfate, filtrated, and concentrated in vacuo. Biotage chromatography (FLASH 40M, Silica, 9/1 hexanes/diethyl ether) afforded (E)-4-cyclopentyl-2-iodo-but-2-enoic acid methyl ester (4.56 g, 86%) as a colorless oil: EI-HRMS m/e calcd for $C_{10}H_{15}IO_2$ ($M^+$) 294.0116, found 294.0114.

A mixture of zinc dust (330 mg, 5 mmol, Aldrich, −325 mesh) and dry tetrahydrofuran (1 mL) under argon was treated with 1,2-dibromoethane (187 mg, 1 mmol). The zinc suspension was then heated with a heat gun to ebullition, allowed to cool, and heated again. This process was repeated three times to make sure the zinc dust was activated. The activated zinc dust suspension was then treated with trimethylsilyl chloride (108 mg, 1 mmol), and the suspension was stirred for 15 min at 25° C. The reaction mixture was then treated dropwise with a solution of (E)-4-cyclopentyl-2-iodo-but-2-enoic acid methyl ester (590 mg, 2 mmol) in dry tetrahydrofuran (1 mL). After the addition, the reaction mixture was stirred for 1 h at 40–45° C. and then stirred overnight at 25° C. The reaction mixture was then diluted with dry tetrahydrofuran (3 mL), and the stirring was stopped to allow the excess zinc dust to settle down (2 h). In a separate reaction flask, bis(dibenzylideneacetone)palladium(0) (38 mg, 0.07 mmol) and triphenylphosphine (73 mg, 0.28 mmol) in dry tetrahydrofuran (7 mL) was stirred at 25° C. under argon for 10 min and then treated with 1-(4-bromo-2-trifluoromethyl-phenyl)-5-methyl-1 H-tetrazole (350 mg, 1.4 mmol) and the freshly prepared zinc compound in tetrahydrofuran. The resulting brick red solution was heated at 45–50° C. for 20 h. The reaction mixture was cooled to 25° C. and then poured into a saturated aqueous ammonium chloride solution (30 mL), and the organic compound was extracted into ethyl acetate (3×25 mL). The combined organic extracts were washed with a saturated aqueous sodium chloride solution (1×50 mL), dried over anhydrous magnesium sulfate, filtered, and concentrated in vacuo. Biotage chromatography (FLASH 40M, Silica, 4/1 to 1/1 hexanes/ethyl acetate) afforded (E)-4-cyclopentyl-2-[4-(5-methyl-tetrazol-1-yl)-3-trifluoromethyl-phenyl]-but-2-enoic acid methyl ester (360 mg, 65%) as an amorphous white solid: EI-HRMS m/e calcd for $C_{19}H_{21}F_3N_4O_2$ ($M^+$) 394.1617, found 394.1621.

A solution of (E)-4-cyclopentyl-2-[4-(5-methyl-tetrazol-1-yl)-3-trifluoromethyl-phenyl]-but-2-enoic acid methyl ester (359 mg, 0.9 mmol) in ethanol (5 mL) was treated with a 1N aqueous sodium hydroxide solution (3 mL). The solution was heated at 45–50° C. for 15 h, at which time, thin layer chromatography analysis of the reaction mixture indicated the absence of starting material. The reaction mixture was concentrated in vacuo to remove ethanol. The residue was diluted with water (20 mL) and extracted with diethyl ether (1×30 mL) to remove any neutral impurities. The aqueous layer was then acidified with a 1N aqueous hydrochloric acid solution, and the resulting acid was extracted into ethyl acetate (2×30 mL). The combined organic layers were washed with a saturated aqueous sodium chloride solution (1×50 mL), dried over anhydrous magnesium sulfate, filtered, and concentrated in vacuo to afford (E)-4-cyclopentyl-2-[4-(5-methyl-tetrazol-1-yl)-3-trifluoromethyl-phenyl]-but-2-enoic acid (340 mg, 98%) as a yellow solid: EI-HRMS m/e calcd for $C_{18}H_{19}F_3N_4O_2$ ($M^+$) 380.1460, found 380.1460.

A solution of triphenylphosphine (450 mg, 1.72 mmol) in methylene chloride (20 mL) was cooled to 0° C. and then treated with N-bromosuccinimide (306 mg, 1.72 mmol). The reaction mixture was stirred at 0° C. for 30 min and then treated with a solution of the (E)-4-cyclopentyl-2-[4-(5-methyl-tetrazol-1-yl)-3-trifluoromethyl-phenyl]-but-2-enoic acid (326 mg, 0.86 mmol) in methylene chloride (5 mL). The reaction mixture was stirred for 15 min at 0° C. and then allowed to warm to 25° C. where it was stirred for 1.5 h. The reaction mixture was then treated with 2-aminothiazole (257 mg, 2.57 mmol), and the resulting suspension was stirred for 2 d at 25° C. The reaction mixture was then concentrated in vacuo to remove methylene chloride, and the residue was diluted with ethyl acetate (20 mL) and water (30 mL). The two layers were separated, and the aqueous layer was extracted with ethyl acetate (1×15 mL). The combined organic extracts were successively washed with a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40S, Silica, 3/1 hexanes/ethyl acetate) afforded (E)-4-cyclopentyl-2-[4-(5-methyl-tetrazol-1-yl)-3-trifluoromethyl-phenyl]-but-2-enoic acid thiazol-2-ylamide (52 mg, 13%) as an amorphous white solid: EI-HRMS m/e calcd for $C_{21}H_{21}F_3N_6OS$ ($M^+$) 462.1450, found 462.1451.

EXAMPLE 22

(E)-1-{3-Cyclopentyl-2-[3-fluoro-4-(5-methyl-tetrazol-1-yl)-phenyl]-acryloyl}-3-methyl-urea

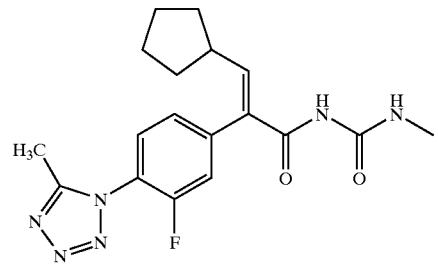

A solution of 2-fluoro-4-iodoaniline (4.74 g, 20 mmol) in dry tetrahydrofuran (20 mL) was cooled to 0° C. and then treated with acetic anhydride (8.2 g, 80 mmol). The reaction mixture was stirred for 10 min at 0° C. and then was allowed to warm to 25° C. where it was stirred for 2 h. After this time, thin layer chromatography analysis of the reaction mixture indicated the absence of starting material. The reaction mixture was then concentrated in vacuo to afford a crude residue. The residue precipitated from diethyl ether (50 mL) and hexanes (50 mL). The solid was collected by filtration and washed with hexanes to afford N-(2-fluoro-4-iodo-phenyl)-acetamide (5.12 g, 92%) as a white crystalline solid: mp 152–154OC; EI-HRMS m/e calcd for $C_8H_7FINO$ (M$^+$) 278.9556, found 278.9559.

A suspension of N-(2-fluoro-4-iodo-phenyl)-acetamide (5 g, 18.24 mmol) in acetonitrile (100 mL) was cooled to 0° C. and then treated with sodium azide (3.56 g, 54.7 mmol). The reaction mixture was then treated with trifluoromethane-sulfonic anhydride (13.6 g, 48 mmol). The resulting reaction mixture was allowed to warm to 25° C. where it was stirred overnight, at which time, thin layer chromatography analysis of the reaction mixture indicated the absence of starting material. The reaction mixture was then concentrated in vacuo. The resulting residue was diluted with ethyl acetate (100 mL) and water (100 mL). The two layers were separated, and the aqueous layer was extracted with ethyl acetate (1×50 mL). The combined organic extracts were washed with a saturated aqueous sodium chloride solution (1×100 mL), dried over anhydrous magnesium sulfate, filtered, and concentrated in vacuo. Biotage chromatography (FLASH 40M, Silica, 4/1 hexanes/ethyl acetate) afforded 1-(2-fluoro-4-iodo-phenyl)-5-methyl-1H-tetrazole (3.45 g, 62%) as a white solid: mp 122–124° C.; EI-HRMS m/e calcd for $C8H_6FIN_4$ (M$^+$) 303.9621, found 303.9615.

A mixture of lithium chloride (8.48 g, 200 mmol, predried at 130° C. under high vacuum for 3 h) and copper cyanide (8.96 g, 100 mmol) in dry tetrahydrofuran (100 mL) was stirred at 25° C. under argon for 10 min to obtain a clear solution. The reaction mixture was then cooled to −70° C. and then slowly treated with a 2.0M solution of cyclopen-tylmagnesium chloride in diethyl ether (55 mL, 110 mmol). After the addition, the reaction mixture was allowed to warm to −30° C. where it was stirred for 5 min. The resulting reaction mixture was again cooled back to −70° C. and then slowly treated with methyl propiolate (7.99 g, 95 mmol). The reaction mixture was stirred overnight at −60° C. to −50° C. The reaction mixture was then slowly treated with a solution of iodine (34.3 g, 135 mmol) in dry tetrahydro-furan (30 mL), with the temperature kept at −70° C. to −60° C. After addition of the iodine solution, the cooling bath was removed, and the reaction mixture was allowed to warm to 25° C. where it was stirred for 2 h. The reaction mixture was then poured into a solution consisting of a saturated aqueous ammonium chloride solution (200 mL) and ammonium hydroxide (50 mL), and the organic compound was extracted into diethyl ether (3×100 mL). The combined organic extracts were successively washed with a saturated aqueous sodium thiosulfate solution (1×300 mL) and a saturated aqueous sodium chloride solution (1×300 mL). The organic layer was then dried over anhydrous magne-sium sulfate, filtered, and concentrated in vacuo. Flash chromatography (Merck Silica gel 60, 230–400 mesh, 20/1 hexanes/diethyl ether) afforded (E)-3-cyclopentyl-2-iodo-acrylic acid methyl ester (25.8 g, 97%) as a yellow oil: EI-HRMS m/e calcd for $C_9H_{13}IO_2$ (M$^+$) 279.9960, found 279.9961.

A mixture of zinc dust (650 mg, 10 mmol, Aldrich, −325 mesh) and dry tetrahydrofuran (1 mL) under argon was treated with 1,2-dibromoethane (187 mg, 1 mmol). The zinc suspension was then heated with a heat gun to ebullition, allowed to cool, and heated again. This process was repeated three times to make sure the zinc dust was activated. The activated zinc dust suspension was then treated with trim-ethylsilyl chloride (108 mg, 1 mmol), and the suspension was stirred for 15 min at 25° C. The reaction mixture was then treated dropwise with a solution of (E)-3-cyclopentyl-2-iodo-acrylic acid methyl ester (2.21 g, 7.5 mmol) in dry tetrahydrofuran (3 mL) over 3 min. The resulting reaction mixture was then stirred at 40–45° C. for 1 h and then stirred overnight at 25° C. The reaction mixture was then diluted with dry tetrahydrofuran (5 mL), and the stirring was stopped to allow the excess zinc dust to settle down (~2 h). In a separate reaction flask, bis(dibenzylideneacetone) palladium(0) (90 mg, 0.16 mmol) and triphenylphosphine (160 mg, 0.6 mmol) in dry tetrahydrofuran (10 mL) was stirred at 25° C. under argon for 10 min and then treated with 1-(2-fluoro-4-iodo-phenyl)-5-methyl-1H-tetrazole (1.52 g, 5 mmol) and the freshly prepared zinc compound in tetrahy-drofuran. The resulting brick red solution was stirred at 25° C. over the weekend and then heated at 40–45° C. for 4 h. The reaction mixture was cooled to 25° C. and then poured into a saturated aqueous ammonium chloride solution (50 mL), and the organic compound was extracted into ethyl acetate (3×50 mL). The combined organic extracts were washed with a saturated aqueous sodium chloride solution (1×100 mL), dried over anhydrous magnesium sulfate, filtered, and concentrated in vacuo. Flash chromatography (Merck Silica gel 60, 230–400 mesh, 4/1 to 1/1 hexanes/ ethyl acetate) afforded (E)-3-cyclopentyl-2-[3-fluoro-4-(5-methyl-tetrazol-1-yl)-phenyl]-acrylic acid methyl ester (1.14 g, 68%) as a light yellow solid: mp 111–114° C.; EI-HRMS m/e calcd for $C_{17}H_{19}FN_4O_2$ (M$^+$) 330.1492, found 330.1493.

A solution of (E)-3-cyclopentyl-2-[3-fluoro-4-(5-methyl-tetrazol-1-yl)-phenyl]-acrylic acid methyl ester (720 mg, 2.18 mmol) in ethanol (15 mL) was treated with a 1N aqueous sodium hydroxide solution (5 mL). The solution was heated at 45–50° C. for 15 h, at which time, thin layer chromatography analysis of the reaction mixture indicated the absence of starting material. The reaction mixture was concentrated in vacuo to remove ethanol. The residue was diluted with water (30 mL) and extracted with diethyl ether (1×50 mL) to remove any neutral impurities. The aqueous layer was then acidified with a 1N aqueous hydrochloric acid solution, and the resulting acid was extracted into ethyl acetate (2×50 mL). The combined organic layers were washed with a saturated aqueous sodium chloride solution (1×100 mL), dried over anhydrous magnesium sulfate, filtered, and concentrated in vacuo to afford (E)-3-cyclopentyl-2-[3-fluoro-4-(5-methyl-tetrazol-1-yl)-phenyl]-acrylic acid (690 mg, 100%) as a white solid: mp 182–185° C.; EI-HRMS m/e calcd for $C_{16}H_{17}FN_4O_2$ (M$^+$) 316.1336, found 316.1334.

A solution of (E)-3-cyclopentyl-2-[3-fluoro-4-(5-methyl-tetrazol-1-yl)-phenyl]-acrylic acid (158 mg, 0.5 mmol) in fluorobenzene (1 mL) and N,N-dimethylformamide (2 µL) at 25° C. was treated dropwise with oxalyl chloride (54 µL, 0.6 mmol) over 2–3 min. The clear solution was stirred for 1 h at 25° C. and then treated with methyl urea (111 mg, 1.5 mmol). The resulting suspension was heated at 70° C. (bath temperature) for 10 min and then treated with pyridine (81 µL, 1 mmol). The reaction mixture was then stirred at 70° C. for 20 h. The reaction mixture was then cooled to 25° C. and diluted with ethyl acetate (30 mL) and a 3N aqueous hydrochloric acid solution (30 mL). The two layers were separated, and the aqueous layer was extracted with ethyl acetate (1×20 mL). The combined organic extracts were successively washed with a saturated aqueous sodium bicarbonate solution (1×50 mL) and a saturated aqueous sodium chloride solution (1×50 mL), dried over anhydrous magnesium sulfate, filtered, and concentrated in vacuo. Biotage chromatography (FLASH 40M, Silica, 1/1 hexanes/ethyl acetate) afforded the (E)-1-{3-cyclopentyl-2-[3-fluoro-4-(5-methyl-tetrazol-1-yl)-phenyl]-acryloyl}-3-methyl-urea (41 mg, 22%) as a white solid: mp 186–192° C.; EI-HRMS m/e calcd for $C_{18}H_{21}FN_6O_2$ ($M^+$) 372.1710, found 372.1708.

Biological Activity Examples

Example A

In Vitro Glucokinase Activity

Glucokinase Assay: Glucokinase (GK) was assayed by coupling the production of glucose-6-phosphate to the generation of NADH with glucose-6-phosphate dehydrogenase (G6PDH, 0.75–1 kunits/mg; Boehringer Mannheim, Indianapolis, Ind.) from *Leuconostoc mesenteroides* as the coupling enzyme (Scheme 2). Recombinant Scheme 2

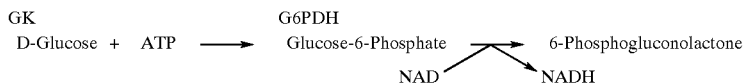

Human liver GK1 was expressed in *E. coli* as a glutathione S-transferase fusion protein (GST-GK) [Liang et al, 1995] and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet et al., 1990).

The assay was conducted at 25° C. in a flat bottom 96-well tissue culture plate from Costar (Cambridge, Mass.) with a final incubation volume of 120 µl. The incubation mixture contained: 25 mM Hepes buffer (pH, 7.1), 25 mM KCl, 5 mM D-glucose, 1 mM ATP, 1.8 mM NAD, 2 mM $MgCl_2$, 1 µM sorbitol-6-phosphate, 1 mM dithiothreitol, test drug or 10% DMSO, 1.8 unit/ml G6PDH, and GK (see below). All organic reagents were >98 % pure and were from Boehringer Mannheim with the exceptions of D-glucose and Hepes that were from Sigma Chemical Co, St Louis, Mo. Test compounds were dissolved in DMSO and were added to the incubation mixture minus GST-GK in a volume of 12 µl to yield a final DMSO concentration of 10%. This mix was preincubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 µl GST-GK.

After addition of enzyme, the increase in optical density (OD) at 340 nm was monitored over a 10 minute incubation period as a measure of GK activity. Sufficient GST-GK was added to produce an increase in $OD_{340}$ of 0.08 to 0.1 units over the 10 minute incubation period in wells containing 10% DMSO, but no test compound. Preliminary experiments established that the GK reaction was linear over this period of time even in the presence of activators that produced a 5-fold increase in GK activity. The GK activity in control wells was compared with the activity in wells containing test GK activators, and the concentration of activator that produced a 50% increase in the activity of GK, i.e., the $SC_{1.5}$, was calculated. All of the compounds of formula IA or IB described in the Synthesis Examples had an $SC_{1.5}$ less than or equal to 30 µM.

Example B

Glucokinase Activator in vivo Screen Protocol

C57BL/6J mice were orally dosed via gavage with Glucokinase (GK) activator at 50 mg/kg body weight following a two hour fasting period. Blood glucose determinations were made five times during the six hour post-dose study period.

Mice (n=6) were weighed and fasted for a two hour period prior to oral treatment. GK activators were formulated at 6.76 mg/ml in Gelucire vehicle (Ethanol:Gelucire44/14:PEG400q.s. 4:66:30 v/w/v. Mice were dosed orally with 7.5µL formulation per gram of body weight to equal a 50 mg/kg dose. Immediately prior to dosing, a pre dose (time zero) blood glucose reading is acquired by snipping off a small portion of the animals tail (~1 mm) and collecting 15 µL blood into a heparinized capillary tube for analysis. Following GK activator administration, additional blood glucose readings were taken at 1, 2, 4, and 6 hours post dose from the same tail wound. Results were interpreted by comparing the mean blood glucose values of six vehicle treated mice with six GK activator treated mice over the six hour study duration. Compounds are considered active when they exhibit a statistically significant ($p \leq 0.05$) decrease in blood glucose compared to vehicle for two consecutive assay time points.

What is claimed is:

1. A tetrazole selected from the group consisting of a compound of the formula:

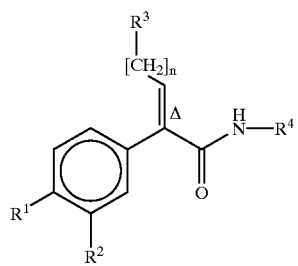

I-A wherein one of $R^1$ or $R^2$ is

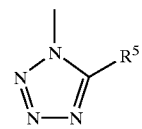

and the other is hydrogen, halogen, lower alkyl sulfonyl, perfluoro-lower alkyl, cyano, or nitro;

$R^3$ is cycloalkyl;

$R^4$ is a six-membered heteroaromatic ring connected by a ring carbon atom to the amide group shown, which heteroaromatic ring contains from 1 to 3 heteroatoms selected from the group consisting of oxygen, sulfur and nitrogen with a first heteroatom being nitrogen adjacent to the connecting ring carbon atom, said heteroaromatic ring being unsubstituted or monosubstituted with halogen at a position on a ring carbon atom other than that adjacent to said connecting carbon atom;

$R^5$ is lower alkyl, or perfluoro lower alkyl;

$R^6$ is hydrogen or lower alkyl;

n is 0 or 1; Δ denotes a trans configuration across the double bond;

and a pharmaceutically acceptable salt thereof.

2. A tetrazole of claim 1 wherein $R^1$ is

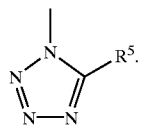

3. A tetrazole of claim 2 wherein $R^5$ is lower alkyl.

4. A tetrazole of claim 3 wherein $R^3$ is cyclopentyl.

5. A tetrazole of claim 4 wherein $R^4$ is substituted or unsubstituted pyridine.

6. A tetrazole of claim 5 wherein $R^2$ is halogen.

7. A tetrazole of claim 6 which is (E)-N-(5-bromo-pyridin-2-yl)-3-cyclopentyl-2-[3-fluoro-4-(5-methyl-tetrazol-1-yl)-phenyl]-acrylamide.

8. A tetrazole selected from the group consisting of a compound of the formula:

I-B

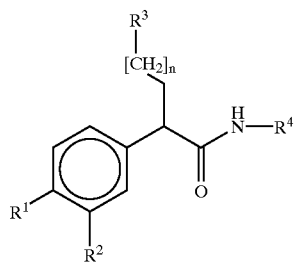

wherein
one of $R^1$ or $R^2$ is

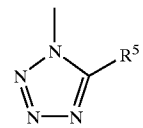

and the other is hydrogen, halogen, lower alkyl sulfonyl, perfluoro-lower alkyl, cyano, or nitro;

$R^3$ is cycloalkyl;

$R^4$ is a six-membered heteroaromatic ring connected by a ring carbon atom to the amide group shown, which heteroaromatic ring contains from 1 to 3 heteroatoms selected from the group consisting of oxygen, sulfur and nitrogen with a first heteroatom being nitrogen adjacent to the connecting ring carbon atom, said heteroaromatic ring being unsubstituted or monosubstituted with halogen at a position on a ring carbon atom other than that adjacent to said connecting carbon atom;

$R^5$ is lower alkyl, or perfluoro lower alkyl;

$R^6$ is hydrogen or lower alkyl;

n is 1 or 1; the * represents the asymmetric carbon atom and a pharmaceutically acceptable salt thereof.

9. A tetrazole of claim 8 wherein $R^1$ is

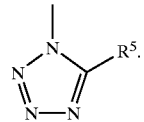

10. A tetrazole of claim 9 wherein $R^5$ is lower alkyl.

11. A tetrazole of claim 10 wherein $R^3$ is cyclopentyl.

12. A tetrazole of claim 11 wherein $R^4$ is substituted or unsubstituted pyridine.

13. A tetrazole of claim 12 wherein $R^2$ is halogen.

14. A tetrazole of claim 13 which is N-(5-bromo-pyridin-2-yl)-3-cyclopentyl-2-[3-fluoro-4-(5-methyl-tetrazol-1-yl)-phenyl]-propionamide.

15. A tetrazole of claim 13 which is N-(5-bromo-pyridin-2-yl)-3-cyclopentyl-2-[3-chloro-4-(5-methyl-tetrazol-1-yl)-phenyl]-propionamide.

16. A tetrazole of claim 12 wherein $R^2$ is perfluoro lower alkyl.

17. A tetrazole of claim 16 which is N-(5-bromo-pyridin-2-yl)-3-cyclopentyl-2-[4-(5-methyl-tetrazol-1-yl)-3-trifluoromethyl-phenyl]-propionamide.

* * * * *

UNITED STATES PATENT AND TRADEMARK OFFICE
CERTIFICATE OF CORRECTION

PATENT NO.   : 6,441,180 B1
DATED        : August 27, 2002
INVENTOR(S)  : Achyutharao Sidduri It is certified that error appears in the above-identified patent and that said Letters Patent is hereby corrected as shown below:

Column 69,
Lines 37-46, replace the present formula with:

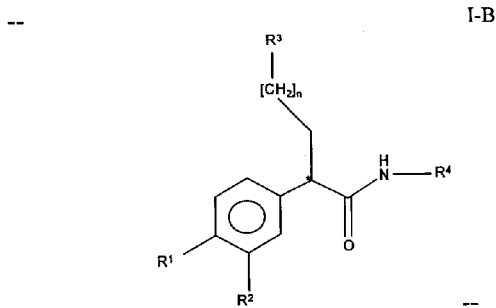

Signed and Sealed this

Fourteenth Day of January, 2003

JAMES E. ROGAN
*Director of the United States Patent and Trademark Office*